(12) United States Patent
Hyde et al.

(10) Patent No.: US 8,246,565 B2
(45) Date of Patent: Aug. 21, 2012

(54) DEVICE FOR PASSIVELY REMOVING A TARGET COMPONENT FROM BLOOD OR LYMPH OF A VERTEBRATE SUBJECT

(75) Inventors: Roderick A. Hyde, Redmond, WA (US); Muriel Y. Ishikawa, Livermore, CA (US); Edward K. Y. Jung, Bellevue, WA (US); Robert Langer, Newton, MA (US); Eric C. Leuthardt, St. Louis, MO (US); Nathan P. Myhrvold, Bellevue, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 299 days.

(21) Appl. No.: 12/660,926

(22) Filed: Mar. 5, 2010

(65) Prior Publication Data

US 2010/0268199 A1    Oct. 21, 2010

Related U.S. Application Data

(63) Continuation-in-part of application No. 12/660,928, filed on Mar. 5, 2010, and a continuation-in-part of application No. 12/380,400, filed on Feb. 25, 2009, and a continuation-in-part of application No. 12/380,399, filed on Feb. 25, 2009.

(51) Int. Cl.
*A61M 37/00* (2006.01)
*C02F 1/44* (2006.01)
*A61K 9/22* (2006.01)

(52) U.S. Cl. ............ 604/4.01; 604/5.01; 604/5.04; 604/891.1; 210/502.1; 210/645

(58) Field of Classification Search .......... 604/4.01, 604/5.01, 5.04, 6.09, 6.08, 6.11, 500, 507, 604/508; 210/645, 501, 502.1, 745, 739
See application file for complete search history.

(56) References Cited

U.S. PATENT DOCUMENTS
4,444,878 A    4/1984    Paulus
(Continued)

FOREIGN PATENT DOCUMENTS
EP    1 550 454 A1    7/2005

OTHER PUBLICATIONS

Ng, David C. et al.; Real time in vivo imaging and measurement of serine protease activity in the mouse hippocampus using a dedicated complementary metal-oxide semiconductor imaging device; Journal of Neuroscience Methods; 2006; pp. 23-30; vol. 156; Elsevier B.V.

(Continued)

*Primary Examiner* — Leslie Deak

(57) ABSTRACT

Devices, systems, and methods are described herein for controlling or modulating the levels of one or more target components in the blood and/or lymph of a vertebrate subject. Devices and systems are provided that include a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components.

53 Claims, 3 Drawing Sheets

U.S. PATENT DOCUMENTS

| | | | |
|---|---|---|---|
| 4,955,857 A * | 9/1990 | Shettigar | 604/6.06 |
| 5,092,886 A | 3/1992 | Dobos-Hardy | |
| 5,107,422 A | 4/1992 | Kamentsky et al. | |
| 5,281,199 A | 1/1994 | Ensminger et al. | |
| 5,411,551 A | 5/1995 | Winston et al. | |
| 5,470,570 A | 11/1995 | Taylor et al. | |
| 5,474,772 A | 12/1995 | Maddock | |
| 5,702,432 A | 12/1997 | Chen et al. | |
| 5,790,691 A | 8/1998 | Narayanswamy et al. | |
| 5,797,898 A | 8/1998 | Santini, Jr. et al. | |
| 5,804,563 A | 9/1998 | Still et al. | |
| 5,830,207 A | 11/1998 | Leeb et al. | |
| 5,831,012 A | 11/1998 | Nilsson et al. | |
| 5,928,195 A | 7/1999 | Malamud et al. | |
| 5,985,579 A | 11/1999 | Buechler et al. | |
| 6,030,653 A | 2/2000 | Rosenthal | |
| 6,039,946 A * | 3/2000 | Strahilevitz | 424/140.1 |
| 6,132,992 A | 10/2000 | Ledbetter et al. | |
| 6,190,691 B1 | 2/2001 | Mak | |
| 6,240,312 B1 | 5/2001 | Alfano et al. | |
| 6,255,461 B1 | 7/2001 | Mosbach et al. | |
| 6,287,516 B1 * | 9/2001 | Matson et al. | 422/44 |
| 6,387,674 B1 | 5/2002 | Trasciatti et al. | |
| 6,416,495 B1 | 7/2002 | Kriesel et al. | |
| 6,425,867 B1 | 7/2002 | Vaezy et al. | |
| 6,451,257 B1 | 9/2002 | Flamer | |
| 6,454,759 B2 | 9/2002 | Krulevitch et al. | |
| 6,471,872 B2 | 10/2002 | Kitaevich et al. | |
| 6,488,704 B1 | 12/2002 | Connelly et al. | |
| 6,551,235 B2 | 4/2003 | Forsell | |
| 6,554,822 B1 | 4/2003 | Holschneider et al. | |
| 6,571,125 B2 | 5/2003 | Thompson | |
| 6,612,535 B1 | 9/2003 | Tai et al. | |
| 6,669,683 B2 | 12/2003 | Santini, Jr. et al. | |
| 6,670,427 B1 | 12/2003 | Ulbricht et al. | |
| 6,673,596 B1 | 1/2004 | Sayler et al. | |
| 6,720,402 B2 | 4/2004 | Langer et al. | |
| 6,733,471 B1 | 5/2004 | Ericson et al. | |
| 6,743,190 B2 | 6/2004 | Connelly et al. | |
| 6,755,621 B2 | 6/2004 | Lopez et al. | |
| 6,793,642 B2 | 9/2004 | Connelly et al. | |
| 6,796,956 B2 | 9/2004 | Hartlaub et al. | |
| 6,797,522 B1 | 9/2004 | Still et al. | |
| 6,808,522 B2 | 10/2004 | Richards et al. | |
| 6,849,183 B2 | 2/2005 | Gorsuch et al. | |
| 6,946,127 B2 | 9/2005 | Bitensky et al. | |
| 6,956,961 B2 | 10/2005 | Cong et al. | |
| 7,033,571 B2 | 4/2006 | Gutowska et al. | |
| 7,097,662 B2 | 8/2006 | Evans, III et al. | |
| 7,124,773 B2 | 10/2006 | Midtgård et al. | |
| 7,151,847 B2 | 12/2006 | Vaisberg et al. | |
| 7,244,232 B2 | 7/2007 | Connelly et al. | |
| 7,303,875 B1 | 12/2007 | Bock et al. | |
| 7,309,786 B2 | 12/2007 | Zhang et al. | |
| 7,319,038 B2 | 1/2008 | Southard | |
| 7,326,240 B1 | 2/2008 | Caro et al. | |
| 7,355,334 B2 | 4/2008 | Anazawa et al. | |
| 7,413,846 B2 | 8/2008 | Maloney et al. | |
| 7,415,359 B2 | 8/2008 | Hill et al. | |
| 7,476,210 B2 | 1/2009 | Gorsuch et al. | |
| 7,553,625 B2 | 6/2009 | Hoon et al. | |
| 7,892,766 B2 | 2/2011 | King et al. | |
| 8,000,784 B2 | 8/2011 | Ferren et al. | |
| 2002/0009759 A1 | 1/2002 | Terstappen et al. | |
| 2002/0034757 A1 | 3/2002 | Cubicciotti | |
| 2002/0164825 A1 | 11/2002 | Chen | |
| 2003/0231981 A1 | 12/2003 | Johnson et al. | |
| 2004/0018508 A1 | 1/2004 | Friedman | |
| 2004/0033584 A1 | 2/2004 | Lederberg | |
| 2004/0034317 A1 | 2/2004 | Gorsuch et al. | |
| 2004/0191246 A1 | 9/2004 | Connelly et al. | |
| 2004/0218724 A1 | 11/2004 | Chornenky et al. | |
| 2005/0121411 A1 | 6/2005 | Cohen | |
| 2005/0126916 A1 | 6/2005 | Lockard et al. | |
| 2005/0221529 A1 | 10/2005 | Bang et al. | |
| 2005/0251347 A1 | 11/2005 | Perona et al. | |
| 2005/0272974 A1 | 12/2005 | Iddan | |
| 2006/0039593 A1 | 2/2006 | Sammak et al. | |
| 2006/0083716 A1 | 4/2006 | Kaufman et al. | |
| 2006/0172318 A1 | 8/2006 | Medinz et al. | |
| 2006/0183223 A1 | 8/2006 | King et al. | |
| 2006/0234369 A1 | 10/2006 | Sih | |
| 2007/0010868 A1 | 1/2007 | Ferren et al. | |
| 2007/0021927 A1 | 1/2007 | Ishikawa et al. | |
| 2007/0066929 A1 | 3/2007 | Ferren et al. | |
| 2007/0066939 A1 | 3/2007 | Krulevitch et al. | |
| 2007/0083333 A1 | 4/2007 | Vitiello et al. | |
| 2007/0093739 A1 | 4/2007 | Brady et al. | |
| 2007/0156211 A1 | 7/2007 | Ferren et al. | |
| 2007/0178084 A1 | 8/2007 | King et al. | |
| 2007/0225633 A1 | 9/2007 | Ferren et al. | |
| 2007/0225634 A1 | 9/2007 | Ferren et al. | |
| 2007/0276208 A1 | 11/2007 | Connelly et al. | |
| 2007/0294150 A1 | 12/2007 | Jung et al. | |
| 2008/0058785 A1 | 3/2008 | Boyden et al. | |
| 2008/0201122 A1 | 8/2008 | Kelly et al. | |
| 2008/0241847 A1 | 10/2008 | Hoon et al. | |
| 2008/0275376 A1 | 11/2008 | Howell et al. | |
| 2008/0281400 A1 | 11/2008 | Philipp et al. | |
| 2008/0286278 A1 | 11/2008 | Connelly et al. | |
| 2009/0022768 A1 | 1/2009 | King et al. | |
| 2009/0054908 A1 | 2/2009 | Zand et al. | |
| 2009/0093728 A1 | 4/2009 | Hyde et al. | |
| 2009/0182127 A1 | 7/2009 | Kjaergaard et al. | |
| 2010/0167372 A1 | 7/2010 | King et al. | |
| 2010/0185134 A1 | 7/2010 | Houwen et al. | |

OTHER PUBLICATIONS

Alexander et al.; "Molecular imprinting science and technology: a survey of the literature for the years up to and including 2003"; Journal of Molecular Recognition; 2006; pp. 106-180; vol. 19; John Wiley & Sons, Ltd.

Ammor, Mohammed Salim; "Recent Advances in the Use of Intrinsic Fluorescence for Bacterial Identification and Characterization"; J Fluoresc; 2007; pp. 1-5; Springer-Science + Business Media LLC.

An, Gary; "Theoretical Biology and Medical Modelling"; 2008; pp. 1-20; vol. 5, No. 11; BioMed Central Ltd.

Anderson et al.; "Inactivation of Food-Borne Enteropathogenic Bacteria and Spoilage Fungi Using Pulsed-Light"; IEEE Transactions on Plasma Science; Feb. 2000; pp. 83-88; vol. 28, No. 1; IEEE.

Baker et al.; "An Electronic, Aptamer-Based Small-Molecule Sensor for the Rapid, Label-Free Detection of Cocaine in Adulterated Samples and Biological Fluids"; J. Am. Chem. Soc.; 2006; pp. 3138-3139; vol. 128, No. 10; American Chemical Society.

Becker et al.; "An antibody-interleukin 2 fusion protein overcomes tumor heterogeneity by induction of a cellular immune response"; Proc. Natl. Acad. Sci. USA; Jul. 1996; pp. 7826-7831; vol. 93.

Békássy, Zoltán; "Long-Term Follow-Up of Cervical Intraepithelial Neoplasia Treated with Minimal Conization by Carbon Dioxide Laser"; Lasers in Surgery and Medicine; 1997; pp. 461-466; vol. 20; Wiley-Liss, Inc.

Bellin et al.; Polymeric triple-shape materials; PNAS; Nov. 28, 2006; pp. 18043-18047; vol. 103, No. 48; The National Academy of Sciences of the USA.

Bezrouk et al.; "Temperature Characteristics of Nitinol Spiral Stents"; Scripta Medica (BRNO); Oct. 2005; pp. 219-226; vol. 78, No. 4.

Bins et al.; "Texture of White Blood Cells Expressed by the Counting Densitogram"; Cytometry; 1981; pp. 321-324; vol. 1, No. 5.

Bouchard et al.; "Optical characterization of *Pseudomonas fluorescens* on meat surfaces using time-resolved fluorescence"; Journal of Biomedical Optics; Jan./Feb. 2006; pp. 0140011-1-0140011-7; vol. 11, No. 1; Society of Photo-Optical Instrumentation Engineers.

Brennan, John D.; "Preparation and Entrapment of Fluorescently Labeled Proteins for the Development of Reagentless Optical Biosensors"; Journal of Fluorescence; 1999; pp. 295-312; vol. 9, No. 4; Plenum Publishing Corporation.

Bright et al.; "Regenerable Fiber-Optic-Based Immunosensor"; Anal. Chem.; 1990; pp. 1065-1069; vol. 62; American Chemical Society.

Cady et al.; "Optimized linkage and quenching strategies for quantum dot molecular beacons"; Molecular and Cellular Probes; 2007; pp. 116-124; vol. 21, Elsevier Ltd.

Camara et al.; "Seeding of epithelial cells into circulation during surgery for breast cancer: the fate of malignant and benign mobilized cells"; World Journal of Surgical Oncology; 2006; pp. 1-7; vol. 4, No. 67; BioMed Central Ltd.

Cao et al.; "Molecular Beacon Aptamers for Protein Monitoring in Real-Time and in Homogeneous Solutions"; Current Proteomics; 2005; pp. 31-40; vol. 2, No. 1; Bentham Science Publishers Ltd.

Chakravarty et al.; "Thermal ablation of tumor cells with antibody-functionalized single-walled carbon nanotubes"; PNAS; Jun. 24, 2008; pp. 8697-8702; vol. 105, No. 25; The National Academy of Sciences of the USA.

Challita-Eid et al.; "A B7.1-Antibody Fusion Protein Retains Antibody Specificity and Ability to Activate Via the T Cell Costimulatory Pathway"; The Journal of Immunology; 1998; pp. 3419-3426; vol. 160; The American Association of Immunologists.

Chan et al.; "Bactericidal effects of different laser wavelengths on periodontopathic germs in photodynamic therapy"; Lasers Med Sci; 2003; pp. 51-55, vol. 18; Springer-Verlag-London Limited.

Chen et al.; Aptamer from whole-bacterium SELEX as new therapeutic reagent against virulent *Mycobacterium tubercolosis*; Biochemical and Biophysical Research Communications; 2007; pp. 743-748; vol. 357; Elsevier Inc.

Chen et al.; "Ubiquitin-associated (UBA) domains in Rad23 bind ubiquitin and promote inhibition of multi-ubiquitin chain assembly"; EMBO reports; 2001; pp. 933-938; vol. 2, No. 101; European Molecular Biology Organization.

Chung et al.; Size Comparisons among Integral Membrane Transport Protein Homologues in *Bacteria, Archaea,* and *Eucarya*; Journal of Bacteriology; Feb. 2001; pp. 1012-1021; vol. 183, No. 3; American Society for Microbiology.

Colas et al.; "Targeted modiciation and transportation of cellular proteins"; PNAS; Dec. 5, 2000; pp. 13720-13725; vol. 97, No. 25.

Complete Blood Count (CBC); WebMD 7 pgs.; located at http://www.webmd.com/a-to-z-guides/complete-blood-count-cbc; accessed on Oct. 5, 2009.

Crawford et al.; "Peptide aptamers: Tools for biology and drug discovery"; Briefings in Functional Genomics and Proteomics; Apr. 2003; pp. 72-79; vol. 2, No. 1; Henry Stewart Publications.

Cristofanilli et al.; "Circulating Tumor Cells, Disease Progression, and Survival in Metastatic Breast Cancer"; The New England Journal of Medicine; Aug. 19, 2004; pp. 781-791; vol. 351, No. 8; Massachusetts Medical Society.

Davies, Michael J.; "Singlet oxygen-mediated damage to proteins and its consequences"; Biochemical and Biophysical Research Communications; 2003; pp. 761-770; vol. 305; Elsevier Science (USA).

Dehio, Christoph; Cellular Microbiology; 2008; pp. 1591-1598; vol. 10, No. 8; Blackwell Publishing Ltd.

Dempster et al.; "Using Granulometries in Processing Images of Malarial Blood"; 2001; pp. V-291-V-294; IEEE.

Desimone et al.; "Bactericidal Effect of 0.95-mW Helium-Neon and 5-mW Indium-Gallium-Aluminum-Phospate Laser Irradiation at Exposure Times of 30, 60, and 120 Seconds on Photosensitized *Staphylococcus aureus* and *Pseudomonas aeruginosa* in Vitro"; Physical Therapy; Sep. 1999; pp. 839-846; vol. 79, No. 9; American Physical Therapy Association.

Doornbos et al.; "White Blood Cell Differentiation Using a Solid State Flow Cytometer"; Cytometry; 1993; pp. 589-594; vol. 14; Wiley-Liss, Inc.

Durick et al.; "Cellular biosensors for drug discovery"; Biosensors & Bioelectronics; 2001; pp. 587-592; vol. 16; Elsevier Science B.V.

Fan et al.; "Sensitive optical biosensors for unlabeled targets: A review"; Analytica Chimica Acta; 2008; pp. 8-26; vol. 620; Elsevier B.V.

Fan et al.; "Structures in *Bacillus subtilis* Are Recognized by CD14 in a Lipopolysaccharide Binding Protein-Dependent Reaction"; Infection and Immunity; Jun. 1999; pp. 2964-2968; vol. 67, No. 6; American Society for Microbiology.

Fei-Fei et al.; "One-Shot Learning of Object Categories"; IEEE Transactions on Pattern Analysis and Machine Intelligence; Apr. 2006; pp. 594-611; vol. 28, No. 4; IEEE Computer Society.

Fizazi et al.; "High detection rate of circulating tumor cells in blood of patients with prostate cancer using telomerase activity"; Annals of Oncology; 2007; pp. 518-521; vol. 18, No. 3; European Society for Medical Oncology.

Flatmark et al.; "Immunomagnetic Detection of Micrometastatic Cells in Bone Marrow of Colorectal Cancer Patients"; Clinical Cancer Research; Feb. 2002; pp. 444-449; vol. 8.

Francisco et al.; "Production and fluorescence-activated cell sorting of *Escherichia coli* expressing a functional antibody fragment on the external surface"; Proc. Natl. Acad. Sci. USA; Nov. 1993; pp. 10444-10448; vol. 90.

Gao et al.; "A Micro Sensing Probe for Detecting Individual Biological Cells"; Proceedings of the $25^{th}$ Annual International Conference of the IEEE EMBS; Cancun, Mexico; Sep. 17-21, 2003; pp. 3348-3351.

Gao et al.; "Two-state selection of conformation-specific antibodies"; PNAS; Mar. 3, 2009; pp. 3071-3076; vol. 106, No. 9; The National Academy of Sciences of the USA.

Gibson et al.; "Ten-year experience of carbon dioxide laser ablation as treatment for cutaneous recurrence of malignant melanoma"; British Journal of Surgery; 2004; pp. 893-895; vol. 91; John Wiley & Sons Ltd.

Givrad et al.; "Implantable Minipump with MEMS Electrothermal Valve for Bolus Injection in Mice"; Proceedings of BIOMed2008; $3^{rd}$ Frontiers in Biomedical Devices Conference; Jun. 18-20, 2008, Irvine, California, USA; pp. 1-2; ASME.

Grayson et al.; "A BioMEMS Review: MEMS Technology for Physiologically Integrated Devices"; Proceedings of the IEEE; Jan. 2004; pp. 6-21; vol. 92, No. 1; IEEE.

Green, Christopher F.; "Disinfection of selected *Aspergillus* spp. using ultraviolet germicidal irradiation"; Can. J. Microbiol; 2004; pp. 221-224; vol. 50; NRC Canada.

Grönqvist et al; "Bactericidal Effect of Pulsed 1,064 nm Nd:YAG Laser Light on *Staphylococcus epidermidis* Is of Photothermal Origin: An in Vitro Study"; Lasers in Surgery and Medicine; 2000; pp. 336-340; vol. 27; Wiley-Liss, Inc.

Guffey et al.; "Effects of Combined 405-nm and 880-nm Light on *Staphylococcus aureus* and *Pseudomonas aeruginosa* in Vitro"; Photomedicine and Laser Surgery; 2006; pp. 680-683; vol. 24, No. 6; Mary Ann Liebert, Inc.

Guthrie et al.; "Assays for cytokines using aptamers"; Methods; 2006; pp. 324-330; vol. 38; Elsevier Inc.

Hamblin et al.; "Rapid Control of Wound Infections by Targeted Photodynamic Therapy Monitored by in Vivo Bioluminescence Imaging"; Photochemistry and Photobiology; 2002; pp. 51-57; vol. 75, No. 1.

Hancock et al.; "Megawatt, Pulsed Ultraviolet Photon Sources for Microbial Inactivation"; IEEE Transactions on Plasma Science; Oct. 2004; pp. 2026-2031; vol. 32, No. 5; IEEE.

Hanna et al.; "Using a System-on-a-Chip Implantable Device to Filter Circulating Infected Cells in Blood or Lymph"; IEEE Transactions on Nanobioscience; Mar. 2003; pp. 6-13; vol. 2, No. 1; IEEE.

Hansen et al.; "Transbronchial laser ablation of benign and malignant tumors"; Minimally Invasive Therapy; 2006; pp. 4-8; vol. 15, No. 1; Taylor & Francis.

Heath et al.; "Antibody-targeted liposomes: Increase in specific toxicity of methotrexate-γ-aspartate"; Proc. Natl. Acad. Sci. USA; Mar. 1983; pp. 1377-1381; vol. 80.

He et al.; "In vivo quantitation of rare circulating tumor cells by multiphoton intravital flow cytometry"; PNAS; Jul. 10, 2007; pp. 11760-11765; vol. 104, No. 28; The National Academy of Sciences of the USA.

Ho et al.; "Isolation of anti-CD22 with high affinity by Fv display on human cells"; PNAS; Jun. 20, 2006; pp. 9637-9642; vol. 103, No. 25.

Horata et al.; "Sequence variation of PfEMPI-DBLα in association with rosette formation in *Plasmodium facliparum* isolates causing severe and uncomplicated malaria"; Malaria Journal; 2009; pp. 1-11; vol. 8, No. 184; BioMed Central Ltd.

Horne et al.; "Which White Blood Cell Subtypes Predict Increased Cardiovascular Risk?"; Journal of the American College of Cardiology; 2005; pp. 1638-1643; vol. 45, No. 10; Elsevier Inc.

Hou et al.; "Disintegration of Biomacromolecules by Dielectric Barrier Discharge Plasma in Helium at Atmospheric Pressure"; IEEE Transactions on Plasma Science; Aug. 2008; pp. 1633-1637; vol. 36, No. 4; IEEE.

Hu et al.; "A Chimeric Lym-1/Interleukin 2 Fusion Protein for Increasing Tumor Vascular Permeability and Enhancing Antibody Uptake"; Cancer Research; Nov. 1, 1996; pp. 4998-5004; vol. 56.

Hu et al.; "Preparation of a biochip on porous silicon and application for label-free detection of small molecule-protein interactions"; Rapid Communications in Mass Spectrometry; 2007; pp. 1277-1281; vol. 21; John Wiley & Sons, Ltd.

Jaiswal et al.; "Long-term multiple color imaging of live cells using quantum dot bioconjugates"; Nature Biotechnology; Jan. 2003; pp. 47-51; vol. 21; Nature Publishing Group.

Janda et al.; "Induction of an Antibody That Catalyzes the Hydrolysis of an Amide Bond"; Science; Sep. 2, 1988; pp. 1188-1191; vol. 241.

Jawhara et al.; "Monitoring of bactericidal action of laser by in vivo imaging of bioluminescent *E. coli* in a cutaneous wound infection"; Lasers Med Sci; 2006; pp. 153-159; vol. 21; Springer-Verlag London Limited.

Jayasena, Sumedha D.; "Aptamers: An Emerging Class of Molecules That Rival Antibodies in Diagnostics"; Clinical Chemistry; 1999; pp. 1628-1650; vol. 45, No. 9; American Association for Clinical Chemistry.

Jhaveri et al.; "In vitro selection of signaling aptamers"; Nature Biotechnology; Dec. 2000; pp. 1293-1297; vol. 18; Nature America Inc.

Johnson et al.; "Design and Testing of an Impedance-Based Sensor for Monitoring Drug Delivery"; Journal of the Electrochemical Society; 2005; pp. H6-H11; vol. 152, No. 1; The Electrochemical Society.

Jori et al.; "Photodynamic Therapy in the Treatment of Microbial Infections: Basic Principles and Perspective Applications"; Lasers in Surgery and Medicine; 2006; pp. 468-481; vol. 38; Wiley-Liss, Inc.

Kam et al.; "Carbon nanotubes as multifunctional biological transporters and near-infrared agents for selective cancer cell destruction"; PNAS; Aug. 16, 2005; pp. 11600-11605; vol. 102, No. 33; The National Academy of Sciences of the USA.

Karrer et al.; "Photodynamic Inactivation of *Staphylococci* with 5-Aminolaevulinic Acid or Photofrin"; Lasers Med Sci; 1999; pp. 54-61; vol. 14; Springer-Verlag London Limited.

Katial et al.; "Deleterious effects of electron beam radiation on allergen extracts"; J Allergy Clin Immunol; Aug. 2002; pp. 215-219; vol. 110, No. 2.

Katsumata et al.; "Detection and evaluation of epithelial cells in the blood of colon cancer patients using RT-PCR"; Int J Clin Oncol; 2006; pp. 385-389; vol. 11; Abstract; 1 pg.; The Japan Society of Clinical Oncology.

Keefe et al.; "Photodynamic Therapy of High-Grade Cervical Intraepithelial Neoplasia With 5-Aminolevulinic Acid"; Lasers in Surgery and Medicine; 2002; pp. 289-293; vol. 31; Wiley-Liss, Inc.

Kellum et al.; "Understanding the Inflammatory Cytokine Response in Pneumonia and Sepsis"; Arch Intern Med; Aug. 13-27, 2007; pp. 1655-1663; vol. 167, No. 15; American Medical Association.

Kennedy et al.; "High intensity focused ultrasound: surgery of the future?"; The British Journal of Radiology; Sep. 2003; pp. 590-599; vol. 76; The British Institute of Radiology.

Kim et al.; "Real-Time Detection of Microbial Contamination"; IEEE Engineering in Medicine and Biology Magazine; Jan./Feb. 2004; pp. 122-129; IEEE.

Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.

Koenig et al.; "Laser-Induced Autofluorescence for Medical Diagnosis"; Journal of Fluorescence; 1994; pp. 17-40; vol. 4, No. 1; Plenum Publishing Corporation.

Koo et al.; "Development of a Streptavidin-Conjugated Single-Chain Antibody That Binds *Bacillus cereus* Spores"; Applied and Environmental Microbiology; Jul. 1998; pp. 2497-2502; vol. 64, No. 7; American Society for Microbiology.

Kufer et al.; "A revival of bispecific antibodies"; Trends in Biotechnology; May 2004; pp. 238-244; vol. 22, No. 5; Elsevier Ltd.

Kupper et al.; "Generation of human antibody fragments against *Streptococcus mutans* using a phage display chain shuffling approach"; BMC Biotechnology; 2005; pp. 1-12; vol. 5, No. 4; BioMed Central Ltd.

Kurt et al.; Serum IL-1β, IL-6, IL-8, and TNF-α Levels in Early Diagnosis and Management of Neonatal Sepsis; Mediators of Inflammation; pp. 1-5; vol. 2007; Article ID 31397; Hindawi Publishing Corporation.

Lacroix-Desmazes et al.; "Catalytic IgG from Patients with Hemophilia A Inactivate Therapeutic Factor VIII"; The Journal of Immunology; 2006; pp. 1355-1363; vol. 177; The American Association of Immunologists, Inc.

Lee et al.; "Laser-Generated Stress Waves and Their Effects on the Cell Membrane"; IEEE Journal of Selected Topics in Quantum Electronics; Jul./Aug. 1999; pp. 997-1003; vol. 5, No. 4; IEEE.

Lee et al.; "Performance of an Immobilized Trypsin System for Improving Oxidative Stability of Milk"; Journal of Dairy Science; 1974; pp. 473-476; vol. 58, No. 4.

Lee et al.; "A strategy for predicting the chemosensitivity of human cancers and its application to drug discovery"; PNAS; Aug. 7, 2007; pp. 13086-13091; vol. 104, No. 32; The National Academy of Sciences of the USA.

Li et al.; "A Patient-Specific in silico Model of Inflammation and Healing Tested in Acute Vocal Fold Injury"; PLoS ONE; Jul. 2008; pp. 1-11; vol. 3, No. 7.

Lill et al.; "Microwave-Assisted Proteomics"; Mass Spectrometry Reviews; 2007; pp. 657-671; vol. 26; Wiley Periodicals, Inc.

López-Ferrer et al.; "Rapid Sample Processing for LC-MS-Based Quantative Proteomics Using High Intensity Focused Ultrasound"; Journal of Proteome Research; 2008; pp. 3860-3867; vol. 7, No. 9; American Chemical Society.

Luckevich, Mark; "MEMS microvalves: the new valve world"; Valve World; May 2007; pp. 79-83; www.valve-world.net.

Ma et al.; "Potent Antitumor Activitiy of an Auristation-Conjugated, Fully Human Monoclonal Antibody to Prostate-Specific Membrane Antigen"; Clin Cancer Res; Apr. 15, 2006; pp. 2591-2596; vol. 12, No. 8; American Association for Cancer Research.

Mahmud et al.; "Directing cell motions on micropatterened ratchets"; Nature Physics; 2009; pp. 606-612; vol. 5; Article Abstract; 2 pgs.

Maisch, Tim; "Anti-microbial photodynamic therapy: useful in the future?"; Lasers Med Sci; 2007; pp. 83-91; vol. 22; Springer-Verlag London Limited.

Malek et al.; "Identification and initial characterization of a rat monoclonal antibody reactive with the murine interleukin 2 receptor-ligand complex"; Proc. Natl. Acad. Sci USA; Sep. 1983; pp. 5694-5698; vol. 80.

Maloney et al.; "Implantable Microchips for Controlled Drug Delivery"; Proceedings of the 26th Annual International Conference of the IEEE EMBS; San Francisco, CA USA; Sep. 1-5, 2004; pp. 2668-2669; IEEE.

Martin et al.; "Learning to Detect Natural Image Boundaries Using Local Brightness, Color, and Texture Cues"; IEEE Transactions on Pattern Analysis and Machine Intelligence; May 2004; pp. 530-549; vol. 26, No. 5; IEEE Computer Society.

Mateus et al.; "Adherence of *Candida albicans* to Silicone Induces Immediate Enhanced Tolerance to Fluconazole"; Antimicrobial Agents and Chemotherapy; Sep. 2004; pp. 3358-3366; vol. 48, No. 9; American Society for Microbiology.

May, Mike; "Detection of Circulating Epithelial Cells"; Bioscience Technology; Jul. 2008; 3 pgs.; located at www.BioscienceTechnology.com.

McDevitt et al.; "Tumor Targeting with Antibody-Functionalized, Radiolabeled Carbon Nanotubes" The Journal of Nuclear Medicine; Jul. 2007; pp. 1180-1189; vol. 48, No. 7; Society of Nuclear Medicine, Inc.

Mendelow et al.; "Automated malaria detection by depolarization of laser light"; British Journal of Haematology; 1999; pp. 499-503; vol. 104; Blackwell Science Ltd.

Miller et al.; "Cancer Cells Ablation with Irreversible Electroporation"; Technology in Cancer Research & Treatment; Dec. 2005; pp. 1-7; vol. 4, No. 6; Adenine Press.

Miller et al.; "Photodynamic Therapy with the Phthalocyanine Photosensitizer Pc 4: The Case Experience with Preclinical Mechanistic and Early Clinical-Translational Studies"; Toxicol Appl Pharmacol; Nov. 1, 2007; pp. 290-299; vol. 244, No. 3.
Mittal et al.; "IL-10 in Early Rheumatoid Arthritis"; J Indian Rhematoid Assoc; 2002; pp. 59-60; vol. 10.
Miyata et al.; Tumor marker-responsive behavior of gels prepared by biomolecular imprinting; PNAS; Jan. 31, 2006; pp. 1190-1193; vol. 103, No. 5; The National Academy of Sciences of the USA.
MMWR Weekly; Adult Blood Lead Epidemiology and Surveillance—United States, 2005-2007; Apr. 17, 2009; pp. 365-369; vol. 58, No. 14 (4 actual pgs. Attached).
Mohamed et al.; "Development of a Rare Cell Fractionation Device: Application for Cancer Detection"; IEEE Transactions on Nanobioscience; Dec. 2004; pp. 251-256; vol. 3, No. 4; IEEE.
Moore et al.; "The Comparative Size and Structure of Tumor Cells and Clumps in the Blood, Bone Marrow, and Tumor Imprints"; Cancer; Jan.-Feb. 1960; pp. 111-117; vol. 13, No. 1.
Nakada et al.; "Blood Purification for hypercytokinemia"; Transfusion and Apheresis Science; 2006; pp. 253-264; vol. 35; Elsevier Ltd.
Narasipura et al.; "Purification of CD45+ hemtopoietic cells directly from human bone marrow using a flow-based P-selectin-coated microtube"; Am. J. Hematol.; 2008; pp. 627-629; vol. 83; Wiley-Liss, Inc.
National Cancer Institute FactSheet; Lasers in Cancer Treatment: Questions and Answers; Aug. 10, 2004; pp. 1-4.
Nemazee et al.; "Enhancing antibody: A novel component of the immune response"; Proc. Natl Acad. Sci. USA; Jun. 1982; pp. 3828-3832; vol. 79.
Nitin et al.; "Peptide-linked molecular beacons for efficient delivery and rapid mRNA detection in living cells"; Nucleic Acids Research; 2004; pp. 1-8; vol. 32, No. 6; Oxford University Press.
Nitzan et al.; "Endogenous Porphyrin Production in Bacteria by δ-Aminolaevulinic Acid and Subsequent Bacterial Photoeradication"; Lasers Med Sci; 1999; pp. 269-277; vol. 14; Springer-Verlag London Limited.
Norberto et al.; "Laser photoablation of colorectal adenomas"; Surg Endosc; 2005; pp. 1045-1048; vol. 19; Springer Science+Business Media, Inc.
Noronha et al.; "Hyperactivated B cells in human inflammatory bowel disease"; Journal of Leukocyte Biology; Oct. 2009; pp. 1-10; vol. 86; Society for Leukocyte Biology.
Nowlan et al.; "Systemic cytokine levels and the effects of etanercept in TNF receptor-associated periodic syndrome (TRAPS) involving a C33Y mutation in TNFRSF1A"; Rheumatology; 2006; pp. 31-37; vol. 45; Oxford University Press on behalf of the British Society for Rheumatology.
Nussbaum et al.; "Effects of 810 nm Laser Irradiation on in Vitro Growth of Bacteria: Comparison of Continuous Wave and Frequency Modulated Light"; Lasers in Surgery and Medicine; 2002; pp. 343-351; vol. 31; Wiley-Liss, Inc.
Nyitrai et al.; "Preparing Stents with Masking & Etching Technology"; 26th International Spring Seminar on Electronics Technology; May 8-11, 2003; Stará Lesná, Slovak Republic; pp. 321-324; IEEE.
Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52; IUMS.
Olafsen et al.; "Covalent disulfide-linked anti-CEA diabody allows site-specific conjugation and radiolabeling for tumor targeting applications"; Protein Engineering, Design & Selection; 2004; pp. 21-27; vol. 17, No. 1; Oxford University Press.
Olson et al.; "Classification of cultured mammalian cells by shape analysis and pattern recognition"; Proc. Natl. Acad. Sci. USA; Mar. 1980; pp. 1516-1520; vol. 77, No. 3.
Ozaki et al.; "Cytokine and Cytokine Receptor Pleiotropy and Redundancy"; The Journal of Biological Chemistry; Aug. 16, 2002; pp. 29355-29358; vol. 277, No. 33.
Pachmann et al.; "Quantification of the response of circulating epithelial cells to neodadjuvant treatment for breast cancer: a new tool for therapy monitoring"; Breast Cancer Research; 2005; pp. R975-R979; vol. 7, No. 6; BioMed Central Ltd.
Patel et al.; "Medical Toxicology and Public Health-Update on Research and Activities at the Centers for Disease Control and Prevention and the Agency for Toxic Substances and Disease Registry"; Journal of Medical Toxicology; Jun. 2006; pp. 83-84; vol. 2, No. 2.
Peppas et al.; "Polymers and Gels as Molecular Recognition Agents"; Pharmaceutical Research; May 2002; pp. 578-587; vol. 19, No. 5; Plenum Publishing Corporation.
Pervan et al.; "Proteasome Structures Affected by Ionizing Radiation"; Mol Cancer Res; Jul. 2005; pp. 381-390; vol. 3, No. 7; American Association for Cancer Research.
Ponomarenko et al.; "Autoantibodies to myelin basic protein catalyze site-specific degradation of their antigen"; PNAS; Jan. 10, 2006; pp. 281-286; vol. 103, No. 2; The National Academy of Sciences of the USA.
Prescott et al.; "Chronic, programmed polypeptide delivery from an implanted, multireservoir microchip device"; Nature Biotechnology; Apr. 2006; pp. 437-438; vol. 24, No. 4; Nature Publishing Group.
Presterl et al.; "Cytokine Profile and Correlation to the Apache III and MPM II Scores in Patients with Sepsis"; Am J Respir Crit Care Med; 1997; pp. 825-832; vol. 156.
Proske et al.; "Aptamers-basic research, drug development, and clinical applications"; Appl Microbiol Biotechnol; 2005; pp. 367-374; vol. 69; Springer-Verlag 2005.
Raghavan et al.; "BIAcore: a microchip-based system for analyzing the formation of macromolecular complexes"; Structure; Apr. 15, 1995; pp. 331-333; vol. 3; Current Biology Ltd.
Rana et al.; "Delivery of apoptotic signal to rolling cancer cells: a novel biomimetic technique using immobilized TRAIL and E-selectin"; Biotechnol Bioeng.; Apr. 15, 2009; pp. 1692-1702; vol. 102, No. 6; Abstract, 1 pg.
Rolle et al.; "Increase in number of circulating disseminated epithelial cells after surgery for non-small cell lung cancer monitored by MAINTRAC® is a predictor for relapse: A preliminary report"; World Journal of Surgical Oncology; 2005; pp. 1-9; vol. 3; No. 18; BioMed Central Ltd.
Ross, Gillian; "Accelerated partial breast irradiation: technology feasible but who will benefit?"; Breast Cancer Research; May 2005; pp. 110-112; vol. 7, No. 3; BioMed Central Ltd.
Rossetti et al.; "Immobilization and Detection of Functionalized Nanocontainers on (Patterned) Surfaces"; European Cells and Materials; 2003; p. 83; vol. 6, Suppl. 1.
Roufosse, Florence; "Hypereosinophilic syndrome variants: diagnostic and therapeutic considerations"; haematologica; 2009; pp. 1188-1193; vol. 94, No. 9.
Samia et al.; "Quantum Dot-based Energy Transfer: Perspectives and Potential for Applications in Photodynamic Therapy"; Photochemistry and Photobiology; 2006; pp. 617-625; vol. 82; American Society for Photobiology.
Schuster et al.; "Circulating Tumor Cells as Prognostic Factor for Distant Metastases and Survival in Patients with Primary Uveal Melanoma"; Clin Cancer Res; Feb. 15, 2007; pp. 1171-1178; vol. 13, No. 4; American Association for Cancer Research.
Serebrovskaya et al.; "Targeting cancer cells by using an antireceptor antibody-photosensitizer fusion protein"; PNAS; Jun. 9, 2009; pp. 9221-9225; vol. 106, No. 23.
Shangguan et al.; "Aptamers evolved from live cells as effective molecular probes for cancer study"; PNAS; Aug. 8, 2006; pp. 11838-11843; vol. 103, No. 32; The National Academy of Sciences of the USA.
Soria et al.; "Molecular Detection of Telomerase-positive Circulating Epithelial Cells in Metastatic Breast Cancer Patients"; Clinical Cancer Research; May 1999; pp. 971-975; vol. 5.
Spear et al.; "Isolation, characterization, and recovery of small peptide phage display epitopes selected against viable malignant glioma cells"; Cancer Gene Therapy; 2001; pp. 506-511; vol. 8, No. 7; Nature Publishing Group.
Stojanovic et al.; "Aptamer-Based Folding Fluorescent Sensor for Cocaine"; J. Am. Chem. Soc.; 2001; pp. 4928-4931; vol. 123, No. 21; American Chemical Society.
Stork et al.; "A novel tri-functional antibody fusion protein with improved pharmacokinetic properties generated by fusing a bispecific single-chain diabody with an albumin-binding domain from streptococcal protein G"; Protein Engineering, Design & Selection; 2007; pp. 569-576; vol. 20, No. 11; Oxford University Press.

Stubbe et al.; "'Programmed Polymeric Devices' for Pulsed Drug Delivery"; Pharmaceutical Research; Oct. 2004; pp. 1732-1740; vol. 21, No. 10; Springer Science+Business Media, Inc.

Szodoray et al.; "Programmed Cell Death in Rheumatoid Arthritis Peripheral Blood T-Cell Subpopulations Determined by Laser Scanning Cytometry"; Laboratory Investigation; 2003; pp. 1839-1848; vol. 83, No. 12; The United States and Canadian Academy of Pathology, Inc.

Takemura et al.; "Construction of a diabody (small recombinant bispecific antibody) using a refolding system"; Protein Engineering; 2000; pp. 583-588; vol. 13, No. 8; Oxford University Press.

Tsen et al.; "Inactivation of viruses by coherent excitations with a low power visible femtosecond laser"; Virology Journal; 2007; pp. 1-6; vol. 4, No. 50; BioMed Central Ltd.

Tseng et al.; "Inactivation of Viruses on Surfaces by Ultraviolet Germicidal Irradiation"; Journal of Occupational and Environmental Hygiene; Jun. 2007; pp. 400-405; vol. 4; No. 6; Joeh, LLC.

Ueda et al.; "Increased Plasma Levels of Adrenomedullin in Patients with Systemtic Inflammatory Response Syndrome"; Am J Respir Crit Care Med; 1999; pp. 132-136; vol. 160.

Ulrich et al.; "In Vitro Selection of RNA Aptamers That Bind to Cell Adhesion Receptors of *Trypanosoma cruzi* and Inhibit Cell Invasion"; The Journal of Biological Chemistry; Jun. 7, 2002; pp. 20756-20762; vol. 277, No. 23; The American Society for Biochemistry and Molecular Biology, Inc.

Vashist, Sandeep Kumar; "A Review of Microcantilevers for Sensing Applications"; Journal of Nanotechnology Online; Jun. 2007; pp. 1-15; vol. 3.

Vodovotz et al.; "Mathematical models of the acute inflammatory response"; Current Opinion in Critical Care; 2004; pp. 383-390; vol. 10; Lippincott Williams & Wilkins.

Vodovotz et al.; "Translational Systems Biology of Inflammation"; PLoS Computational Biology; Apr. 2008; pp. 1-6; vol. 4, No. 4.

Vučković et al.; "Gamma-radiation induced damage of proteins in the thick fraction of egg white"; J. Serb. Chem. Soc.; 2005; pp. 1255-1262; vol. 70, No. 11.

Walsh et al.; "Atmospheric Dielectric-Barrier Discharges Scalable From I mm to 1 m"; IEEE Transactions on Plasma Science; Aug. 2008; vol. 36, No. 4; IEEE.

Wang et al.; "Time course of plasma gelsolin concentrations during severe sepsis in critically ill surgical patients"; Critical Care; 2008; pp. 1-6; vol. 12, No. 4; BioMed Central Ltd.

Weatherall et al.; "Malaria and the Red Cell"; Hematology; 2002; pp. 35-57; American Society of Hematology.

Wentworth et al.; "Antibodies have the intrinsic capacity to destroy antigens"; PNAS; Sep. 26, 2000; pp. 10930-10935; vol. 97, No. 20.

Wentworth, Jr. et al.; "Antibody Catalysis of the Oxidation of Water"; Science; Sep. 7, 2001; pp. 1806-1811; vol. 293.

Wentworth, Jr., Paul; "Antibody Design by Man and Nature"; Science; Jun. 21, 2002; pp. 2247-2249; vol. 296.

Win et al.; "Codeine-binding RNA aptamers and rapid determination of their binding constants using a direct coupling surface plasmon resonance assay"; Nucleic Acids Research; 2006; pp. 5670-5682; vol. 34, No. 19.

Wojciechowski et al.; "Capture and enrichment of CD34-positive haematopoietic stem and progenitor cells from blood circulation using P-selectin in an implantable device"; British Journal of Haematology; 2008; pp. 673-681; vol. 140, No. 6; Blackwell Publishing Ltd.

Yang et al.; "On-Chip Electrochemical Impedance Spectroscopy for Biosensor Arrays"; IEEE Sensors; 2006; EXCO, Daegu, Korea; Oct. 22-25, 2006; pp. 93-96; IEEE.

Yang et al.; "Engineering Target-Responsive Hydrogels Based on Aptamer—Target Interactions"; J. Am. Chem. Soc.; 2008; pp. 6320-6321; vol. 130; No. 20; American Chemical Society.

Ye et al.; "Molecularly imprinted polymers as antibody and receptor mimics for assays, sensors and drug discovery"; Anal. Bioanal Chem; 2004; pp. 1887-1897; vol. 378; Springer-Verlag.

Zenker et al.; "From Inverse Problems in Mathematical Physiology to Quantitative Differential Diagnoses"; PLoS Computational Biology; Nov. 2007; pp. 2072-2086; vol. 3, No. 11.

Zharov et al.; "In vivo high-speed imaging of individual cells in fast blood flow"; Journal of Biomedical Optics; Sep./Oct. 2006; pp. 054034-1-054034-4; vol. 11, No. 5; SPIE.

Zharov et al.; "In Vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zhou et al.; Predicting short-term disease progression among HIV-infected patients in Asia and the Pacific region: preliminary results from the Treat Asia HIV Observational Database (TAHOD); HIV Medicine; 2005; pp. 216-223; vol. 6; British HIV Association.

Arndt et al.; "Microwave Radiation-Therapeutic Application for Cure of Subcutaneous Bacterial Infections"; Space Life Science; 2005; 2 pgs.; NASA Biennial Research and Technology Report. National Aeronautics and Space Administration, Houston, TX.

Baddour et al.; "High Frequency Ultrasound Imaging of Changes in Cell Structure Including Apoptosis"; created on Oct. 7, 2002; 6 pgs.

Bartels et al.; "Use of diode laser energy (808 nm) for selective photothermolysis of contaminated wounds"; Proc. SPIE; 1995; pp. 602-606; vol. 2395; located at http://dx.doi.org/10.1117/12.209149.

Renneisen et al; "Inhibition of Expression of Human Immunodeficiency Virus-1 in Vitro by Antibody-targeted Liposomes Containing Antisense RNA to the *env* Region"; The Journal of Biological Biochemistry; Sep. 25, 1990; pp. 16337-16342; vol. 265, No. 27; The American Society for Biochemistry and Molecular Biology, Inc.

Sapi et al.; "Detection of telomerase-positive circulating epithelial cells in ovarian cancer patients"; Cancer Detection and Prevention; May 2002; pp. 158-167; vol. 26, No. 2; Abstract; 1 pg.; Elsevier B.V.

Schneider et al.; "Automated Image Processing System for Shape Recognition of Single Red Blood Cells Based on Out-of-Focus Images"; Biorheology, Mar. 1995; pp. 237-238; vol. 32, No. 2; Elsevier.

Yeo et al.; "Bactericidal effects of high-power Nd:YAG laser radiation on *Staphylococcus aureus*"; Pure Appl. Opt.; Received for publication Jan. 9, 1998; pp. 643-655; vol. 7; IOP Publishing Ltd.

Yokota et al.; "Micro-Machined Stent-Type Flow Sensor For Evaluation of Nasal Respiration"; Micro Electro Mechanical Systems; Jan. 25-29, 2009; MEMS 2009; IEEE 22$^{nd}$ International Conference; pp. 495-498; IEEE.

\* cited by examiner $x_1, x_2, x_3, x_4 \ldots$ = concentrations of target component $X$ $y_1, y_2, y_3, y_4 \ldots$ = concentrations of target component $Y$ $\sigma_1, \sigma_2, \sigma_3 \ldots$ = standard deviation $$f = \frac{(x_1-y_1)^2}{(\sigma_1)^2} + \frac{(x_2-y_2)^2}{(\sigma_2)^2} + \frac{(x_3-y_3)^2}{(\sigma_3)^2} + \ldots$$

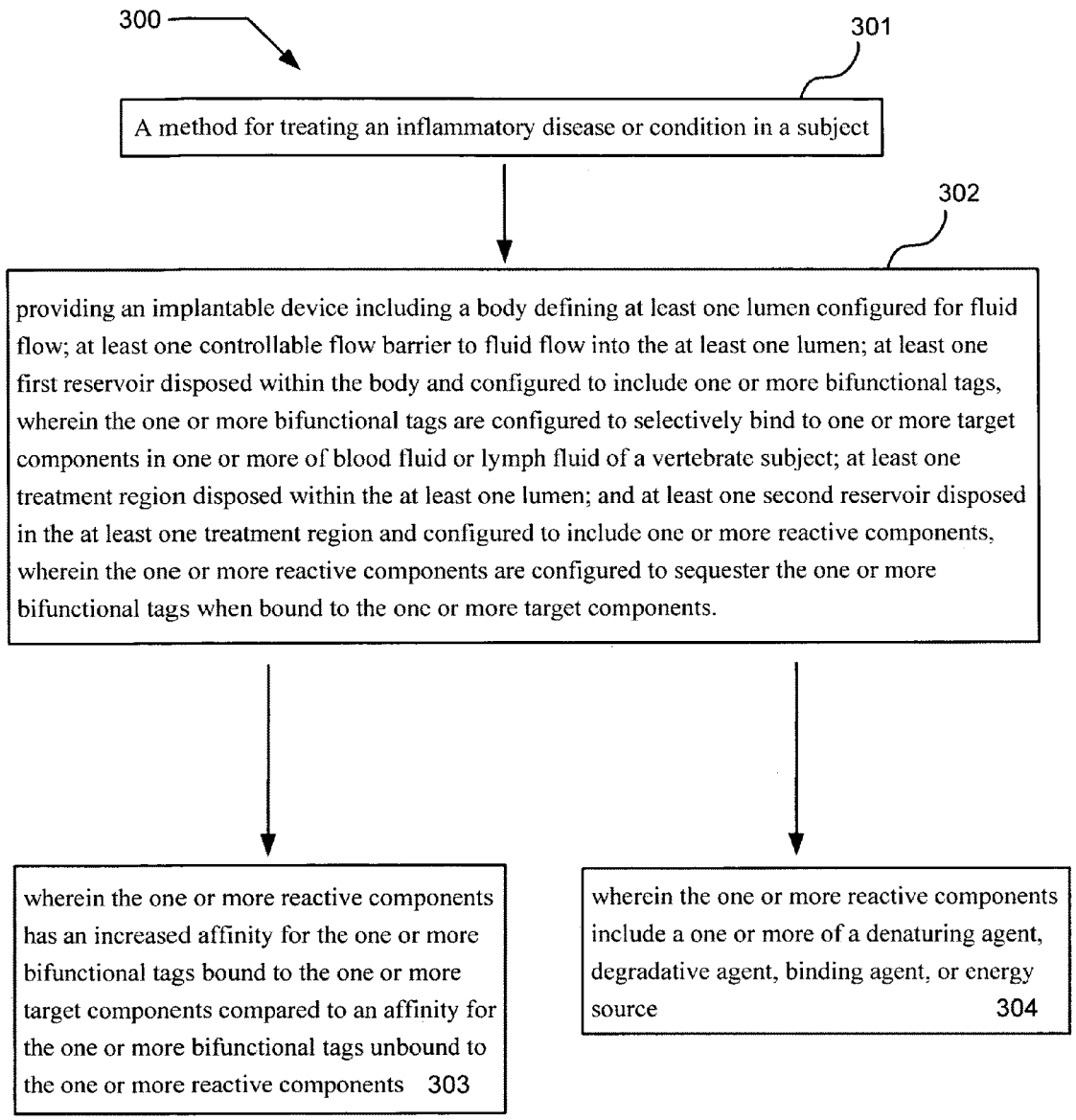

DEVICE FOR PASSIVELY REMOVING A TARGET COMPONENT FROM BLOOD OR LYMPH OF A VERTEBRATE SUBJECT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/660,928, entitled DEVICE FOR ACTIVELY REMOVING A TARGET CELL FROM BLOOD OR LYMPH OF A VERTEBRATE SUBJECT, naming RODERICK A. HYDE, MURIEL Y. ISHIKAWA, EDWARD K.Y. JUNG, ROBERT LANGER, ERIC C. LEUTHARDT, NATHAN P. MYHRVOLD, ELIZABETH A. SWEENEY, AND LOWELL L. WOOD, JR. as inventors, filed 05 Mar. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,400, entitled DEVICE, SYSTEM, AND METHOD FOR CONTROLLABLY REDUCING INFLAMMATORY MEDIATORS IN A SUBJECT, naming RODERICK A. HYDE, MURIEL Y. ISHIKAWA, EDWARD K. Y. JUNG, ROBERT LANGER, ERIC C. LEUTHARDT, NATHAN P. MYHRVOLD, ELIZABETH A. SWEENEY, AND LOWELL L. WOOD, JR. as inventors, filed 25 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,399, entitled DEVICE, SYSTEM, AND METHOD FOR CONTROLLABLY REDUCING INFLAMMATORY MEDIATORS IN A SUBJECT, naming RODERICK A. HYDE, MURIEL Y. ISHIKAWA, EDWARD K. Y. JUNG, ROBERT LANGER, ERIC C. LEUTHARDT, NATHAN P. MYHRVOLD, ELIZABETH A. SWEENEY, AND LOWELL L. WOOD, JR. as inventors, filed 25 Feb. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

Devices, systems, and methods are disclosed herein for controlling or modulating the levels of one or more target components in the blood fluid and/or lymph fluid of a vertebrate subject. The implantable device or system can include a body defining at least one lumen configured for fluid flow. The device or system can further include at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject, and at least one treatment region disposed within the at least one lumen. The device or system can further include at least one second reservoir disposed in the at least one treatment region and configured to include one or more reactive components, wherein the one or more reactive components are configured to sequester the one or more bifunctional tags when bound to the one or more target components.

The device or system is useful in a method for treating a disease or condition mediated by or indicated by the one or more target components. The one or more target components can include, but are not limited to, cellular components (e.g., blood cells, cancer cells, pathogens), non-cellular components (e.g., proteins, lipids, sugars, carbohydrates, small molecules), or combinations thereof. Examples of diseases, conditions, or infections include, but are not limited to, acute and chronic inflammatory diseases (e.g., sepsis, multiple organ dysfunction syndrome, autoimmune disease, asthma, rhinitis, rheumatoid arthritis), cardiovascular disease, gastrointestinal disease, neoplastic disease, metabolic disease, bacterial infection (e.g., *Staphylococcus* bacteremia), viral infection (e.g., acquired immunodeficiency syndrome, hepatitis), parasite infection (e.g., malaria), or chemical or biological agent exposure (e.g., drug overdose, environmental toxin).

An implantable device is described that includes a body defining at least one lumen configured for fluid flow; at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can be configured to have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. The one or more bifunctional tags can be configured to enter a circulatory system of the mammalian subject at a site different from a site of the one or more reactive components. In an aspect, the one or more bifunctional tags can include, but is not limited to, one or more of a recognition element, recognition molecule, antibody, integrin, selectin, lectin, mimetic polymer, affibody, a label, or virus-like particle. The label can include, but is not limited to, one or more of a QDOT, a nanoparticle, a fluorescent molecule, a magnetic particle, a contrast agent, or a radioisotope. The one or more bifunctional tags can include one or more bifunctional antibodies. The one or more bifunctional antibodies is configured to bind to one or more of the target component and the reactive component. The one or more target components can include one or more of circulating target cells or circulating target emboli. The one or more target components can include, but is not limited to, one or more of tumor cells, emboli, misfolded proteins, aggregated proteins, antibodies, autoimmune antibodies, infectious agents, or infected cells. The one or more target components can include, but is not limited to, cancer cells, pre-cancer cells, autoimmune-related cells, B cells, T cells, phagocytes, platelets, lipoproteins, parasites, viruses, bacteria, fungi, or infected cells. The one or more reactive components can be configured to attach to the at least one lumen. The device can further include two or more parallel lumen configured to receive the one or more target components. In an aspect, a diameter of each of the two or more lumen can be approximately less than two cell diameters. In an aspect, a diameter of each of the two or more lumen can be approximately less than 10 μm.

The device including the at least one second reservoir disposed in the at least one treatment region and configured to include one or more reactive components, wherein the reactive components include two or more binding agents. The two or more binding agents are configured to sequester the one or more bifunctional tags when bound to the one or more target components. One or more binding agents can include binding agents, e.g., selectins or integrins, to slow passage of the target component through the treatment region. Other of the one or more binding agents can include sequestering agents, e.g., antibodies or mimetics, to sequester the one or more target component within the treatment region.

The one or more reactive components can be configured to alter, arrest, or destroy the one or more target cells. The one or more reactive components can be configured to produce necrosis or apoptosis in one or more target cells. The one or more reactive components can be configured to alter, arrest, or destroy the one or more target components. The one or more reactive components can be configured to be placed relative to a tumor or an organ in the mammalian subject. The one or more reactive components can include, but is not limited to, one or more of an adhesion molecule, antibody, binding mimetic, polymer, lectin, integrin, or selectin. The one or more reactive components can include, but is not limited to, one or more of a denaturing agent, degradative agent, or binding agent. The one or more reactive components can include, but is not limited to, a cytotoxic agent, a cytostatic agent, a programmed cell death-inducing agent, a chemotherapeutic agent, or an antibody-toxin agent. A programmed cell death-inducing agent can include an agent or compound that induces programmed cell death in eukaryotic or prokaryotic cells, or an agent or compound that induces apoptosis in eukaryotic cells. The one or more binding agents can include, but is not limited to, one or more of antibodies, receptors, or cognates configured to bind to one or more target components. The one or more binding agents can include, but is not limited to, one or more of lectin, binding protein, catalytic antibody, catalytic aptamer, protease conjugate, or photoactivatable conjugate. The device can further include one or more energy sources configured to supply energy to the at least one treatment region.

The device can further include one or more sensor configured to measure a physiological condition proximate to the device. The one or more sensor can be configured to detect one or more of unbound bifunctional tags or bifunctional tags bound to target components in the one or more of blood fluid or lymph fluid of the vertebrate subject. The one or more sensor can be configured to detect sequestration by the at least one reactive component. The device can further include a transmitter to report data from the one or more sensor. The one or more sensor can be configured to report to an outside source or to a computing device. The one or more sensor can be configured to function in, or proximal to, the one or more blood vessel or lymph vessel. The one or more sensor can be external to the at least one lumen. The one or more sensor can be internal to the at least one lumen. The device can further include at least one controller in communication with the one or more sensor. The at least one controller can include a processor. The at least one controller in communication with the one or more sensor can be configured to control the at least one controllable flow barrier to the at least one lumen.

The one or more sensor can be configured to detect the one or more target components and configured to communicate with the at least one controller to release the one or more bifunctional tags in response to the one or more detected target components. The one or more sensor can be configured to detect the one or more bifunctional tags complexed with the one or more target components and is configured to communicate with the controller to activate the one or more reactive components in response to the complex of the one or more bifunctional tags to the one or more target components. The one or more sensor can be configured to detect the one or more bifunctional tags complexed with the one or more target components and is configured to communicate with the controller to divert flow of the one or more of blood fluid or lymph fluid to the at least one lumen of the device. The one or more sensor can be configured to detect the one or more bifunctional tags complexed with the one or more target components and is configured to communicate with the controller to divert flow of the one or more of blood fluid or lymph fluid away from the at least one lumen of the device. The one or more sensor and the at least one controller can be configured to achieve a target level of the one or more target components in the vertebrate subject. The one or more sensor and the at least one controller can be configured to control the at least one controllable flow barrier, to activate the one or more reactive components, to release the one or more bifunctional tags, or to activate one or more energy sources. The one or more sensor and the at least one controller can be configured to control levels of the detected one or more target components to limit a deviation from the target level. In an aspect, the deviation can be determined by a weighted least squares fit. The target level can include a desired concentration of the one or more target components in the one or more of blood fluid or lymph fluid. The target level can include a desired range of concentrations of the one or more target components in the one or more of blood fluid or lymph fluid. The target level can include a desired ratio of concentrations of two or more target components in the one or more of blood fluid or lymph fluid. The target level can include a desired ratio of levels of two or more target components in the one or more of blood fluid or lymph fluid.

The one or more sensor can include, but is not limited to, a biosensor, chemical sensor, physical sensor, or optical sensor. The one or more sensor can include one or more target recognition elements. The one or more target recognition elements can include, but is not limited to, one or more of an aptamer, antibody, receptor, affibody, mimic, nucleic acid, or synthetic compound. The one or more sensor can include, but is not limited to, one or more of a recognition-based substrate, an aptamer-based substrate, an antibody-based substrate, surface plasmon resonance, genetically modified cells, or genetically modified cells with receptor-linked signaling. The genetically modified cells can include receptor-linked signaling by fluorogen-activating proteins. The one or more sensor can be configured to target the device to a site having an elevated level of the one or more target components. The one or more sensor can be configured to detect one or more of labeled bifunctional tags, bifunctional tags bound to the one or more target components, bifunctional tags bound to the one or more target components and to the one or more reactive components, or the one or more target components sequestered by the one or more bifunctional tags and the one or more reactive components. The device can be configured to report to an outside source or to a computing device, wherein the device is configured to report sequestration of the one or more target components.

The at least one first reservoir can be configured to provide one or more bifunctional tags is responsive to the controller. The at least one second reservoir can be configured to provide one or more reactive components is responsive to the controller. The device can further include at least one controllable flow barrier to fluid flow into the at least one lumen. The at least one controllable flow barrier can be configured to be at least partially open. In an aspect, a portion of the at least one lumen including the at least one first reservoir can be physically separated from a portion of the at least one lumen including the at least one second reservoir.

The one or more sensor can be configured to detect one or more of T-lymphocytes, B-lymphocytes, antibodies, pre-cancer cells, cancer cells, inflammatory cells, infected cells, bacteria, parasites, fungi, viruses, platelets, phagocytes, or lipoproteins. The one or more sensor can be configured to detect one or more of anaphylatoxins, cytokines, chemokines, leukotrienes, prostaglandins, complements, coagulation factors, or proinflammatory cytokines. The one or more sensor can be configured to detect one or more of body temperature, vital signs, edema, oxygen level, or pathogen/toxin level of the subject. The one or more sensor can be configured to detect one or more of TNF-α, IL-1, IL-1β, IL-6, IL-8, IL-10, IL-12, LPB, IFN-γ, LIF, MIF, MIP-1, MCP-1, C3-a, or C5-a. The one or more sensor can be configured to detect one or more of exotoxins, endotoxins, or lipopolysaccharide.

The one or more second reservoirs can include a matrix configured to present one or more reactive components. The one or more second reservoirs can include a matrix configured to present one or more reactive components. The one or more binding agents can include one or more target recognition elements. The one or more target recognition elements can include, but is not limited to, one or more of aptamer, antibodies, receptors, affibody, mimic, nucleic acid, synthetic compound, or cognates configured to bind to at least one of the one or more target components. The binding agent can include one or more of a specific binding ligand or a hydrophobic surface. The matrix can include, but is not limited to, one or more of beads, cells, vesicles, filters, hydrogel polymers, microparticles, nanoparticles, adsorbent, absorbent, or synthetic polymers. The specific binding ligand or the hydrophobic surface can include, but is not limited to, one or more of nucleic acid aptamers, peptide aptamers, molecular imprinting polymer, antibodies or fragments thereof, high affinity mimetics, synthetic binding molecules, or receptor binding molecules. The matrix can include, but is not limited to, one or more of a lectin, binding protein, receptor, antibody, catalytic antibody, catalytic aptamer, protease conjugate, or photoactivatable conjugate.

The energy source can include, but is not limited to, acoustic energy or electronic energy. The energy source can include ultrasound. In an aspect, the energy source can include high-intensity focused ultrasound. The energy source can include, but is not limited to, at least one of microwave irradiation, gamma irradiation, electromagnetic irradiation, heat, electron beam irradiation, vibrational/frequency irradiation, or atmospheric pressure glow discharge. The vibrational/frequency irradiation can include a set of differing energy inputs specifically directed to the one or more target components, wherein the set of differing energy inputs selectively resonates a plurality of resonant structures in the one or more target components, and wherein the resonance controllably alters or reduces the activity of the one or more target components in the one or more of blood fluid or lymph fluid of the vertebrate subject. In an aspect, the one or more target components can be modified with a functional group configured to be responsive to the set of differing energy inputs. The energy source can be coupled to one or more sensor configured to selectively direct energy to the target component. The one or more denaturing agents can include, but is not limited to, at least of an acid, base, solvent, detergent, cross-linking agent, chaotropic agent, disulfide bond reducer, enzyme, drug, cell, or radical ion. The one or more degradative agents can include, but is not limited to, at least one of an enzyme, coenzyme, enzyme complex, catalytic antibody, proteasome, strong acid, strong base, radical, photoactivatable agent, drug, cell, or radical ion. In an aspect, the catalytic antibody can generate a radical ion. The one or more second reservoirs can include a source for producing the one or more reactive components. The source can include at least one reservoir and at least one producer. The at least one producer can include at least one encapsulated cell. The at least one encapsulated cell can produce the one or more reactive components. The at least one encapsulated cell can include at least one genetically-engineered cell. The at least one encapsulated cell can include, but is not limited to, at least one of a mammalian cell, bacterial cell, yeast cell, plant cell, insect cell, artificial cell, or enucleated cell. The at least one encapsulated cell can include, but is not limited to, one or more of a myeloid cell, lymphocyte, or precursor thereof. The at least one encapsulated cell can include, but is not limited to, one or more of a T-lymphocyte, B-lymphocyte, macrophage, monocyte, neutrophil, or NK cell. The at least one producer can include, but is not limited to, a protein, lipid micelle, liposome, synthetic polymer, or a combination thereof. The at least one producer can include a catalytic antibody. In an aspect, the catalytic antibody can include a radical ion generator.

In an aspect, the device can be intracorporeal. The device can be mobile within the blood vessel or lymph vessel. The device can be configured to be implanted. The device can include, but is not limited to, a stent, bypass implant, nanostructure or microstructure. The device can be configured to be implanted relative to an organ or tissue in the subject. The device can be at least partially extracorporeal. The device can include, but is not limited to, a dialysis device, hemoperfusion device, apheresis device, intravenous device, shunt device, or patch device.

A method for treating an inflammatory condition or inflammatory disease in a vertebrate subject is described that includes providing an implantable device including a body defining at least one lumen configured for fluid flow; at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can be configured to have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. The one or more bifunctional tags can be configured to enter a circulatory system of the mammalian subject at a site different from a site of the one or more reactive components. In an aspect, the one or more bifunctional tags can include, but is not limited to, one or more of a recognition element, recognition molecule, antibody, integrin, selectin, lectin, mimetic polymer, affibody, a label, or virus-like particle. The label can include, but is not limited to, one or more of a QDOT, a nanoparticle, a fluorescent molecule, a magnetic particle, a contrast agent, or a radioisotope. The one or more bifunctional tags can include one or more bifunctional antibodies. The one or more bifunctional antibodies is configured to bind to one or more of the target component and the reactive component. The one or more target components can include one or more of circulating target cells or circulating target emboli. The one or more target components can include, but is not limited to, one or more of tumor cells, emboli, misfolded proteins, aggregated proteins, antibodies, autoimmune antibodies, infectious agents, or infected cells. The one or more target components can include, but is not limited to, cancer cells, pre-cancer cells, autoimmune-related cells, B cells, T cells, phagocytes, platelets, lipoproteins, parasites, viruses, bacteria, fungi, or infected cells. The one or more reactive components can be configured to attach to the at least one lumen.

The method can further include providing two or more parallel lumen configured to receive the one or more target components. In an aspect, a diameter of each of the two or more lumen can be approximately less than two cell diameters. In an aspect, a diameter of each of the two or more lumen can be approximately less than 10 μm.

The one or more reactive components can be configured to alter, arrest, or destroy the one or more target cells. The one or more reactive components can be configured to produce necrosis or apoptosis in one or more target cells. The one or more reactive components can be configured to alter, arrest, or destroy the one or more target components. The one or more reactive components can be configured to be placed relative to a tumor or an organ in the mammalian subject. The one or more reactive components can include, but is not limited to, one or more of an adhesion molecule, antibody, binding mimetic, polymer, lectin, integrin, or selectin. The one or more reactive components can include, but is not limited to, one or more of a denaturing agent, degradative agent, or binding agent. The one or more reactive components can include, but is not limited to, a cytotoxic agent, a cytostatic agent, a programmed cell death-inducing agent, a chemotherapeutic agent, or an antibody-toxin agent. The one or more binding agents can include, but is not limited to, one or more of antibodies, receptors, or cognates configured to bind to one or more target components. The one or more binding agents can include, but is not limited to, one or more of lectin, binding protein, catalytic antibody, catalytic aptamer, protease conjugate, or photoactivatable conjugate. The method can further include providing one or more energy sources configured to supply energy to the at least one treatment region.

The method can further include providing one or more sensors configured to measure a physiological condition proximate to the device. The one or more sensor can be configured to detect one or more of unbound bifunctional tags or bifunctional tags bound to target components in the one or more of blood fluid or lymph fluid of the vertebrate subject. The one or more sensor can be configured to detect sequestration by the at least one reactive component. The method can further include providing a transmitter to report data from the one or more sensor. The one or more sensor can be configured to report to an outside source or to a computing device. The one or more sensor can be configured to function in, or proximal to, the one or more blood vessel or lymph vessel. The one or more sensor can be external to the at least one lumen. The one or more sensor can be internal to the at least one lumen. The method can further include providing at least one controller in communication with the one or more sensor. The at least one controller can include a processor. The method can further include providing at least one controllable flow barrier to fluid flow into the at least one lumen. The at least one controllable flow barrier can be configured to be at least partially open. The at least one controller in communication with the one or more sensor can be configured to control the at least one controllable flow barrier to the at least one lumen.

The one or more sensor can be configured to detect the one or more target components and configured to communicate with the at least one controller to release the one or more bifunctional tags in response to the one or more detected target components. The one or more sensor can be configured to detect the one or more bifunctional tags complexed with the one or more target components and is configured to communicate with the controller to activate the one or more reactive components in response to the complex of the one or more bifunctional tags to the one or more target components. The one or more sensor can be configured to detect the one or more bifunctional tags complexed with the one or more target components and is configured to communicate with the controller to divert flow of the one or more of blood fluid or lymph fluid to the at least one lumen of the device. The one or more sensor can be configured to detect the one or more bifunctional tags complexed with the one or more target components and is configured to communicate with the controller to divert flow of the one or more of blood fluid or lymph fluid away from the at least one lumen of the device. The one or more sensor and the at least one controller can be configured to achieve a target level of the one or more target components in the vertebrate subject. The one or more sensor and the at least one controller can be configured to control the at least one controllable flow barrier, to activate the one or more reactive components, to release the one or more bifunctional tags, or to activate one or more energy sources. The one or more sensor and the at least one controller can be configured to control levels of the detected one or more target components to limit a deviation from the target level. In an aspect, the deviation can be determined by a weighted least squares fit. The target level can include a desired concentration of the one or more target components in the one or more of blood fluid or lymph fluid. The target level can include a desired range of concentrations of the one or more target components in the one or more of blood fluid or lymph fluid. The target level can include a desired ratio of concentrations of two or more target components in the one or more of blood fluid or lymph fluid. The target level can include a desired ratio of levels of two or more target components in the one or more of blood fluid or lymph fluid.

The one or more sensor can include, but is not limited to, a biosensor, chemical sensor, physical sensor, or optical sensor. The one or more sensor can include one or more target recognition elements. The one or more target recognition elements can include, but is not limited to, one or more of an aptamer, antibody, receptor, affibody, mimic, nucleic acid, or synthetic compound. The one or more sensor can include, but is not limited to, one or more of a recognition-based substrate, an aptamer-based substrate, an antibody-based substrate, surface plasmon resonance, genetically modified cells, or genetically modified cells with receptor-linked signaling. The genetically modified cells can include receptor-linked signaling by fluorogen-activating proteins. The one or more sensor can be configured to target the device to a site having an elevated level of the one or more target components. The one or more sensor can be configured to detect one or more of labeled bifunctional tags, bifunctional tags bound to the one or more target components, bifunctional tags bound to the one or more target components and to the one or more reactive components, or the one or more target components sequestered by the one or more bifunctional tags and the one or more reactive components. The device can be configured to report to an outside source or to a computing device, wherein the device is configured to report sequestration of the one or more target components.

The at least one first reservoir can be configured to provide one or more bifunctional tags is responsive to the controller. The at least one second reservoir can be configured to provide one or more reactive components is responsive to the controller. In an aspect, a portion of the at least one lumen including the at least one first reservoir can be physically separated from a portion of the at least one lumen including the at least one second reservoir.

The one or more sensor can be configured to detect one or more of T-lymphocytes, B-lymphocytes, antibodies, pre-cancer cells, cancer cells, inflammatory cells, infected cells, bacteria, parasites, fungi, viruses, platelets, phagocytes, or lipoproteins. The one or more sensor can be configured to detect one or more of anaphylatoxins, cytokines, chemokines, leukotrienes, prostaglandins, complements, coagulation factors, or proinflammatory cytokines. The one or more sensor can be configured to detect one or more of body temperature, vital signs, edema, oxygen level, or pathogen/toxin level of the subject. The one or more sensor can be configured to detect one or more of TNF-α, IL-1, IL-1β, IL-6, IL-8, IL-10, IL-12, LPB, IFN-γ, LIF, MIF, MIP-1, MCP-1, C3-a, or C5-a. The one or more sensor can be configured to detect one or more of exotoxins, endotoxins, or lipopolysaccharide.

The one or more second reservoirs can include a matrix configured to present one or more reactive components. The one or more second reservoirs can include a matrix configured to present one or more reactive components. The one or more binding agents can include one or more target recognition elements. The one or more target recognition elements can include, but is not limited to, one or more of aptamer, antibodies, receptors, affibody, mimic, nucleic acid, synthetic compound, or cognates configured to bind to at least one of the one or more target components. The binding agent can include one or more of a specific binding ligand or a hydrophobic surface. The matrix can include, but is not limited to, one or more of beads, cells, vesicles, filters, hydrogel polymers, microparticles, nanoparticles, adsorbent, absorbent, or synthetic polymers. The specific binding ligand or the hydrophobic surface can include, but is not limited to, one or more of nucleic acid aptamers, peptide aptamers, molecular imprinting polymer, antibodies or fragments thereof, high affinity mimetics, synthetic binding molecules, or receptor binding molecules. The matrix can include, but is not limited to, one or more of a lectin, binding protein, receptor, antibody, catalytic antibody, catalytic aptamer, protease conjugate, or photoactivatable conjugate.

The energy source can include, but is not to, acoustic energy or electronic energy. The energy source can include ultrasound. In an aspect, the energy source can include high-intensity focused ultrasound. The energy source can include, but is not limited to, at least one of microwave irradiation, gamma irradiation, electromagnetic irradiation, heat, electron beam irradiation, vibrational/frequency irradiation, or atmospheric pressure glow discharge. The vibrational/frequency irradiation can include a set of differing energy inputs specifically directed to the one or more target components, wherein the set of differing energy inputs selectively resonates a plurality of resonant structures in the one or more target components, and wherein the resonance controllably alters or reduces the activity of the one or more target components in the one or more of blood fluid or lymph fluid of the vertebrate subject. In an aspect, the one or more target components can be modified with a functional group configured to be responsive to the set of differing energy inputs. The energy source can be coupled to one or more sensor configured to selectively direct energy to the target component. The one or more denaturing agents can include, but is not limited to, at least of an acid, base, solvent, detergent, cross-linking agent, chaotropic agent, disulfide bond reducer, enzyme, drug, cell, or radical ion. The one or more degradative agents can include, but is not limited to, at least one of an enzyme, coenzyme, enzyme complex, catalytic antibody, proteasome, strong acid, strong base, radical, photoactivatable agent, drug, cell, or radical ion. In an aspect, the catalytic antibody can generate a radical ion. The one or more second reservoirs can include a source for producing the one or more reactive components. The source can include at least one reservoir and at least one producer. The at least one producer can include at least one encapsulated cell. The at least one encapsulated cell can produce the one or more reactive components. The at least one encapsulated cell can include at least one genetically-engineered cell. The at least one encapsulated cell can include, but is not limited to, at least one of a mammalian cell, bacterial cell, yeast cell, plant cell, insect cell, artificial cell, or enucleated cell. The at least one encapsulated cell can include, but is not limited to, one or more of a myeloid cell, lymphocyte, or precursor thereof. The at least one encapsulated cell can include, but is not limited to, one or more of a T-lymphocyte, B-lymphocyte, macrophage, monocyte, neutrophil, or NK cell. The at least one producer can include, but is not limited to, a protein, lipid micelle, liposome, synthetic polymer, or a combination thereof. The at least one producer can include a catalytic antibody. In an aspect, the catalytic antibody can include a radical ion generator.

A method for modulating an inflammatory condition or inflammatory disease in a vertebrate subject is described that includes providing an implantable device including a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. The one or more reactive components can include, but is not limited to, a one or more of a denaturing agent, degradative agent or binding agent.

A method for treating an infectious disease or infectious condition in a vertebrate subject is described that includes providing an implantable device including a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. The one or more reactive components can include, but is not limited to, a one or more of a denaturing agent, degradative agent or binding agent.

A method for modulating an infectious disease or infectious condition in a vertebrate subject is described that includes providing an implantable device including a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. The one or more reactive components can include, but is not limited to, a one or more of a denaturing agent, degradative agent or binding agent.

A method for treating a neoplastic disease or neoplastic condition in a vertebrate subject is described that includes providing an implantable device including a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components.

A method for modulating a neoplastic disease or neoplastic condition in a vertebrate subject is described that includes providing an implantable device including a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. The one or more reactive components can include, but is not limited to, a one or more of a denaturing agent, degradative agent or binding agent.

A system is described that includes an implantable device including a body defining at least one lumen configured for fluid flow; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. The one or more reactive components can include, but is not limited to, a one or more of a denaturing agent, degradative agent or binding agent.

A device is described that includes a system including a signal-bearing medium including one or more instructions for treatment of a subject through an implantable device including a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components; and one or more instructions for receiving data including data for delivering one or more reactive components configured to sequester the one or more bifunctional tags when bound to the one or more target components.

A system is described that includes at least one computer program included on a computer-readable medium for use with at least one computer system wherein the computer program includes a plurality of instructions including, one or more instructions for determining at least one treatment of one or more of blood fluid or lymph fluid of a vertebrate subject through an implantable device including a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in the one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components; and one or more instructions for receiving data including data for delivering one or more reactive components configured to sequester the one or more bifunctional tags when bound to the one or more target components.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 3 depicts a diagrammatic view of an aspect of an embodiment of a device.

DETAILED DESCRIPTION

Figure 1:
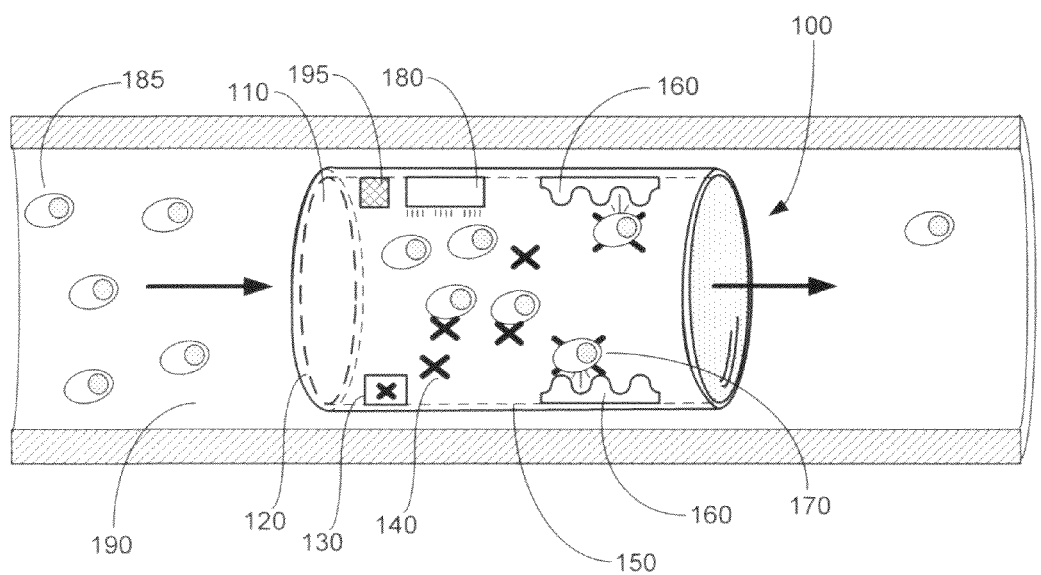
FIG. 1 depicts a diagrammatic view of an aspect of an embodiment of a device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This document uses formal outline headings for clarity of presentation. However, it is to be understood that the outline headings are for presentation purposes, and that different types of subject matter may be discussed throughout the application (e.g., method(s) may be described under composition heading(s) and/or kit headings, arid/or descriptions of single topics may span two or more topic headings). Hence, the use of the formal outline headings is not intended to be in any way limiting. Devices, systems, and methods are disclosed herein for controlling or modulating the levels of one or more target components in the blood fluid and/or lymph fluid of a vertebrate subject. The implantable device or system can include a body defining at least one lumen configured for fluid flow. The device or system can further include at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject, and at least one treatment region disposed within the at least one lumen. The device or system can further include at least one second reservoir disposed in the at least one treatment region and configured to include one or more reactive components, wherein the one or more reactive components are configured to sequester the one or more bifunctional tags when bound to the one or more target components.

The device or system is useful in a method for treating a disease or condition mediated by or indicated by the one or more target components. The one or more target components can include, but are not limited to, cellular components (e.g., blood cells, cancer cells, pathogens), non-cellular components (e.g., proteins, lipids, sugars, carbohydrates, small molecules), or combinations thereof. Examples of diseases, conditions, or infections include, but are not limited to, acute and chronic inflammatory diseases (e.g., sepsis, multiple organ dysfunction syndrome, autoimmune disease, asthma, rhinitis, rheumatoid arthritis), cardiovascular disease, gastrointestinal disease, neoplastic disease, metabolic disease, bacterial infection (e.g., *Staphylococcus* bacteremia), viral infection (e.g., acquired immunodeficiency syndrome, hepatitis), parasite infection (e.g., malaria), or chemical or biological agent exposure (e.g., drug overdose, environmental toxin).

An implantable device is described that includes a body defining at least one lumen configured for fluid flow; at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can be configured to have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. In an aspect, the one or more bifunctional tags can include, but is not limited to, one or more of a recognition element, recognition molecule, antibody, integrin, selectin, lectin, mimetic polymer, affibody, a label, or virus-like particle. The label can include, but is not limited to, one or more of a QDOT, a nanoparticle, a fluorescent molecule, a magnetic particle, a contrast agent, or a radioisotope. The one or more bifunctional tags can include one or more bifunctional antibodies. The one or more bifunctional antibodies can be configured to bind to one or more of the target component and the reactive component. The one or more target components can include one or more of circulating target cells or circulating target emboli. The one or more target components can include, but is not limited to, one or more of tumor cells, emboli, misfolded proteins, aggregated proteins, antibodies, autoimmune antibodies, infectious agents, or infected cells. The one or more target components can include, but is not limited to, cancer cells, pre-cancer cells, autoimmune-related cells, B cells, T cells, phagocytes, platelets, lipoproteins, parasites, viruses, bacteria, fungi, or infected cells.

The one or more reactive components can include one or more of a denaturing agent, degradative agent, or binding agent. The one or more reactive components can further include a cytotoxic agent, a cytostatic agent, a programmed cell death-inducing agent, a chemotherapeutic agent, or an antibody-toxin agent. A programmed cell death-inducing agent can include an agent or compound that induces programmed cell death in eukaryotic or prokaryotic cells, e.g., bacterial cells, or an agent or compound that induces apoptosis in eukaryotic cells, e.g., parasite cells, pre-cancer cells, cancer cells, or other vertebrate cells.

A method for treating an disease, condition, or infection in a vertebrate subject is described that includes providing an implantable device including a body defining at least one lumen configured for fluid flow; at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components.

Diseases, conditions, or infections wherein the disease, condition, or infection can be modulated, alleviated, treated, prevented, reduced or eliminated by modulating a physiological effect of one or more target components in the blood fluid or lymph fluid include, but are not limited to, cardiovascular diseases (e.g., ischemic heart disease, inflammatory heart disease), metabolic diseases (e.g., diabetes), gastrointestinal diseases (e.g., colitis, Crohn's disease), bacterial infections (e.g., *Staphylococcus* bacteremia, anthrax), viral infections (e.g., AIDS, hepatitis, hemorrhagic fever), parasitic infections (e.g., malaria, sleeping sickness, Chagas disease), metastatic cancer (e.g., lung, breast, skin, colon, kidney, prostate, pancreas, and cervix); blood cancers (e.g., leukemia, lymphoma, Hodgkin's disease, myeloma); chemical or biological agent exposure (e.g., drug overdose, poisoning, exposure to environmental toxin). Additional examples include a number of inflammatory diseases including but not limited to systemic inflammatory response syndrome, sepsis, septic shock, multiple organ dysfunction syndrome, ischemia reperfusion, hyperreactive airway disease, (e.g., asthma, chronic obstructive pulmonary disease, rhinitis, sinusitis), allergic reaction, anaphylaxis, autoimmune disease, infectious disease, pulmonary failure, allograft rejection, graft versus host disease (GVHD), chronic inflammatory disease, psoriatic arthritis, rheumatoid arthritis.

A system is described that includes an implantable device including a body defining at least one lumen configured for fluid flow; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. The one or more reactive components can have an increased affinity for the one or more bifunctional tags bound to the one or more target components compared to an affinity for the one or more bifunctional tags unbound to the one or more reactive components. The one or more reactive components can be configured to modulate a physiological effect of the one or more target components. The one or more reactive components can include, but is not limited to, a one or more of a denaturing agent, degradative agent or binding agent.

Figure 2:
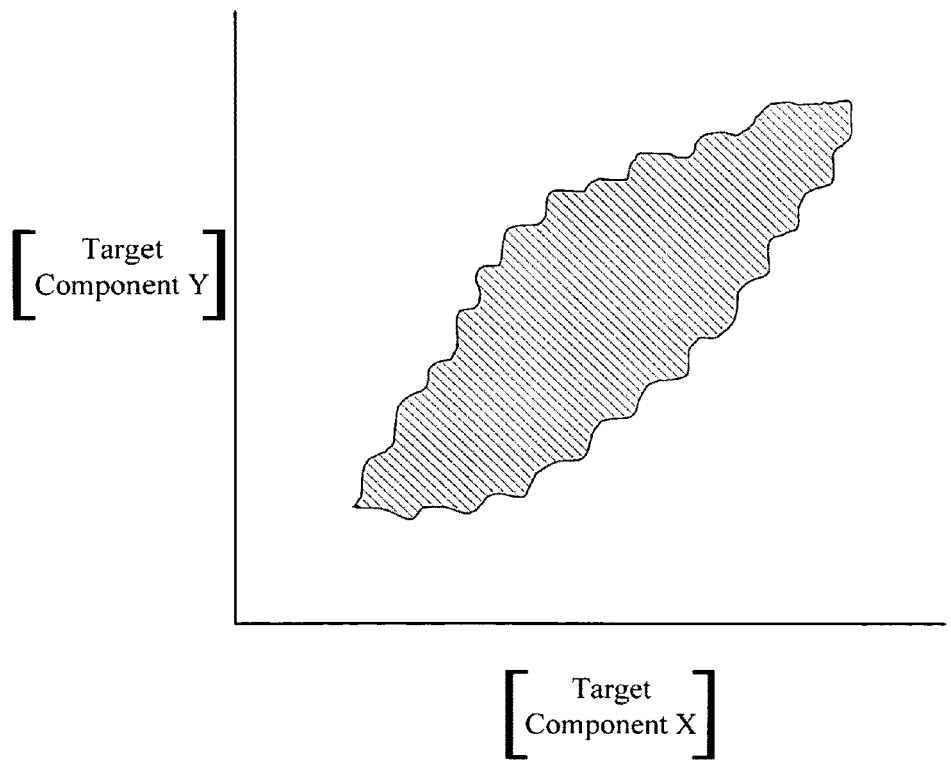
FIG. 2 depicts a diagrammatic view of an aspect of an embodiment of a device.

With reference to the figures, and with reference now to FIGS. 1, 2, and 3, depicted is an aspect of a device, system, or method that can serve as an illustrative environment of and/or for subject matter technologies, for example, device including one or more first reservoirs configured to include one or more bifunctional tags configured to function in, or proximal to, one or more blood vessel or lymph vessel of a vertebrate subject and configured to selectively bind to one or more target components in one or more of blood fluid or lymph fluid of the vertebrate subject; and one or more second reservoirs configured to include one or more reactive components configured to sequester the one or more bifunctional tags when bound to the one or more target components. The specific devices and methods disclosed herein are intended as merely illustrative of their more general counterparts.

Referring to FIG. 1, depicted is a partial diagrammatic view of an illustrative embodiment of an implantable device 100 including a body defining at least one lumen 110 configured for fluid flow; at least one controllable flow barrier 120 to fluid flow into the at least one lumen 110; at least one first reservoir 130 disposed within the body and configured to include one or more bifunctional tags 140, wherein the one or more bifunctional tags 140 are configured to selectively bind to one or more target components 185 in one or more of blood fluid or lymph fluid 190 of a vertebrate subject; at least one treatment region 150 disposed within the at least one lumen 110; and at least one second reservoir 160 disposed in the at least one treatment region 150 and configured to include one or more reactive components 170, wherein the one or more reactive components 170 are configured to sequester the one or more bifunctional tags 140 when bound to the one or more target components 185. The one or more reactive components 170 include, but are not limited to, a denaturing agent, a degradative agent, or an energy source, wherein the one or more reactive components 170 is configured to alter, arrest, or destroy the one or more target components 85. The device can further include one or more sensors 180 configured to detect one or more of unbound bifunctional tags or bifunctional tags 140 bound to target components 185 in the one or more of blood fluid or lymph fluid 190 of the vertebrate subject. The device can further include at least one controller 195 in communication with the one or more sensor 180 and in communication with the at least one controllable flow barrier 120 to the at least one lumen 110, wherein the one or more reactive components 170 is configured to contact the one or more of blood fluid or lymph fluid 190 of the vertebrate subject.

Referring to FIG. 2, depicted is a partial diagrammatic view of an illustrative embodiment of calculations of a target value of one or more target components in an implantable device including one or more sensor configured to detect one or more of unbound bifunctional tags or bifunctional tags bound to the target components in the one or more of blood fluid or lymph fluid of the vertebrate subject and including at least one controller in communication with the one or more sensor and in communication with at least one controllable flow barrier to at least one lumen. In an aspect, the target value can include a desired concentration of the one or more target components in the peripheral blood, or the target value can include a desired range of concentrations of the one or more target components in the peripheral blood. In a further aspect, the target value can include a desired ratio of concentrations of two or more target components in the peripheral blood. In an aspect, the target value can be used to determine relative levels of the target components. The desired ratio of concentrations can be determined by any method or means, including for example, by a least squares fit of the concentrations of the two or more target components. For example, the desired ratio of concentrations can be determined by a least squares fit of the concentrations of the two or more target components at concentrations $x_1$, $x_2$, $x_3$, and $x_4$ for a first inflammatory mediator, X, and at concentrations $y_1$, $y_2$, $y_3$, and $y_4$ for a second inflammatory mediator, Y. The least squares can fit to a line or to a two or three dimensional space indicating the preferred ratio of the two or more target components.

Referring to FIG. 3, depicted is a logic flowchart of a method 301 for treating an inflammatory disease or inflammatory condition in a subject. The method includes providing an implantable device 302 including a body defining at least one lumen configured for fluid flow; at least one controllable flow barrier to fluid flow into the at least one lumen; at least one first reservoir disposed within the body and configured to include one or more bifunctional tags, wherein the one or more bifunctional tags are configured to selectively bind to one or more target components in one or more of blood fluid or lymph fluid of a vertebrate subject; at least one treatment region disposed within the at least one lumen; and at least one second reservoir disposed in the at least one treatment region and configured to include one or more reactive components, wherein the one or more reactive components are configured to sequester the one or more bifunctional tags when bound to the one or more target components. In an aspect, the one or more reactive components 303 can have an increased affinity for the one or more bifunctional tags bound to the one or more target components compared to an affinity for the one or more bifunctional tags unbound to the one or more reactive components. In an aspect, the one or more reactive components 304 can include a one or more of a denaturing agent, degradative agent, binding agent, or energy source.

Target Components

The device disclosed herein is configured to remove one or more target components from the blood fluid or lymph fluid of a vertebrate subject using one or more bifunctional tags. The target component can be a normal component or an abnormal component of the blood fluid or lymph fluid of the vertebrate subject. The target component can be associated with a normal physiological state or with a pathological state of the subject. The target component can be a non-cellular component or a cellular component of the blood fluid or lymph fluid of a vertebrate subject. Examples of non-cellular target components include but are not limited to proteins, lipids, sugars, minerals, vitamins or combinations thereof. Examples of cellular target components include but are not limited to red blood cells, white blood cells, pathogens, pathogen-infected blood cells, cancer cells. In a further aspect, the one or more target components can be one or more of a blood clot, a thrombus, an embolus, a plaque, a lipid, an aggregate, a cell, a specific type of cells, a cell fragment, a cellular component, an organelle, a collection or aggregation of cells, a therapeutic agent, an illicit drug, a drug of abuse, a toxin.

In an aspect, the one or more target components are cells circulating in the blood and/or lymph of a vertebrate subject. Cellular target components can include but are not limited to blood cells (e.g., platelets, red blood cells, neutrophils, lymphocytes, monocytes, eosinophils, basophils), pathogens (e.g., virus, bacteria, fungus, parasite), and cancer cells (e.g., metastatic cancer cells, blood cancer cells).

The one or more cellular target components can be one or more blood cells associated with a pathological state in which the normal circulating levels of one or more class of blood cells is elevated. For example, elevated levels of red blood cells are associated with exposure to carbon monoxide, long-term lung disease, kidney disease, some cancers, certain forms of heart disease, liver disease. Elevated levels of platelets are associated with bleeding, iron deficiency, cancer, or bone marrow pathologies. Elevated levels of neutrophils and eosinophils are associated with infection, malignancy and autoimmune diseases. In an aspect, the cellular target components are blood cells that are modified or altered as a result of a disease, condition and/or infection. For example, hyperactivated B-lymphocytes in patients with inflammatory bowel disease exhibit increased surface expression of toll-like receptor 2 (TLR2) relative to B-lymphocytes from normal individuals. See, e.g., Noronha, et al., *J. Leukoc. Biol.* 86: Epub ahead of print; Rea, WebMD. Complete Blood Count (CBC) at www.webmd.com/a-to-z-guides/complete-blood-count-cbc. Last updated Sep. 12, 2008; accessed Oct. 5, 2009; each of which is incorporated herein by reference.

The one or more cellular target components can include one or more pathogens or pathogen-infected cells circulating in the blood and/or the lymph of a vertebrate subject. Examples of blood borne pathogens include but are not limited to viruses, e.g., human immunodeficiency virus (HIV), and the hepatitis B, hepatitis C, and hepatitis D viruses,; bacteria, e.g., *Staphylococcus, Streptococcus, Pseudomonas, Haemophilus, Escherichia coli*; fungi, e.g., *Aspergillus, Candida albicans, Candida glabrata, Torulopsis glabrata, Candida tropicalis, Candida krusei*, and *Candida parapsilosis*; and parasites, e.g., *Trypanosoma cruzi, Trypanosoma brucei, Leishmania, Plasmodium, Babesia microti, Toxoplasma gondii*. Other bacterial pathogens that might be found in the blood and/or lymph at some point during a bacterial infection include but are not limited to *Bartonella, Coxiella burnetii, Chlamydia, Salmonella, Shigella, Yersinia, Legionella, Neisseria, Mycobacterium tuberculosis, Listeria, Corynebacterium diphtheriae, Campylobacter, Enterobacter*. Other viral pathogens or pathogen-infected cells that might be found in the blood and/or lymph at some point during a viral infection include, but are not limited to, cells infected with cytomegalovirus, influenza, human T-lymphotrophic virus, Epstein-Barr virus, roseolovirus, herpes lymphotropic virus, Karposi's sarcoma-associated herpesvirus, herpes simplex virus, Ebola virus, Marburg virus.

In an aspect, the one or more cellular target components can include one or more circulating blood cells infected with a pathogen including but not limited to bacteria, virus, or parasite. In an aspect, the one or more cellular target components are circulating blood cells infected with bacteria such as, for example, red blood cells infected with *B. bacilliformis* or *Bartonella* spp. See, e.g., Dehio, *Cell. Microbiol.* 10: 1591-1598, 2008; Chomel et al., *Vet. Res.* 40: 29, 2009, each of which is incorporated herein by reference. In an aspect, the one or more cellular target components are one or more cells infected with HIV, primarily CD4+ T lymphocytes but also including macrophages and dendritic cells. In a further aspect, the one or more cellular target components are red blood cells infected with the malaria parasite *Plasmodium falciparum*. Red blood cells infected with *P. falciparum* can be distinguished from normal red blood cells by visual inspection, changes in granularities and changes in surface protein expression including expression on the red blood cell surface of the parasite derived protein *P. falciparum* erythrocyte membrane protein (PfEMP1). See, e.g., Dempster & Di Ruperto, *Circuits and Systems,* 2001. ISCAS 2001, The 2001 IEEE International Symposium, 5: 291-294, 2001; Weatherall, et al., *Hematology Am. Soc. Hematol. Educ. Program* 35-57, 2002; Horata, et al., *Malaria J.* 8:184, 2009, each of which is incorporated herein by reference.

The one or more cellular target components can include one or more cancer cells circulating in the blood and/or lymph of a vertebrate subject. In an aspect, the cancer cells can be circulating tumor cells that have metastasized from solid tumors located elsewhere in the body. Examples of solid tumors from which metastatic cells can arise include but are not limited to carcinomas (e.g., adrenal, breast, cervical, colon, endometrial, lung, ovarian, pancreatic, prostate, stomach, testicular, thyroid, melanoma, head & neck) and sarcomas (e.g., brain, Ewing's sarcoma, Karposi's sarcoma, osteosarcoma, spinal cord). Circulating tumor cells are indicative of metastasis and may suggest a need for changes in the treatment regime. For example, the detection of circulating tumor cells in melanoma patients who are clinically "disease-free" indicates disease recurrence, tumor cell spreading, and a high potential for distant metastasis, and enables identification of high-risk melanoma patients. See, e.g., Schuster et al., *Clin. Cancer Res.* 13:1171-1178, 2007, which is incorporated herein by reference. The appearance of circulating tumor cells may also provide an indication of the long term prognosis for the patient. For example, breast cancer patients with levels of circulating tumor cells equal to or higher than five cells per 7.5 milliliters of blood have a shorter median progression-free survival (2.7 months vs. 7.0 months) and shorter overall survival (10.1 months versus greater than 18.0 months) as compared with breast cancer patients with less than five cells per 7.5 milliliters of blood. See, Cristofanilli et al. *N. Engl. J. Med.* 351:781-791, 2004, which is incorporated herein by reference.

In an aspect, the cancer cells can include associated with blood cancers. Examples of blood cancers include but are not limited to lymphoma, various types of leukemia, and multiple myeloma. Lymphoma is a cancer of lymphocytes which usually begins in a lymph node but can originate from the stomach, intestines, skin or any other organ. The two main types of lymphoma are Hodgkin's disease and non-Hodgkin's lymphoma. In Hodgkin's disease, the abnormal cells are called the Reed-Sternberg cells, giant binucleated or multinucleated macrophages. This type of cancer can spread throughout the lymphatic system, affecting any organ or lymph tissue in the body. Non-Hodgkin's lymphoma is classified by the size, type and distribution of cancer cells in the lymph nodes. Low-grade lymphomas include small-lymphocytic lymphoma, follicular small-cleaved-cell lymphoma, and follicular mixed-cell lymphoma. Intermediate-grade lymphomas include follicular large-cell lymphoma, diffuse small-cleaved-cell lymphoma., diffuse mixed lymphoma, and diffuse large-cell lymphoma. High-grade lymphomas include immunoblastic lymphoma, lymphoblastic lymphoma, and small noncleaved (Burkitt's and non-Burkitt's) lymphoma. Multiple myeloma is cancer of the bone marrow caused by the uncontrolled growth of effector B cells. Effector B cells normally make antibodies (e.g., immunoglobulins) to fight infections. In multiple myeloma effector B cells multiply uncontrollably, generating too much of a single type of immunoglobulin. The level of other immunoglobulins drops, leaving the patient vulnerable to infection. The cancerous plasma cells collect in the bones and bone marrow and can form tumors that destroy the bone tissue, causing the bones to become fragile and prone to fracture.

In an aspect, the one or more target components include non-cellular components present in the blood and/or lymph of a vertebrate subject. Non-cellular components can include but are not limited to sugars (e.g., glucose), lipids (e.g., triacylglycerols, cholesterol, phospholipids), vitamins, minerals, non-protein hormones (e.g., estrogen, testosterone), proteins (e.g., enzymes, hormones, antibodies, blood clotting factors, lipoproteins). Additional examples of proteins found in the blood and/or lymph include but are not limited to serum proteins (e.g., subclasses of immunoglobulins, complement factors, C1 esterase, circulating immune complexes, albumin, anti-trypsin, fetoprotein, acid glycoprotein, alpha-macroglobulin, beta-microglobulin, ceruloplasmin, transferrin), acute phase proteins associated with disease (e.g., C-reactive protein, SPLA2, ferritin), coagulation or complement related proteins (e.g., tissue-factor pathway inhibitor, soluble tissue factor, kallikrein, factor XIIa, thrombin, lupus anticoagulant, soluble CD46, soluble CD55), and markers of cellular activation (e.g., elastase, elastase/antitrypsin complexes, lactoferrin, granzym, nucleosomes, soluble CD16, soluble CD27).

The one or more target components can include one or more inflammatory mediators. Examples of inflammatory mediators include but are not limited to interferons (IFN) IFN-α, IFN-β, and IFN-γ; interleukins (IL) IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-27, IL-28, IL-29, IL-30, IL-31, and IL-32; tumor necrosis factor (TNF) TNF-α and TNF-β; granulocyte colony stimulating factor (G-CSF); granulocyte-macrophage colony stimulating factor (GM-CSF); macrophage colony-stimulating factor (M-CSF); gelsolin, erythropoietin (EPO); and thrombopoietin (TPO). The one or more inflammatory mediators can be any of a number of chemotactic cytokines (chemokines) including but not limited to CC chemokines CCL1 through CCL28 exemplified by RANTES (CCL5), MCP-1 (CCL2), LARC(CCL20), MIP-1α(CCL3), and MDC (CCL22); CXC chemokines CXCL1 through CXCL17 exemplified by LIX (CXCL5), GCP-2 (CXCL6) and BCA-1 (CXCL13); C chemokines XCL1 and XCL2; CX3C chemokine C3CL1 (fractalkine); and chemokine like molecules exemplified by MIF. Other inflammatory mediators include but are not limited to anaphylatoxin fragments C3a, C4a, and C5a from the complement pathway; leukotrienes LTA4, LTB4, LTC4, LTD4, LTE4, and LTF4; prostaglandins; growth factors EGF, FGF-9, FGF-basic, growth hormone, stem cell factor (SCF), TGF-β and VEGF; soluble receptors to tumor necrosis factor receptor (sTNFr); soluble interleukin receptors sIL-1r and sIL-2r; C-reactive protein; CD11b; histamine; serotonin; apolipoprotein A1; β2-microglobulin;

bradykinin; D-dimer; endothelin-1; eotaxin; factor VII; fibrinogen; GST; haptoglobin; IgA; insulin; IP-10; leptin; LIF; lymphotactin; myoglobin; OSM; SGOT; TIMP-1; tissue factor; VCAM-1; VWF; thromboxane; platelet activating factor (PAF); immunoglobulins; and endotoxins such as lipopolysaccharide (LPS); and various exotoxins such as superantigens, e.g., from, *Staphylococcus aureus* and *Streptococcus pyogenes*.

In an aspect, the one or more target components include exogenous chemical or biological agents that have been introduced into the blood and/or lymph of a vertebrate subject. Examples of exogenous target components include, but are not limited to, drugs, both legal and illegal, poisons, and environmental toxins. Examples of drugs commonly used to treat disease include but are not limited to anti-depressants, anti-psychotics, anti-virals, anti-fungals, anti-parasitics, anti-protozoal drugs, anti-inflammatory, antibiotics, analgesics, anti-hypertensives, statins, other cardiovascular drugs, anti-seizure drugs, muscle relaxants, hormones, steroids, chemotherapeutic agents. Examples of common illicit drugs or drugs of abuse include but are not limited to cannabinoids such as hashish and marijuana; depressants such as barbiturates, benzodiazepines (e.g., Valium, Halcion), gamma hydroxy butyrate (GHB), and methaqualone; dissociative anesthetics such as ketamine and phencyclidine (PCP); hallucinogens such as LSD, mescaline, ibogaine, and psilocybin; opioids and morphine derivatives such as codeine, fentanyl, heroin, morphine, opium, oxycodone (OxyContin) and hydrocodone bitartate/acetaminophen (Vicodin); stimulants such as amphetamines, methamphetamine, cocaine, methylphenidate (Ritalin), MDMA (ecstasy), and nicotine; and anabolic steroids (see "Commonly Abused Drugs", National Institute on Drug Abuse, www.drugabuse.gov). Examples of environmental toxins include but are not limited to lead, arsenic, mercury, phthalates. Examples of additional environmental toxins can be found in *ATSDR: Safeguarding Communities from Chemical Exposures*, Centers for Disease Control, and in the Agency for Toxic Substances & Disease Registry as part of the Centers for Disease Control, www.atsdr.cdc.gov; Wang. *J. Med. Toxicol.* 4:143-4, 2006, each of which is incorporated herein by reference.

Controlling Levels of One or More Target Components to a Target Value

A device is disclosed herein that includes one or more sensor configured to detect one or more target components in the blood fluid or lymph fluid of a vertebrate subject and configured to control levels of the one or more target components to a target value. The target value can be a desired concentration of one or more target components in the blood fluid or lymph fluid, or the target value can be a desired range of concentrations of one or more target components in the blood fluid or lymph fluid. Alternatively, the target value can be a desired ratio of concentrations of two or more target components in the blood fluid or lymph fluid. The desired ratio can be determined by a least squares fit of the concentrations of the two or more target components. The target value of a target component can be a desired concentration and/or concentration range and/or ratio of concentrations that is a specific value or range of values such as, for example, a value or range of values observed in a normal subject. Alternatively, the target value of a target component can be a desired concentration and/or concentration range and/or ratio of concentrations that is at least 20%, at least 40%, at least 60%, at least 80%, or at least 100% below or above the current level of the target component in the blood fluid or lymph fluid of a vertebrate subject.

The target value of one or more target components can include a desired concentration and/or concentration range below that observed in the blood fluid or lymph fluid of a vertebrate subject experiencing a disease, disorder, or infection. For example, a number of target components, e.g., inflammatory mediators, are elevated in the blood of subjects diagnosed with systemic immune response syndrome (SIRS) and sepsis. See, e.g., Ueda, et al., *Am. J. Respir. Grit. Care Med.* 160:132-136, 1999; Kurt, et al., *Mediators Inflamm.* 2007:31397, 2007; Kellum, et al., *Arch. Intern. Med.* 167: 1655-1663, 2007; Wang, et al., *Crit. Care* 12:R106, 2008; each of which is incorporated herein by reference. As an example, the levels of TNF-α, IL-6, and IL-8 in normal subjects is reported as less than 5 pg/ml, less than 10 pg/ml, and less than 10 pg/ml, respectively. In individuals with septic shock, the serum levels of TNF-α, IL-6, and IL-8 are significantly elevated to mean values of 138+/−22 pg/ml, 27,255+/−7,895 pg/ml, and 2,491+/−673 pg/ml, respectively. See Ueda, et al., *Am. J. Respir. Crit. Care Med.* 160:132-136, 1999; which is incorporated herein by reference.

The relative levels of one or more target components in the blood fluid or lymph fluid of a vertebrate subject can be correlated with prognosis and survival. For example, sepsis non-survivors have proportionally higher levels of inflammatory mediators relative to sepsis survivors and normal controls. In one study, high levels of both IL-10 (mean of 45 pg/ml) and IL-6 (mean of 735 pg/ml) at hospital admission were associated with increased mortality as compared with low initial levels of IL-10 (mean of 7.4 pg/ml) and IL-6 (mean of 15 pg/ml). In another example, elevated serum levels of IL-6 were correlated with sepsis symptom scores and poor outcome. These data suggest that modulating the levels of one or more inflammatory mediators to a desired target value in the blood can alter the course of the disease. See, e.g., Kellum, et al., Arch. Intern. Med. 167:1655-1663, 2007; Presterl, et al., *Am. J. Respir. Crit. Care Med.* 156:825-832, 1997; each of which is incorporated herein by reference.

The relative levels of one or more target components in the blood fluid or lymph fluid of a vertebrate subject can be correlated with a chronic disease. For example, subjects with rheumatoid arthritis have increased levels of various inflammatory mediators relative to normal subjects including IL-6 (15.8 pg/ml versus 4.0 pg/ml), TNF-α (10 pg/ml versus 3.2 pg/ml), IL-1β (129.8 pg/ml versus 57.3 pg/ml), IL-8 (9.3 pg/ml versus 2.6 pg/ml), IL-10 (15.5 pg/ml versus 4.6 pg/ml), and IL-12 (20.2 pg/ml versus 6.2 pg/ml). Psoriatic arthritis is also characterized by increased levels of circulating inflammatory mediators with statistically significant increases in the serum levels of various inflammatory mediators in subjects diagnosed with psoriatic arthritis versus normal. See, e.g., Nowlan, et al., *Rheumatology* 45:31-37, 2006; Mittal & Joshi, *J. Indian Rheumatol. Assoc.* 10:59-60, 2002; Szodoray, et al., *Rheumatology* 46:417-425, 2007, each of which is incorporated herein by reference.

The target value of one or more target components that are cells can be a desired concentration or concentration range that is below that observed in the blood fluid or lymph fluid of a vertebrate subject experiencing a disease, condition or infection. For example, elevated levels of red blood cells are associated with exposure to carbon monoxide, long-term lung disease, kidney disease, some cancers, certain forms of heart disease, liver disease. Elevated levels of platelets are associated with bleeding, iron deficiency, some diseases like cancer, or bone marrow problems. Elevated levels of neutrophils, eosinophils, and/or lymphocytes are associated with infection, malignancy and autoimmune diseases. The desired concentration or concentration range can be the concentration or concentration range observed in a normal individual. For example, the normal range of white blood cells in men and nonpregnant women ranges from 4.5 to $11\times10^9$ cells per liter while in pregnant women, the white blood cell counts range from 5.9 to $25.7\times10^9$ cells per liter depending upon whether the subject is in the first, second or third trimester or postpartum. Similarly, normal red blood cell counts range from 4.7 to $6.1\times10^{12}$ cells per liter in men, 4.2 to $5.4\times10^{12}$ cells per liter in women, 4.0 to $5.5\times10^{12}$ cells per liter in children and 4.8 to $7.1\times10^{12}$ cells per liter in newborns. Normal platelet counts range from 150 to $450\times10^9$ cells per liter for children and 150 to $400\times10^9$ cells per liter for adults. See, e.g., Rea, WebMD. Complete Blood Count (CBC) at www.webmd.com/a-to-z-guides/complete-blood-count-cbc. Last updated Sep. 12, 2008; accessed Oct. 5, 2009; incorporated herein by reference.

The target value can be a percentage range of cells in the blood. For example, of the total white blood cells in a normal subject, neutrophils range from 50% to 62%, band neutrophils range from 3% to 6%, lymphocytes range from 25% to 40%, monocytes range from 3% to 7%, eosinophils range from 0% to 3%, and basophils range from 0% to 1%.

The target value can be a desired ratio of concentrations of two or more target components in the blood fluid or lymph fluid as determined by a least squares fit of the concentration values of the two or more target components. In this instance, the levels of one or more target components can be altered to modulate the overall ratio of two or more target components. For example, levels of neutrophils relative to leukocytes is reportedly is correlated with cardiovascular risk in that increased neutrophils and/or decreased leukocytes are associated with diabetes, coronary artery disease, unstable angina, and increased risk of myocardial infarction. See, e.g., Home, et al., *J. Am. Coll. Cardiol.* 45: 1638-1643, 2005, which is incorporated herein by reference.

In some pathological states such as cancer or infection, the ideal target value of one or more target components can be zero. In the instance where a target value of zero is not attainable, the target value can be a value that reduces the symptoms and/or the disease progression. In malaria infected individuals, for example, the degree of parasitemia is correlated with the severity of the disease. The number of parasites per microliter of blood is used to assess parasitemia. For example, a subject may just be showing signs of symptoms at 100 parasites per microliter (0.002% parasitemia), severe malaria at 100,000 to 250,000 parasites per microliter (2-5% parasitemia), and near death at 500,000 parasites per microliter (10% parasitemia). Reducing parasitemia can reduce symptoms and disease severity.

Similarly, the target value of one or more target component that is a toxin or illicit drug can be zero. In the instance where a target value of zero is not attainable, the target value can be a value that reduces toxicity. For example, elevated levels of lead in the blood in adults can damage the nervous, hematologic, reproductive, renal, cardiovascular, and gastrointestinal systems. The majority of cases of lead poisoning are workplace related. The U.S. Department of Health and Human Services recommends that blood levels of lead among adults be reduced to <25 ug/dL. The highest blood levels of lead acceptable by standards of the U.S. Occupational Safety Health Administration is 40 ug/dL. The geometric mean blood levels of lead of all adults in the US is <3 ug/dL. MMWR 58(14):365-369, 2009, which is incorporated herein by reference.

Device Functioning in or Proximal to Blood and/or Lymph Vessel of a Vertebrate Subject A device is disclosed herein for treating a disease, condition or infection including at least one first reservoir that includes one or more bifunctional tags to selectively bind to one or more target components in one or more of blood fluid or lymph fluid of a vertebrate subject and at least one second reservoir disposed in at least one treatment region and configured to include one or more reactive components, wherein the one or more reactive components are configured to sequester the one or more bifunctional tags when bound to the one or more target components. The device can include one or more sensor configured to sense one or more target components in the blood fluid or lymph fluid of the vertebrate subject, a controller in communication with and responsive to the sensor, and a means for releasing one or more bifunctional tags from a first set of reservoirs responsive to the controller. The one or more bifunctional tags can be released into the blood fluid or lymph fluid of a vertebrate subject and are configured to bind one or more target components to form a bifunctional tag/target component complex. The controller can controllably adjust the release of the bifunctional tags to achieve a target value of the detected one or more target components in the blood of the subject. The device can further include a second set of reservoirs configured to bind, sequester, and optionally inactivate the bifunctional tag/target component complex. The means for sequestering and optionally inactivating the bifunctional tag/target component complex can include one or more second reservoirs configured to receive at least a portion of the blood fluid or lymph fluid through a flow route, the controller configured to control flow of blood fluid or lymph fluid through the flow route into the second reservoir, and the second reservoir including one or more reactive components configured to sequester and optionally inactivate the bifunctional tag/target component complex. The controller can control at least a portion of the blood fluid or lymph fluid through a flow route in communication with and responsive to a tag sensor configured to detect the bifunctional tag/target component complex.

The device for binding and sequestering one or more target components associated with a disease, condition or infection is in whole, or in part, configured for use in, or proximal to, one or more blood vessels and/or lymph vessels of a vertebrate subject. In an aspect, the device in part or in whole is an intra-vessel sized device (e.g., sufficiently small enough to be placed in a blood vessel and/or a lymph vessel while not necessarily obstructing flow). The device can be inserted into a blood vessel or lymph vessel. Configurations for the device include, but are not limited to, a substantially tubular structure, with one or more lumens in fluid communication with the blood vessel or lymph vessel of a vertebrate subject. In a further aspect, the device can take the form of a short cylinder, an annulus, a cylinder, and/or a spiral. See, e.g., U.S. Patent Applications 2007/0066929 and 2008/0058785; Bezrouk et al, *Scripta Medica (BRNO)* 78(4):219-226, 2005, each of which is incorporated herein by reference. In an aspect, the device has a cylindrical and hollow configuration, with a single central opening, optionally allowing the exterior of the cylindrical structure to contact and engage the wall of the vessel, and the interior of the structure (within the single central opening) to form a fluid-contacting portion of the device. For example, the device can be configured as a specialized stent fixed within a specific artery or vein. See, e.g., U.S. Pat. Nos. 5,411,551, 7,326,240; U.S. Patent Applications 2007/0294150, 2008/0281400; Yokota, et al., 22nd IEEE International Conference MicroElectro Mechanical Systems, Sorrento, Italy, January 25-29. IEEE pp. 495-499, 2009, each of which is incorporated herein by reference.

In an aspect, the device in whole or in part is configured to be approximately hemi-spherical or hemi-elliptoid, allowing a portion of its cross-section to contact and/or engage the internal wall of a blood vessel or lymph vessel without significantly and/or substantially obstructing the movement of fluid within the vessel. The device can include one or more wall engaging components including, but are not limited to, rotating wheels, projections (e.g. arms), springs, hooks (e.g. claws), suction cups, and/or tissue adhesives that are configured to engage wall portions.

In an aspect, the device can be configured in a pill- or capsule-shape, and configured to move through a central portion of a vessel. The device can engage a wall of the vessel using one or more engaging components and/or freely travel through the blood and/or lymph systems. See, e.g., U.S. Patent Application 2007/0156211 A1, which is incorporated herein by reference. The device can be targeted to a site of disease (e.g., inflammation, cancer) in the subject. In an aspect, the device can sense elevated levels of one or more target components in the blood or lymphatic system of the subject and can target and form a stationary location at, or near, a site of disease, condition or infection in the peripheral circulation of the subject. In an aspect, the implantable device can be incorporated into a shunt, for example, an arterio-venous shunt inserted between an artery and a vein.

In an aspect, the device in part or in whole is positioned proximal to a blood vessel or lymph vessel. "Proximal to" can refer to a space or area near to a blood vessel or lymph vessel. Locations that are proximal to a vessel can include, for example, locations external to the vessel wall where there is space for implanting one or more devices in whole or in part, and optionally to facilitate external access to the devices in whole or in part. In an aspect, "proximal to" can include distances such as, but not limited to, approximately 0.1, 1.0, 10, and/or 100 μms and/or approximately 0.1, 1.0, 10, and/or 100 mms, and can optionally include larger and/or smaller distances depending on, for example, the availability of space and the size of the device and/or the vessel.

In an aspect, the device is configured as a self-contained unit that includes all functionalities necessary for operation of the device. In an aspect, the system can be configured as one or more components in one or more locations separate from one another, wherein one or more of the components includes one or more essential and/or non-essential functionalities. As an example, one component of the system can be placed within a blood vessel, and another component of the system placed proximal to the blood vessel optionally in a location more accessible from the exterior of the subject, or where there is additional space. A remote portion can be configured to provide for monitoring of the vessel portion of the system, data collection, or data analysis, and/or remote-control of one or more other functions of the system such as sensing target components, controlling flow through a flow route, and releasing a reactive component. The remote portion can be at a separate location within the body of the subject, or outside the body of the subject. Data and/or power signals can be transmitted between the one or more components of the device using electromagnetic signals, or electrical or optical links.

The dimensions and mechanical properties (e.g., rigidity) of the device in part or in whole are configured for compatibility with the location of use in order to provide for reliable positioning and/or to provide for movement of the device while preventing damage to the vessel, the vessel lumen, and/or internal location and its surrounding structure. The choice of structural component size and configuration appropriate for a particular blood vessel or lymph vessel location can be selected by a person of skill in the art, optionally a medical professional. Structural components of the device can be constructed using a variety of manufacturing methods, from a variety of biocompatible materials. Appropriate materials include metals, ceramics, polymers, and composite materials having suitable biocompatibility, sterilizability, mechanical, and physical properties. Examples of materials and selection criteria are described, for example, in *The Biomedical Engineering Handbook* (Second Edition, Volume I, J. D. Bronzino, Ed., Copyright 2000, CRC Press LLC, pp. IV-1-43-22), which is incorporated herein by reference. Manufacturing techniques can include injection molding, extrusion, die-cutting, rapid-prototyping, etc., and will depend on the choice of material and device size and configuration. Sensing and energy-emitting portions of the devices as well as associated control circuitry can be fabricated on the structural elements using various microfabrication and/or MEMS techniques or can be constructed separately and subsequently assembled to the structural elements, as one or more distinct components. See, e.g., U.S. Patent Applications 2005/0221529, 2005/0121411, 2005/0126916, 2007/0066939, 2007/0225633 and Nyitrai, et al. "Preparing Stents with Masking & Etching Technology" 26$^{th}$ International Spring Seminar on Electronics Technology pp. 321-324, IEEE, 2003, each of which is incorporated herein by reference.

In additional to biocompatible materials described and incorporated herein, flexible material having adjustable diameter, taper, and length properties can be used as part of the structural material. For example, some materials can change from a longer, narrower configuration, to a shorter, wider configuration, or can taper over their length, e.g., shape-memory polymers that can move from one shape to another in response to a stimulus such as heat. Structural elements that can exhibit this type of expansion/contraction property can include self-expanding material, resilient material, and/or mesh structures formed of various metals, e.g., ionic polymer-metal composites (IPMC) or plastics, and some polymeric materials, e.g., hydrogels, nitinol, or polyester. See, e.g. Bellin et al., *Proc. Natl. Acad. Sci. USA*. 103: 18043-18047, 2006; and Shahinpoor & Kim, *Smart Mater. Struct.* 10:819-833, 2001, each of which are incorporated herein by reference.

Sensing Target Components

The device includes one or more sensors for qualitatively and/or quantitatively measuring one or more target components in the blood fluid or lymph fluid of a vertebrate subject. The one or more sensors can include, but are not limited to, one or more of a biosensor, a chemical sensor, a physical sensor, an optical sensor, or a combination thereof. The one or more sensors can include one or more target recognition elements that recognize one or more target components. The interaction of one or more target components with one or more target sensors results in one or more detectable signals sent to the controller. In response to the detectable signal, the controller controls the release of one or more bifunctional tags from the one or more first reservoirs. Preferably the one or more target sensors measure in real-time the relative number of one or more target components in the blood fluid or lymph fluid of a vertebrate subject The one or more sensors are configured to sense or detect one or more target components in the blood fluid or lymph fluid of a vertebrate subject. In an aspect, the one or more sensors are configured to sense one or more target components that are one or more cells in the blood fluid or lymph fluid of a vertebrate subject. A target component includes a cell, for example, a bacterium, a protozoan, a platelet, a red blood cell, a lymphocyte, a monocyte, a neutrophil, an eosinophil, a circulating tumor cell, or a combination thereof. The one or more target components can be sensed using any of a number of imaging or optical methods including but not limited to light scattering, electrical impedance, infrared spectroscopy, acoustic imaging, thermal imaging, photothermal imaging, dark field, visible light absorption and refraction, and autofluorescence. See, e.g., U.S. Patent Application 2009/0093728; Doornbos et al. *Cytometry* 14:589-594, 1993; Gao et al. Proceedings of the 25$^{th}$ Annual International Conference of the IEEE EMBS, Cancun, Mexico, Sep. 17-21, 2003; Oberreuter et al. *Int. J. Syst. Evol. Microbiol.* 52:91-100, 2002; Baddour et al. Ultrasonics Symposium IEEE 2:1639-1644, 2002; Zharov et al. *J. Cell. Biochem.* 97:916-932, 2006; Zharov et al. *J. Biomed. Opt.* 11:054034-1-4, 2006; Koenig et al. *J. Fluoresc.* 4:17-40, 1994; which are each incorporated herein by reference. As an example, red blood cells infected with the parasite *Plasmodium falciparum* can be differentiated from other cells in the blood using differential light scatter at 10 degrees (complexity) and polarized light scatter at 90 degrees (lobularity) based on the pigmentation of the parasite. See, e.g., Mendelow et al. *Br. J. Haematology* 104: 499-503, 1999, which is incorporated herein by reference.

In some instances, one or more target components in the blood fluid or lymph fluid of a vertebrate subject are recognized based on a spectral analysis. Alternatively, the one or more target components are recognized based on pattern and image recognition analysis. Various methods have been described for image and shape analysis of cells and subcellular components of cells. See, e.g., U.S. Pat. Nos. 5,107,422; 5,790,691; 6,956,961 B2; 7,151,847 B2; U.S. Patent Applications 2005/0251347 A1; 2006/0039593 A1; Fei-Fei et al. *IEEE Transactions on Pattern Analysis and Machine Intelligence* 28:594-611, 2006; Martin et al. *IEEE Transactions on Pattern Analysis and Machine Intelligence* 26:530-549, 2004; Olson et al. *Proc. Natl. Acad. Sci. USA* 77:1516-1520, 1980; Schneider, et al *Biorheology* 32:237-238, 1995; each of which are incorporated herein by reference. For example, a Texture Analyzing System can be used to distinguish various cells in the blood and/or lymph of a vertebrate subject based on the granularity of the cell or cells. See, e.g., Bins et al. *Cytometry* 1:321-324, 1981, which is incorporated herein by reference. The imaged components of the cells are measured with a gray scale with 33 intervals ranging from black (level 0) to white (level 99) and a histogram is generated. Mature white blood cells (neutrophils, eosinophils, basophils and lymphocytes) have a dense nuclear structure and therefore low counts. In contrast, monocytes have a looser, less dense nuclear structure and high counts. The cytoplasm of eosinophils and neutrophils is very granular and is reflected in the combination of high positive and low negative counts. Smaller values are seen in the cytoplasm of lymphocytes, monocytes and basophils. Similarly, granulometries can be used to identify red blood cells infected with the malarial parasite. See, e.g., Dempster & DiRuberto *Circuits and Systems,* 2001. ISCAS 2001. The 2001 IEEE International Symposium on May 6-9, 2001, 5:291-294, which is incorporated herein by reference.

In an aspect, the one or more sensors can include one or more target recognition elements that recognize one or more target components. The target recognition elements are configured to specifically bind one or more target components. The target recognition elements can include, but are not limited to, antibodies, antibody fragments, peptides, oligonucleotides, DNA, RNA, aptamers, protein nucleic acids, proteins, viruses, enzymes, receptors, bacteria, cells, cell fragments, inorganic molecules, organic molecules, or combinations thereof. The one or more target recognition elements can be associated with one or more substrate integrated into the one or more target sensors. Binding of a target component to a specific target recognition element activates the sensor.

In an aspect, the one or more target sensors can use Förster or fluorescence resonance energy transfer (FRET) to sense one or more target components in the blood fluid or lymph fluid of a vertebrate subject. FRET is a distance-dependent interaction between the electronic excited states of two dye molecules in which excitation is transferred from a donor molecule to an acceptor molecule without emission of a photon. In an aspect, interaction of a donor molecule with an acceptor molecule results in a shift in the emission wavelength associated with excitation of the acceptor molecule. In other aspects, interaction of a donor molecule with an acceptor molecule in results in quenching of the donor emission. The one or more target recognition elements associated with the one or more sensors can include at least one donor molecule and at least one acceptor molecule. Binding of a target component to the target recognition element results in a conformation change in the target recognition element, leading to changes in the distance between the donor and acceptor molecules and changes in measurable fluorescence. The target recognition element can be a cell, an antibody, an aptamer, a receptor or any other molecule that changes conformation or signaling in response to binding a target.

A variety of donor and acceptor fluorophore pairs can be considered for FRET associated with the target recognition element including, but not limited to, fluorescein and tetramethylrhodamine; IAEDANS and fluorescein; fluorescein and fluorescein; and BODIPY FL and BODIPY FL. A number of Alexa Fluor (AF) fluorophores (Molecular Probes-Invitrogen, Carlsbad, Calif., USA) can be paired with other AF fluorophores for use in FRET. Some examples include, but are not limited, to AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

The cyanine dyes Cy3, Cy5, Cy5.5 and Cy7, which emit in the red and far red wavelength range (>550 nm), offer a number of advantages for FRET-based detection systems. Their emission range is such that background fluorescence is often reduced and relatively large distances (>100 Å) can be measured as a result of the high extinction coefficients and good quantum yields. For example, Cy3, which emits maximally at 570 nm and Cy5, which emits at 670 nm, can be used as a donor-acceptor pair. When the Cy3 and Cy5 are not proximal to one another, excitation at 540 nm results in the emission of light by Cy3 at 590 nm only. In contrast, when Cy3 and Cy5 are brought into proximity by a conformation change in an aptamer, antibody, or receptor, excitation at 540 nm results in an emission at 680 nm. Semiconductor quantum dots (QDs) with various excitation/emission wavelength properties can also be used to generate a fluorescence based sensor.

Quenching dyes are used as part of the binder element to quench the fluorescence of visible light-excited fluorophores. Examples include, but are not limited, to DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the target recognition element including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The one or more sensor for sensing target components in the blood fluid or lymph fluid of a vertebrate subject can use the technique of surface plasmon resonance (for planar surfaces) or localized surface plasmon resonance (for nanoparticles). Surface plasmon resonance involves detecting changes in the refractive index on a sensor surface in response to changes in molecules bound on the sensor surface. In an aspect, the surface of the sensor is a glass support or other solid support coated with a thin film of metal, for example, gold. In a further aspect, the sensor surface includes a matrix to which is immobilized one or more target recognition elements that recognize one or more target components. The target recognition elements can be antibodies or fragments thereof, oligonucleotide or peptide based aptamers, receptors or ligands, artificial binding substrates formed by molecular imprinting, or any other examples of molecules and/or substrates that bind cells. As blood or blood components from the subject passes by the sensor surface, a target component can interact with a target recognition element on the sensor surface. The sensor is illuminated by monochromatic light. Resonance occurs at a specific angle of incident light. The resonance angle depends on the refractive index in the vicinity of the surface, which is dependent upon the concentration of target components on the surface. An example of instrumentation that uses surface plasmon resonance is the BIA-CORE system (Biacore, Inc.—GE Healthcare, Piscataway, N.J.) which includes a sensor microchip, a laser light source emitting polarized light, an automated fluid handling system, and a diode array position sensitive detector. See, e.g., Raghavan & Bjorkman *Structure* 3:331-333, 1995, which is incorporated herein by reference.

The one or more sensors for sensing target components can be one or more label-free optical biosensors that incorporate other optical methodologies, e.g., interferometers, waveguides, fiber gratings, ring resonators, and photonic crystals. See, e.g., Fan, et al., *Anal. Chim. Acta* 620:8-26, 2008, which is incorporated herein by reference.

The one or more sensors for sensing target components can be one or more microcantilevers. A microcantilever can act as a biological sensor by detecting changes in cantilever bending or vibrational frequency in response to binding of one or more target components to the surface of the sensor. In an aspect the sensor can be bound to a microcantilever or a microbead as in an immunoaffinity binding array. In an aspect, a biochip can be formed that uses microcantilever bi-material formed from gold and silicon, as sensing elements. See, e.g. Vashist *J. Nanotech Online* 3:DO: 10.2240/azojono0115, 2007, which is incorporated herein by reference. The gold component of the microcantilever can be coated with one or more target recognition elements which upon binding one or more target components causes the microcantilever to deflect. Aptamers or antibodies specific for one or more target components can be used to coat microcantilevers. See, e.g., U.S. Pat. No. 7,097,662, which is incorporated herein by reference. The one or more sensor can incorporate one or more methods for microcantilever deflection detection including, but not limited to, piezoresistive deflection, optical deflection, capacitive deflection, interferometry deflection, optical diffraction grating deflection, and charge coupled device. In an aspect, the one or more microcantilever can be a nanocantilever with nanoscale components. The one or more microcantilevers and/or nanocantilevers can be arranged into arrays. Both microcantilevers and nanocantilevers can find utility in microelectomechanical systems (MEMS) and/or nanoelectomechnical systems (NEMS).

The one or more sensors for sensing target components can be a field effect transistor (FET) based biosensor. In this aspect, a change in electrical signal is used to detect interaction of one or more target components with one or more target recognition elements of the sensor. See, e.g., U.S. Pat. No. 7,303,875, which is incorporated herein by reference.

The one or more sensors for sensing one or more target components can incorporate electrochemical impedance spectroscopy. Electrochemical impedance spectroscopy can be used to measure impedance across a natural and/or artificial lipid bilayer. The sensor can incorporate an artificial bilayer that is tethered to the surface of a solid electrode. One or more receptor can be embedded into the lipid bilayer. The one or more receptors can be ion channels that open and close in response to binding of a specific analyte. The open and closed states can be quantitatively measured as changes in impedance across the lipid bilayer. See, e.g., Yang, et al., IEEE SENSORS 2006, EXCO, Daegu, Korea/Oct. 22-25, 2006, which is incorporated herein by reference.

The one or more sensors can include cells with binding elements which when bound to target components induce a measurable or detectable change in the cells. The cells can emit a fluorescent signal in response to interacting with one or target components. For example, a bioluminescent bioreporter integrated circuit can be used in which binding of a ligand to a cell induces expression of reporter polypeptide linked to a luminescent response. See e.g., U.S. Pat. No. 6,673,596; Durick & Negulescu *Biosens. Bioelectron.* 16:587-592, 2001, each of which is incorporated herein by reference. Alternatively or additionally, the one or more cell can emit an electrical signal in response to interacting with one or more target components. In a further aspect, an implantable biosensor can be used which is composed of genetically modified cells that respond to target binding by emitting a measurable electrical signal. See e.g., U.S. Patent Application 2006/0234369 A1; which is incorporated herein by reference.

The one or more sensors including the target recognition elements can detect one or more target components that are non-cellular target components including but are not limited to sugars (e.g., glucose), lipids (e.g., triacylglycerols, cholesterol, phospholipids), vitamins, minerals, non-protein hormones (e.g., estrogen, testosterone), proteins (e.g., enzymes, hormones, antibodies, blood clotting factors, lipoproteins). Additional examples of proteins found in the blood and/or lymph include but are not limited to serum proteins (e.g., subclasses of immunoglobulins, complement factors, Cl esterase, circulating immune complexes, albumin, antitrypsin, fetoprotein, acid glycoprotein, alpha-macroglobulin, beta-microglobulin, ceruloplasmin, transferrin), acute phase proteins associated with disease (e.g., C-reactive protein, SPLA2, ferritin), coagulation or complement related proteins (e.g., tissue-factor pathway inhibitor, soluble tissue factor, kallikrein, factor XIIa, thrombin, lupus anticoagulant, soluble CD46, soluble CD55), and markers of cellular activation (e.g., elastase, elastase/antitrypsin complexes, lactoferrin, granzym, nucleosomes, soluble CD16, soluble CD27).

In an aspect, the one or more target sensors including the target recognition elements can detect one or more target components that are inflammatory mediators, examples of which include but are not limited to interferons (IFN) IFN-α, IFN-β, and IFN-γ; interleukins (IL) IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-27, IL-28, IL-29, IL-30, IL-31, and IL-32; tumor necrosis factor (TNF) TNF-α and TNF-β; granulocyte colony stimulating factor (G-CSF); granulocyte-macrophage colony stimulating factor (GM-CSF); macrophage colony-stimulating factor (M-CSF); gelsolin, erythropoietin (EPO); and thrombopoietin (TPO). The one or more inflammatory mediators can be any of a number of chemotactic cytokines (chemokines) including but not limited to CC chemokines CCL1 through CCL28 exemplified by RANTES (CCL5), MCP-1 (CCL2), LARC(CCL20), MIP-1a (CCL3), and MDC (CCL22); CXC chemokines CXCL1 through CXCL17 exemplified by LIX (CXCL5), GCP-2 (CXCL6) and BCA-1 (CXCL13); C chemokines XCL1 and XCL2; CX3C chemokine C3CL1 (fractalkine); and chemokine like molecules exemplified by MIF. Other inflammatory mediators include but are not limited to anaphylatoxin fragments C3a, C4a, and C5a from the complement pathway; leukotrienes LTA4, LTB4, LTC4, LTD4, LTE4, and LTF4; prostaglandins; growth factors EGF, FGF-9, FGF-basic, growth hormone, stem cell factor (SCF), TGF-β and VEGF; soluble receptors to tumor necrosis factor receptor (sTNFr); soluble interleukin receptors sIL-1r and sIL-2r; C-reactive protein; CD11b; histamine; serotonin; apolipoprotein A1; β2-microglobulin; bradykinin; D-dimer; endothelin-1; eotaxin; factor VII; fibrinogen; GST; haptoglobin; IgA; insulin; IP-10; leptin; LIF; lymphotactin; myoglobin; OSM; SGOT; TIMP-1; tissue factor; VCAM-1; VWF; thromboxane; platelet activating factor (PAF); immunoglobulins; and endotoxins such as lipopolysaccharide (LPS); and various exotoxins such as superantigens, e.g., from, *Staphylococcus aureus* and *Streptococcus pyogenes*.

In an aspect, the one or more target sensors including the target recognition elements can detect one or more target components that are exogenous chemical or biological agents that have been introduced into the blood and/or lymph of a vertebrate subject. Examples of exogenous target components include drugs, both legal and illegal, poisons, and environmental toxins. Examples of drugs can include but are not limited to anti-depressants, anti-psychotics, anti-virals, anti-fungals, anti-parasitics, anti-protozoal drugs, anti-inflammatory, antibiotics, analgesics, anti-hypertensives, statins, other cardiovascular drugs, antiseizure drugs, muscle relaxants, hormones, steroids, chemotherapeutic agents. Examples of common illicit drugs or drugs of abuse can include but are not limited to cannabinoids such as hashish and marijuana; depressants such as barbiturates, benzodiazepines (e.g., Valium, Halcion), gamma hydroxy butyrate (GHB), and methaqualone; dissociative anasthetics such as ketamine and phencyclidine (PCP); hallucinogens such as LSD, mescaline, ibogaine, and psilocybin; opioids and morphine derivatives such as codeine, fentanyl, heroin, morphine, opium, oxycodone (OxyContin) and hydrocodone bitartate/acetaminophen (Vicodin); stimulants such as amphetamines, methamphetamine, cocaine, methylphenidate (Ritalin), MDMA (ecstasy), and nicotine; and anabolic steroids (see "Commonly Abused Drugs", National Institute on Drug Abuse, www.drugabuse.gov). Examples of environmental toxins can include but are not limited to lead, arsenic, mercury, phthalates. Examples of additional environmental toxins can be found in the Agency for Toxic Substances & Disease Registry as part of the Centers for Disease Control, www.atsdr.cdc.gov; Patel, *J. Med. Toxicol.* 4:143-4, 2006, which is incorporated herein by reference.

In an aspect, the one or more sensors including the target recognition elements can sense or detect one or more target components that are target components including, but not limited to, blood cells (e.g., red blood cells, platelets, lymphocytes, monocytes, neutrophils, eosinophils, basophils), virus-infected cells (e.g., cells infected with human immunodeficiency virus (HIV), hepatitis B, hepatitis C, and hepatitis D), bacteria (e.g., *Staphylococcus, Streptococcus, Pseudomonas, Haemophilus, Listeria, Esherichia coli*), fungi, (e.g., *Candida albicans, Candida glabrata, Aspergillus, T. glabrata, Candida tropicalis, C. krusei,* and *C. parapsilosis*) parasites (e.g., *Trypanosoma cruzi, Trypanosoma brucei, Leishmania, Plasmodium, Babesia microti, Toxoplasma gondii*) and cancer cells (e.g., metastatic tumor cells, hematopoietic cancer cells).

The one or more target recognition elements are configured to recognize one or more biomolecules on the surface of the one or more target components. In an aspect, the one or more target recognition elements are configured to recognize one or more receptor types on the surface of target components. Examples of receptors include but are not limited to acetylcholine receptors, adenosine receptors, adrenoceptors, GABA receptors, angiotensin receptors, cannabinoid receptors, cholecystokinin receptors, dopamine receptors, glucagon receptors, glucocorticoid receptors, glutamate receptors, histamine receptors, mineralocorticoid receptors, olfactory receptors, opioid receptors, purinergic receptors, secretin receptors, serotonin receptors, somatostatin receptors, steroid hormone receptors, calcium-sensing receptor, hormone receptors, erythropoietin receptor, and natriuretic peptide receptors. Other examples include type I cytokine receptors (e.g., type 1 interleukin receptors, erythropoietin receptor, GM-CSF receptor, G-CSF receptor, growth hormone receptor, oncostatin M receptor, leukemia inhibitory factor receptor); type II cytokine receptors (e.g., type II interleukin receptors, interferon-α/β receptors, interferon-γ receptor); members of the immunoglobulin superfamily (e.g., interleukin-1 receptor, CSF1, c-kit receptor, interleukin-18 receptor); tumor necrosis factor (TNF) receptor family (e.g., TNF receptor 1 (TNF-R1), TNF receptor 2 (TNF-R2), CD27, CD40, and lymphotoxin β receptor); chemokine receptors including serpentine CCR and CXCR receptors (e.g., CCR1 and CXCR4, and interleukin-8 receptor); TGF β receptors. See Ozaki and Leonard, *J. Biol. Chem.* 277:29355-29358, 2002, which is incorporated herein by reference.

In a further aspect, the one or more target recognition elements are configured to recognize other biomolecules on the surface of target components including but not limited to various CD (cluster of designation/cluster of differentiation) markers, intergrins, ion channels, ATPases, cell adhesion molecules, integral membrane glycoproteins, immunoglobulins, transporters. The one or more target recognition elements are configured to recognize components of cell surface biomolecules including amino acid sequence and oligosaccharide modifications.

In an aspect, the one or more target sensors including the target recognition element can be configured to recognize a biomolecule associated with a tumor cell. Examples of tumor-associated tumor cell recognition components can include, but are not limited to, BLyS receptor, carcinoembryonic antigen (CA-125), CD25, CD34, CD33 and CD123 (acute myeloid leukemia), CD20 (chronic lymphocytic leukemia), CD19 and CD22 (acute lymphoblastic leukemia), CD30, CD40, CD70, CD133, 57 kD cytokeratin, epithelial specific antigen, epithelial cell adhesion molecule (EpCAM), extracellular matrix glycoprotein tenascin, Fas/CD95, folate receptor, gastrin-releasing peptide-like receptors, hepatocyte specific antigen, human gastric mucin, human milk fat globule, lymphatic endothelial cell marker, matrix metalloproteinase 9, melan A, melanoma marker, mesothelin, mucin glycoproteins (e.g., MUC1, MUC2, MUC4, MUC5AC, MUC6), prostate specific antigen, prostatic acid phosphatase, PTEN, renal cell carcinoma marker, RGD-peptide binding integrins, sialyl Lewis A, six-transmembrane epithelial antigen of the prostate (STEAP), TNF receptor, TRAIL receptor, tyrosinase, villin. Other tumor associated antigens include, but are not limited to, alpha fetoprotein, apolipoprotein D, clusterin, chromogranin A, myeloperoxidase, MyoD1 myoglobin placental alkaline phosphatase c-fos, homeobox genes.

In an aspect, a detectable label including tumor cell-associated recognition components can be used. Many are available from a commercial source. For example, lectins concanavalin A and wheat germ agglutinin are available conjugated to Alexa fluors, Marina Blue, AMCA, Oregon Green, tetramethylrhodamine, Texas Red, fluorescein (from, Invitrogen, Carlsbad, Calif.). Other lectins conjugated to fluorescent dyes are available including *Phaseolus vulgaris* lectin (PHA-L), *Arachis hypogaea* lectin (PNA), *Helix pomatia* agglutinin (HPA), Soybean agglutinin (SBA), and lectins from *Griffonia simplicifolia* (from, Invitrogen, Carlsbad, Calif.). Magnetic beads with an antibody to the human epithelial antigen, EpCAM (epithelial cell adhesion molecule) are commercially available (from ,e.g., Dynal Biotech, Brown Deer, Wis.). EpCAM can be used to selectively bind circulating tumor cells of epithelial origin in the blood fluid or lymph fluid of a mammalian subject. Anti-CA-125 (anti-carcinoembryonic antigen) antibodies can be used to selectively bind circulating tumor cells of ovarian cancer origin in the blood fluid or lymph fluid of a mammalian subject. Anti-CA125 antibodies can be conjugated to rhodamine-X (Invitrogen, Eugene, Oreg.). Anti-FR (anti-folate receptor) antibodies and folate-FITC, folate-Tc99m can be used to selectively bind circulating tumor cells that overexpress folate receptors, e.g., ovarian cancer cells, and circulating tumor cells in the blood fluid or lymph fluid of a mammalian subject. Endocyte, Inc., West Lafayette, Ind. See, e.g., He, et al., *Proc. Natl. Acad. Sci. USA* 104: 11760-11765, 2007, which is incorporated herein by reference.

In an aspect, the target recognition element is configured to recognize a biomolecule associated with the surface of a pathogen, e.g., bacteria, a virus-infected cell, a fungus, or a parasite. The biomolecule can be one or more components of the bacterial outer membrane, cell wall, and/or cytoplasmic membrane. Examples of components associated with the bacterial outer membrane of Gram-negative bacteria include, but are not limited to, lipopolysaccharide and OMP (outer membrane protein) porins, the latter of which are exemplified by OmpC, OmpF and PhoP of *E. coli*. Examples of components associated with the bacterial cell wall of both Gram-positive and Gram-negative bacterial include, but are not limited to, peptidoglycans polymers composed of an alternating sequence of N-acetylglucoamine and N-acetyl-muraminic acid and crosslinked by amino acids and amino acid derivatives. Examples of components associated with the bacterial cytoplasmic membrane include, but are not limited to, the MPA1-C (also called polysaccharide copolymerase, PCP2a) family of proteins, the MPA2 family of proteins, and the ABC bacteriocin exporter accessory protein (BEA) family of proteins. Other examples of components associated with bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion; channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other potential components associated with bacteria have been described in Chung, et al., *J. Bacteriology* 183:1012-1021, 2001, which is incorporated herein by reference.

In an aspect, the target recognition element is configured to recognize a biomolecule associated with a blood cell infected with a pathogen. In some instances, the target recognition element can be a biomolecule expressed on the surface of the cell that is derived from the pathogen. For example, red blood cells infected with *P. falciparum* can be distinguished from normal red blood cells by changes in surface protein expression including expression on the red blood cell surface of the parasite derived protein *P. falciparum* erythrocyte membrane protein (PfEMP1). See, e.g., Horata, et al., *Malaria J.* 8:184, 2009, which is incorporated herein by reference.

Controller in Communication with and Responsive to a Sensor The device can further include a controller that is in communication with and configured to be informed by the one or more sensors. The one or more sensors is operably coupled to the controller, either wirelessly or by circuit, and can transmit data to the controller regarding the sensed levels (relative or absolute) of one or more target components in the blood of a vertebrate subject. The controller can be integrated into the device. Alternatively, the controller can be a separate component of the device that receives and transmits data and/or commands either with or without wires. For example, an implanted device can send data regarding the sensed levels of one or more target components to an external controller through a wireless signal.

The controller can compare the input data regarding the one or more target components in the blood fluid or lymph fluid of a vertebrate subject with stored data, or the data can be stored off site and coupled either wirelessly or by circuit to the sensor and the controller. The controller itself can include the stored data. Alternatively or additionally, the controller can have access to one or more remote databases that include the stored data. The stored data can be data regarding the normal levels of one or more target components in normal or healthy subjects without a disease, condition, or infection. The stored data can further include data regarding the baseline level of one or more target components in a vertebrate subject prior to the onset of a disease, condition, or infection. The stored data can further include data regarding the level of one or more target components in a vertebrate subject at one or more previous time points. The controller assesses the most recently obtained input data with the stored data and is configured to controllably initiate steps to release an amount or amounts of one or more bifunctional tags from the one or more first reservoirs.

The device including the sensor and the controller can also be in communication with and configured to be informed by one or more tag sensors. The one or more tag sensors can transmit data to the controller regarding the presence of one or more bifunctional tag/target component complexes. In response to input data, the controller can cause the device to controllably divert all or part of the blood fluid or lymph fluid of a vertebrate subject into at least one lumen. Access to the at least one lumen can be controlled by at least one flow-modulating element. A flow-modulating element can be a gate, a valve, a louver, a splitter or flow divider, a filter, a baffle, a channel restriction, a retractable iris, or other structure that controllably limits or permits access of the blood flow to the at least one lumen and the treatment region. The controller is operably coupled, either wirelessly or by circuit, to at least one flow-modulating element. The controller can send a signal to the at least one flow-modulating element indicating whether or not all or part of the flow of blood should be diverted into the at least one lumen.

The device including the sensor and the controller can also be in communication with and configured to be informed by one or more binding sensors. The one or more binding sensors can transmit data to the controller regarding the binding of one or more bifunctional tag/target component complexes to a binding agent within one or more second reservoirs. In response to input data, the controller can further controllably initiate release or activation of one or more reactive components designed to alter, inactivate or disrupt the one or more target components. The one or more reactive components are controllably released or activated in the one or more second reservoirs of the device. In an aspect, the controller can release one or more reactive components to modulate the activity of one or more target components. Alternatively or additionally, the controller can send data regarding the levels of one or more target components in the blood of a vertebrate subject to the subject, to one or more third party individuals such as a physician or other caregiver, to a computing device, or to a combination thereof. The subject and/or caregiver or computing device can choose to initiate steps to alter, inactivate or disrupt the one or more target components by releasing or activating one or more reactive components into the circulation, into the treatment region, or a combination thereof.

The device including the controller can also include a processor or non-volatile memory structure including one or more algorithms residing on the memory that provide computational models of a disease, condition, or infection. For example, a computational model of a disease, condition, or infection can include information regarding, for example, a variety of interrelated signaling pathways involved in the disease process. The computational model can further inform decisions made by the controller. Examples of computational models related to inflammatory disease, cancer and pathogen infection have been described. See, e.g., U.S. Pat. No. 7,415, 359 B2; U.S. Patent Applications 2007/0083333 A1, 2008/0201122 A1; Vodovotz, et al., *Curr. Opin. Crit. Care.* 10:383-390, 2004; Zenker, et al., *PLoS Comput. Biol.* 3(11):e204, 2007; Li, et al., *PLoS ONE* 3(7):e2789, 2008; Vodovotz, et al., *PLoS Comput. Biol.* 4:e1000014, 2008; An, *Theoretical Biology Medical Modeling* 5:11, 2008; Lee, et al., *Proc. Natl. Acad. Sci. USA.* 104:13086-13091, 2007; Zhou, et al., *HIV Medicine.* 6:216-223, 2005, each of which is incorporated herein by reference.

Bifunctional Tags

The device includes one or more bifunctional tags stored in and released from one or more first reservoirs. The bifunctional tags are configured to bind one or more target components in the blood and/or lymph of a vertebrate subject and sequester the one or more target components in one or more second reservoirs associated with the device. Each bifunctional tag is configured to include at least one first structural element and at least one second structural element. The first and second structural elements can include one or more binding moiety configured to bind at least one of a target component and at least one of a binding agent associated with the device. In an aspect, the first and second structural elements can be any one of a detection marker, a toxin, a therapeutic agent. The one or more bifunctional tags can further include additional structural elements that are any one of an additional binding moiety, detection marker, toxin, therapeutic agent, or combination thereof. The bifunctional tag can be further armed with a cytotoxic mechanism exemplified by radioisotopes, bacterial toxins, inflammatory cytokines, chemotherapeutics, or prodrugs.

In an aspect, the first structural element and the second structural element are one or more of a binding moiety configured to bind at least one of a target component and at least one of a binding agent associated with the device. Examples of binding moieties include, but are not limited to, antibodies, antibody fragments, peptides, oligonucleotides, DNA, RNA, aptamers, protein nucleic acids, proteins, viruses, enzymes, receptors, bacteria, cells, cell fragments, inorganic molecules, organic molecules, artificial binding substrates formed by molecular imprinting or combinations thereof. The one or more binding moieties of the first structural element of the bifunctional tag and the one or more binding moieties of the second structural element of the bifunctional tag can be from the same class of binding moieties. For example, the bifunctional tag can have a first structural element binding moiety that is a first antibody and a second structural element binding moiety that is a second antibody wherein the first antibody binds a target component and the second antibody binds a binding agent associated with the device. Alternatively, the binding moiety of the first structural element of the bifunctional tag and the binding moiety of the second structural element can be from different classes of binding moieties. For example, the bifunctional tag can have a first structural element binding moiety that is an antibody and a second structural element binding moiety that is an aptamer wherein the antibody binds a target component and the aptamer binds a binding agent associated with the device, or vise versa.

The one or more binding moieties of the first or second structural element of the bifunctional tag can include one or more antibodies that bind one or more target components. Antibodies or fragments thereof for use as one or more binding moieties include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, chimeric antibodies, non-human antibodies, fully human antibodies, among others. Single chain or multiple chain antigen-recognition sites can be used. Multiple chain antigen-recognition sites can be fused or unfused. Antibodies or fragments thereof can be generated using standard methods. See, e.g., Harlow & Lane (*Antibodies: A Laboratory Manual*, Cold Spring Harbor Laboratory Press; $1^{St}$ edition 1988), which is incorporated herein by reference. Alternatively, an antibody or fragment thereof directed against one or more target component can be generated, for example, using phage display technology. See, e.g., Kupper, et al. *BMC Biotechnology* 5:4, 2005, which is incorporated herein by reference. An antibody, a fragment thereof, or an artificial antibody, e.g., Affibody® artificial antibodies (Affibody AB, Bromma, Sweden) can be prepared using in silico design (Knappik et al., *J. Mol. Biol.* 296: 57-86, 2000, which is incorporated herein by reference. In an aspect, antibodies directed against one or more target components may be available from a commercial source (from, e.g., Novus Biological, Littleton, Colo.; Sigma-Aldrich, St. Louis, Mo.; United States Biological, Swampscott, Mass.).

The one or more binding moieties of the first or second structural element of the bifunctional tag can include one or more aptamers that bind one or more target components. The aptamer can be an oligonucleotide RNA- or DNA-based aptamer. Aptamers are artificial oligonucleotides (DNA or RNA) that can bind to a wide variety of entities (e.g., metal ions, small organic molecules, proteins, and cells) with high selectivity, specificity, and affinity. Aptamers can be isolated from a large library of $10^{14}$ to $10^{15}$ random oligonucleotide sequences using an iterative in vitro selection procedure often termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374, 2005; Jayasena *Clin. Chem.* 45:1628-1650, 1999, each of which is incorporated herein by reference. In general, SELEX can be used to generate aptamers against any of a number of target components including but not limited to inflammatory mediators, cancer cells, and bacteria. See, e.g., Guthrie, et al., *Methods* 38:324-330, 2006; Shangguan, et al., *Proc. Natl. Acad. Sci. USA.* 103:11838-11843; Chen, et al., *Biochem. Biophys. Res. Commun.* 357:743-748, 2007, each of which is incorporated herein by reference.

The one or more binding moieties of the first or second structural element of the bifunctional tag can include one or more peptide based aptamers that bind one or more target components. Peptide aptamers are artificial proteins in which inserted peptides are expressed as part of the primary sequence of a structurally stable protein. See, e.g., Crawford, et al., *Brief. Funct. Genomic Proteomic* 2:72-79, 2003, which is incorporated herein by reference. Peptide aptamers can be generated by screening a target component against yeast two-hybrid libraries, yeast expression libraries, bacterial expression libraries and/or retroviral libraries. Peptide aptamers can have binding affinities comparable to antibodies.

The one or more binding moieties of the first or second structural element of the bifunctional tag can include one or more peptide receptor ligands that bind one or more target components. Examples of peptide receptor ligands include, but are not limited to, neuropeptides, for example, enkephalins, neuropeptide Y, somatostatin, corticotropin-releasing hormone, gonadotropin-releasing hormone, adrenocorticotropic hormone, melanocyte-stimulating hormones, bradykinins, tachykinins, cholecystokinin, vasoactive intestinal peptide (VIP), substance P, neurotensin, vasopressin, and calcitonin; cytokines, for example, interleukins (e.g., IL-1 through IL-35), erythropoietin, thrombopoietin, interferon (IFN), granulocyte monocyte colony-stimulating factor (GM-CSF), tumor necrosis factor (TNF), and others; chemokines, e.g., RANTES, TARC, MIP-1, MCP, and others; growth factors, for example, platelet derived growth factor (PDGF), transforming growth factor beta (TGFβ), nerve growth factor (NGF), epidermal growth factor (EGF), insulin-like growth factor (IGF), basic fibroblast growth factor (bFGF); other peptide hormones, for example, atrial natriuretic factor, insulin, glucagon, angiotensin, prolactin, oxyocin, and others.

The one or more binding moieties of the first or second structural element of the bifunctional tag can include one or more novel peptides that bind one or more target components. Novel peptides that bind selective targets can be generated, for example, using phage display methodologies. See, e.g., Spear, et al., *Cancer Gene Ther.* 8:506-511, 2001, which is incorporated herein by reference. In this aspect, the phage express novel peptides on the surface as fusion proteins in association with a phage major or minor coat protein and can be screened for binding interaction with one or more target components.

The one or more binding moieties of the first or second structural element of the bifunctional tag can include one or more receptors that bind one or more target components. All or part of a receptor can be used as a binding moiety. Examples of receptors include but are not limited to acetylcholine receptors, adenosine receptors, adrenoceptros, GABA receptors, angiotensin receptors, cannabinoid receptors, cholecystokinin receptors, dopamine receptors, glucagon receptors, glucocorticoid receptors, glutamate receptors, histamine receptors, mineralocorticoid receptors, olfactory receptors, opioid receptors, purinergic receptors, secretin receptors, serotonin receptors, somatostatin receptors, steroid hormone receptors, calcium-sensing receptor, hormone receptors, erythropoietin receptor, and natriuretic peptide receptors. Other examples include type I cytokine receptors such as type 1 interleukin receptors, erythropoietin receptor, GM-CSF receptor, G-CSF receptor, growth hormone receptor, oncostatin M receptor, leukemia inhibitory factor receptor; type II cytokine receptors such as type II interleukin receptors, interferon-α/β receptors, interferon-γ receptor; many members of the immunoglobulin superfamily such as interleukin-1 receptor, CSF1, c-kit receptor, interleukin-18 receptor; tumor necrosis factor (TNF) receptor family such as TNF receptor 1 (TNF-R1), TNF receptor 2 (TNF-R2), CD27, CD40, and lymphotoxin β receptor; chemokine receptors including serpentine CCR and CXCR receptors, such as CCR1 and CXCR4, and interleukin-8 receptor; TGF β receptors such as TGF β receptor 1 and TGF β receptor 2. See Ozaki and Leonard, *J. Biol. Chem.* 277:29355-29358, 2002, which is incorporated herein by reference In some instances, binding moieties of the first or second structural element of the bifunctional tag can include one or more cellular receptors that recognize and/or bind to bacteria. For example, CD14, which is normally associated with monocyte/macrophages is known to bind lipopolysaccharide associated with gram negative bacteria as well as lipoteichoic acid associated with the gram positive bacteria *Bacillus subtilis* (see, e.g., Fan, et al. (1999) *Infect. Immun.* 67: 2964-2968). Other examples of cellular receptors include, but are not limited to, adenylate cyclase (*Bordatella pertussis*), Gal alpha 1-4Gal-containing isoreceptors (*E. coli*), glycoconjugate receptors (enteric bacteria), Lewis(b) blood group antigen receptor (*Heliobacter pylori*), CR3 receptor, protein kinase receptor, galactose N-acetylgalactosamine-inhibitable lectin receptor, and chemokine receptor (Legionella), annexin I (*Leishmania mexicana*), ActA protein (*Listeria monocytogenes*), meningococcal virulence associated Opa receptors (Meningococcus), alpha5beta3 integrin (*Mycobacterium avium*-M), heparin sulphate proteoglycan receptor, CD66 receptor, integrin receptor, membrane cofactor protein, CD46, GM1, GM2, GM3, and CD3 (*Neisseria gonorrhoeae*), KDEL receptor (Pseudomonas), epidermal growth factor receptor (*Samonella typhiurium*), alpha5beta1 integrin (Shigella), and nonglycosylated J774 receptor (Streptococci) (see, e.g., U.S. Patent Application 2004/0033584 A1).

The one or more binding moieties of the first or second structural element of the bifunctional tag can include one or more lectins that bind one or more target components. The term "lectin" was originally used to define agglutinins which could discriminate among types of red blood cells and cause agglutination. Currently, the term "lectin" is used more generally and includes sugar-binding proteins from many sources regardless of their ability to agglutinate cells. Lectins have been found in plants, viruses, microorganisms and animals.

Because of the specificity that each lectin has toward a particular carbohydrate structure, even oligosaccharides with identical sugar compositions can be distinguished or separated. Some lectins will bind only to structures with mannose or glucose residues, while others can recognize only galactose residues. Some lectins require that the particular sugar is in a terminal non-reducing position in the oligosaccharide, while others can bind to sugars within the oligosaccharide chain. Some lectins do not discriminate between a and b anomers, while others require not only the correct anomeric structure but a specific sequence of sugars for binding. Examples of lectins include, but are not limited to, algal lectins, e.g., b-prism lectin; animal lectins, e.g., tachylectin-2, C-type lectins, C-type lectin-like, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, *selenocosmia huwena* lectin-I, Hcgp-39, Ym1; bacterial lectins, e.g., *Pseudomonas* PA-IL, *Burkholderia* lectins, *chromobacterium* CV-IIL, *Pseudomonas* PA IIL, *Ralsonia* RS-ILL, ADP-ribosylating toxin, *Ralstonia* lectin, *Clostridium* hemagglutinin, botulinum toxin, tetanus toxin, cyanobacterial lectins, FimH, GafD, PapG, Staphylococcal enterotoxin B, toxin SSL11, toxin SSL5; fungal and yeast lectins, e.g., *Aleuria aurantia* lectin, integrin-like lectin, *Agaricus* lectin, *Sclerotium* lectin, *Xerocomus* lectin, *Laetiporus* lectin, *Marasmius oreades* agglutinin, *agrocybe* galectin, *coprinus* galectin-2, Ig-like lectins, L-type lectins; plant lectins, e.g., alpha-D-mannose-specific plant lectins, *amaranthus* antimicrobial peptide, hevein, pokeweed lectin, *Urtica dioica* UD, wheat germ WGA-1, WGA-2, WGA-3, artocarpin, *artocarpus* hirsute AHL, banana lectin, Calsepa, heltuba, jacalin, *Madura pomifera* MPA, MornigaM, Parkia lectins, abrin-a, abrus agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein (see, e.g., E. Bettler, R. Loris, A. Imberty "3D-Lectin database: A web site for images and structural information on lectins" 3rd Electronic Glycoscience Conference, The interne and World Wide Web, 6-17 October 1997; http://www.cermay.cnrs.fr/lectines/

The one or more binding moieties of the first or second structural element of the bifunctional tag can include one or more artificial binding substrates formed by the process of molecular imprinting. In the process of molecular imprinting, a template, e.g., target component, is combined with functional monomers which upon cross-linking form a polymer matrix that surrounds the template. See Alexander, et al., *J. Mol. Recognit.* 19:106-180, 2006, which is incorporated herein by reference. Removal of the template leaves a stable cavity in the polymer matrix that is complementary in size and shape to the template. In an aspect, functional monomers of acrylamide and ethylene glycol dimethacrylate can be mixed with one or more target components in the presence of a photoinitiator and ultraviolet irradiation used to cross-link the monomers. The resulting polymer can be crushed or ground into smaller pieces and washed to remove the one or more target components, leaving a particulate matrix material capable of binding one or more target components. Examples of other functional monomers, cross-linkers and initiators can be used to generate an artificial binding substrate are provided. See, e.g., U.S. Pat. No. 7,319,038; Alexander, et al., *J. Mol. Recognit.* 19:106-180, 2006, each of which is incorporated herein by reference. In a further aspect, hydrogels can be used for molecular imprinting. See, e.g., Byrne et al., "Molecular imprinting within hydrogels", *Advanced Drug Delivery Reviews,* 54: 149-161, 2002, which is incorporated herein by reference. Other examples of synthetic binders are provided. See, e.g., U.S. Pat. Nos. 6,255,461; 5,804,563; 6,797,522; 6,670,427; and 5,831,012; and U.S. Patent Application 20040018508; and Ye and Haupt, *Anal Bioanal Chem.* 378: 1887-1897, 2004; Peppas and Huang, *Pharm Res.* 19: 578-587 2002, each of which is incorporated herein by reference.

A bifunctional tag configured with two or more structural elements can be constructed using a variety of methods including but not limited to one or more chemical cross-links, one or more streptavidin/biotin interactions, one or more fusion protein constructs, one or more binding to a common substrate, or a combination thereof. In an aspect, the two or more structural elements are directly associated with one another through chemical cross-linking, non-covalent linking, or synthesis as a single molecule. In an aspect, the two or more structural elements are indirectly associated. In this instance, the two or more structural elements are separately attached to a mobile substrate such as, for example, a bead or other particle-like substrate capable of being released into the blood fluid or lymph fluid of a subject. The particle-like substrate can include a bead, a vesicle, a cell, a carbon nanotube, or other similar structures.

A bifunctional tag configured with two or more structural elements can be constructed by cross-linking the two or more structural elements to one another. For example, two antibodies with different specificities can be cross-linked together to form a bifunctional tag using a chemical cross-linking agent, e.g., N-succinimidyl 3-(2-pyridyldithio)propionate (SPDP). See, e.g., U.S. Pat. No. 5,470,570, which is incorporated herein by reference. Any of a number of homobifunctional, heterofunctional, and/or photoreactive cross linking agents can be used to cross-link two or more structural elements of a bifunctional tag. Examples of homobifunctional cross linkers include, but are not limited to, primary amine/primary amine linkers such as BSOCES ((bis(2-[succinimidooxy-carbonyloxy]ethyl) sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2'pyridyldithio]-propionamido) butane). Examples of heterofunctional cross linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-gamma-maleimidobutyryl-oxysuccinimide ester), Sulfo GMBS (N-γ-maleimidobutyryloxysulfosuccinimide ester), EMCS(N-(epsilon-maleimidocaproyloxy) succinimide ester), Sulfo EMCS(N-(epsilon-maleimidocaproyloxy) sulfo succinimide), SIAB (N-succinimidyl(4-iodoacetyl)aminobenzoate), SMCC (succinimidyl 4-(N-maleimidomethyl) cyclohexane-1-carboxylate), SMPB (succinimidyl 4-(rho-maleimidophenyl) butyrate), Sulfo SIAB (N-sulfosuccinimidyl(4-iodoacetyl)aminobenzoate), Sulfo SMCC (sulfosuccinimidyl 4-(N-maleimidomethyl)cyclohexane-1-carboxylate), Sulfo SMPB (sulfosuccinimidyl 4-(rho-maleimidophenyl) butyrate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH (N-(epsilon-maleimidocaproic acid) hydrazide); and amine/carboxyl linkers such as EDC (1-ethyl-3-(3-dimethylaminopropyl) carbodiimide hydrochloride).

A bifunctional tag configured with two or more structural elements can be constructed using one or more interactions between biotin and avidin, streptavidin or derivatives thereof. Streptavidin and avidin are multivalent proteins capable of binding multiple biotin subunits with high affinity and as such can be used as linking molecules between two biotinylated structural elements. An aptamer or antibody structural element directed against one or more target components can be linked to a second structural element of a bifunctional tag using a streptavidin-biotin bridge. For example, a biotinylated aptamer can be linked to a biotinylated antibody through a streptavidin bridge. An aptamer portion of the bifunctional tag can be biotinylated by introducing a biotinylated nucleotide into the aptamer sequence during in vitro transcription. An antibody portion of the bifunctional tag can be biotinylated using an amine reactive biotinylation reagent such as, for example, EZ-Link Sulfo-NHS-SS-Biotin (sulfosuccinimidyl 2-(biotinamido)-ethyl-1,3-dithiopropionate; Pierce-Thermo Scientific, Rockford, Ill., USA. See e.g., Jaiswal, et al. Nature Biotech. 21:47-51, 2003, which is incorporated herein by reference. The biotinylated aptamer is reacted with the biotinylated antibody in the presence of streptavidin to generate the bifunctional tag. Alternatively, a first structural element of the bifunctional tag can contain all or part of the streptavidin protein for use in binding to a biotin-modified second structural element. For example, cDNA sequence encoding all or part of an antibody or other protein/peptide can be genetically modified to contain all or part of the streptavidin gene using standard cloning procedures, resulting in a streptavidin-antibody fusion protein. See, e.g., Koo, et al. Appl. Environ. Microbiol. 64:2497-2502, 1998, which is incorporated herein by reference.

A bifunctional tag configured with two or more structural elements can be constructed by association of two non-covalently associated single-chain antibodies. In one aspect, protein engineering methodologies are used to generate the variable domains of two distinct antibodies (A and B) and are arranged as VHa-VLb (variable heavy chain domain of antibody A and variable light chain domain of antibody B) on one chain and VHb-VLa (variable heavy chain domain of antibody B and variable light chain domain of antibody A) on the other chain to generate diabody structures with two distinct binding affinities. See, e.g., Takemura, et al., Protein Eng. Des. Sel. 13:583-588, 2000, which is incorporated herein by reference. The bifunctional tags generated from two distinct antibody variable domains can be further covalently cross-linked with disulfide bonds for added stability and to enable addition of a third structural element such as a radiolabel or fluorescent tag. See, e.g., Olafsen, et al., Protein Eng. Des. Sel. 17:315-323, 2004, which is incorporated herein by reference. A number of other methods have been described for generating antibody-like biomolecules with two or more distinct binding specificities. See., e.g., U.S. Pat. No. 4,444,878; U.S. Patent Application 2009/0182127; Kufer, et al., Trends Biotechnol. 22:238-244, 2004; Stork, et. al., Protein Eng. Des. Sel. 20:569-576, 2007, each of which is incorporated herein by reference.

A bifunctional tag configured with two or more structural elements can be constructed by generating a fusion protein. In this instance, cDNA encoding the two or more structural elements are incorporated into an appropriate expression construct to generate a protein expression product that includes amino acid sequence from each structural element and retains the binding properties of each structural element . In an aspect, the bifunctional tag includes first structural element that is an antibody and a second structural element that is streptavidin. See, e.g., Koo, et al. Appl. Environ. Microbiol. 64:2497-2502, 1998, which is incorporated herein by reference. In an aspect, the bifunctional tag includes a first structural element that is an antibody and a second structural element that is a receptor ligand. See, e.g., Becker, et al., Proc. Natl. Acad. Sci. USA. 93:7826-7831, 1996; Challita-Eid, et al., J. Immunol. 160:3419-3426, 1998, each of which is incorporated herein by reference. In a further aspect, the bifunctional tag includes a first structural element that is a first receptor ligand and a second structural element that is a second receptor ligand. See, e.g., U.S. Pat. No. 6,132,992, which is incorporated herein by reference.

Sensing Occupied Versus Unoccupied Bifunctional Tags

The bifunctional tag can be further configured to controllably emit a signal in response to binding a target component. In an aspect, the one or more bifunctional tags are configured to emit a signal only when a target component is bound. Alternatively, the one or more bifunctional tags are configured to emit a first signal in the absence of a bound target component and a second signal in the presence of a bound target component.

In an aspect, the bifunctional tag can be configured such that binding of the target component to the tag results in a conformational change in the bifunctional tag that can be measured using fluorescence resonance energy transfer (FRET). FRET is a distance-dependent interaction between the electronic excited states of two dye molecules in which excitation is transferred from a donor molecule to an acceptor molecule without emission of a photon. In an aspect, interaction of a donor molecule with an acceptor molecule can lead to a shift in the emission wavelength associated with excitation of the acceptor molecule. In other aspects, interaction of a donor molecule with an acceptor molecule can lead to quenching of the donor emission. The one or more structural elements of the bifunctional tag can include at least one donor molecule and at least one acceptor molecule. In this configuration, binding of one or more target components to the bifunctional tag results in a conformational change in the bifunctional tag and results in a change in the distance between the donor and acceptor molecules and a change in measurable fluorescence.

A variety of donor and acceptor fluorophore pairs can be considered for FRET associated with the bifunctional tag including, but not limited to, fluorescein and tetramethylrhodamine; IAEDANS and fluorescein; fluorescein and fluorescein; and BODIPY FL and BODIPY FL. A number of Alexa Fluor (AF) fluorophores (Molecular Probes-Invitrogen, Carlsbad, Calif., USA) can be paired with other AF fluorophores for use in FRET. Some examples include, but are not limited, to AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

The cyanine dyes Cy3, Cy5, Cy5.5 and Cy7, which emit in the red and far red wavelength range (>550 nm), offer a number of advantages for FRET-based detection systems. Their emission range is such that background fluorescence is often reduced and relatively large distances (>100 Å) can be measured as a result of the high extinction coefficients and good quantum yields. For example, Cy3, which emits maximally at 570 nm and Cy5, which emits at 670 nm, can be used as a donor-acceptor pair. When the Cy3 and Cy5 are not proximal to one another, excitation at 540 nm results only in the emission of light by Cy3 at 590 nm. In contrast, when Cy3 and Cy5 are brought into proximity by a conformation change in an aptamer, antibody, or receptor, for example, excitation at 540 nm results in an emission at 680 nm.

Quenching dyes are used as part of the bifunctional tag to quench the fluorescence of visible light-excited fluorophores. Examples of quenching dyes include, but are not limited to, DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the bifunctional tag including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The bifunctional tag can include at least one structural element that is an RNA or DNA oligonucleotide-based aptamers with one or more fluorescent tags and one or more quenching tags. Upon binding of a target component, the aptamer undergoes a conformational shift such that the distance between the donor fluorophore and the acceptor fluorophore or quencher is altered, leading to a change in measurable fluorescence. Aptamers can be isolated from a large library of $10^{14}$ to $10^{15}$ random oligonucleotide sequences using an iterative in vitro selection procedure often termed "systematic evolution of ligands by exponential enrichment" (SELEX). Aptamers can be generated against virtually any class of molecules including cells (e.g., cancer cells, bacteria, and parasites), proteins (e.g., hormones), and chemicals (e.g., codeine, cocaine). See, e.g., Shangguan, et al., *Proc. Natl. Acad. Sci. USA*. 103:11838-11843; Chen, et al., *Biochem. Biophys. Res. Commun.* 357:743-748, 2007; Ulrich, et al., *J. Biol. Chem.* 277:20756-20762, 2002; Cao, et al. *Current Proteomics* 2:31-40, 2005; Proske, et al. *Appl. Microbiol. Biotechnol.* 69:367-374, 2005, Win, et al. *Nucleic Acids Res.* 34:5670-5682, 2006, each of which is incorporated herein by reference. For example, an aptamer that selectively binds cocaine can be generated using SELEX as described above and modified to incorporate a fluorophore such as, for example, fluorescein and a quencher such as, for example, 4-[4'-((dimethylamino)phenyl)azo-] benzoic acid (DABCYL). See, e.g., Stojanovic, et al. *J. Am. Chem. Soc.* 123: 4928-4931, 2001, which is incorporated herein by reference. In this instance, binding of cocaine to the aptamer induces a conformational change in the aptamer that causes the fluorophore and the quencher to move closer in proximity. As such, the presence of cocaine can be measured as a function of the decrease in or quenching of the fluorescein emission at a wavelength of 518 nm.

Semiconductor quantum dots (QDs) with various excitation/emission wavelength properties can be used to label an aptamer structural element of a bifunctional tag. Various methods are available for attaching quantum dots to the DNA backbone of an aptamer such as, for example, covalent linkage of amino-labeled DNA to carboxylated QDs and linkage of biotinylated DNA to streptavidin modified QDs. See, e.g., Cady, et al. *J. Mol. Cell. Probes* 21:116-124, 2007, which is incorporated herein by reference. For example, carboxy QDs (from, e.g., Quantum Dot Corporation, Hayward, Calif., USA) can be attached to an aptamer through a C6 amino modifier placed on either the 5 prime or 3 prime end of the aptamer sequence. Alternatively, streptavidin QDs (from, e.g., Quantum Dot Corporation, Hayward, Calif., USA) can be attached to an aptamer through a biotin attached to the 5-prime end of the aptamer sequence.

The fluorophores can be attached to various chemical moieties that allow for attachment at various sites within the aptamer. For example, 3'-DABCYL CPG can be used to place the fluorophore DABCYL at the 3 prime terminus of the aptamer whereas 5'-DABCYL phosphoramidite can be used to place DABSYL at the 5 prime terminus of the aptamer (see, e.g., product information at Glen Research, Sterling, Va.). DABCYL dT can be used to place DABCYL within the body of the aptamer sequence. Labeling aptamers with appropriate commercially available fluorophores can be achieved following instructions provided by the respective manufacturer. Alternatively, custom made aptamer-based molecular beacons are available from commercial sources (from, e.g., Biosearch Technologies, Inc., Novato, Calif., USA).

In some instances, an aptamer can have a fluorophore in a region of the molecule known to undergo conformational change upon binding of a target that leads to an increase in fluorescence intensity. An aptamer of this sort can be selected using an in vitro selection process with fluorescently labeled aptamers. See, e.g., Jhaveri, et al. *Nature Biotech.* 18:1293-1297, 2000, which is incorporated herein by reference. A pool of RNA molecules is generated in which the random sequence region (45-60 residues) is skewed such that one of the residues, uridine, for example, is disproportionately underrepresented. The three to four randomly placed uridine residues are substituted with fluorescein-12-UTP, Cascade Blue-7-UTP, Texas Red-5-UTP, and/or Rhodamine Green-5-UTP during in vitro transcription. The labeled pool of RNA molecules are screened against a target component by passing the labeled pool over a column matrix or other matrix to which the target component is attached. Those RNA molecules that bind with high affinity to the target component are further screened for their fluorescence signaling properties in response to binding of the target component. For example, the baseline fluorescence intensity is measured for RNA aptamer molecules labeled with fluorescein-12-UTP (excitation maxima 494 nm, emission maxima 521 nm) or Rhodamine Green-5-UTP (excitation maxima 505 nm, emission maxima 533 nm), for example, then re-measured in response to increasing concentrations of the target component. Fluorescent aptamers can be selected that exhibit a 100-200% increase in fluorescence intensity in response to target binding. See, e.g., Jhaveri, et al. *Nature Biotech.* 18:1293-1297, 2000, which is incorporated herein by reference.

In an aspect, the bifunctional tag can include at least one structural element that is an antibody with one or more donor fluorophore and one or more acceptor fluorophore or quencher. Upon binding of a target component, the antibody undergoes a conformational shift such that the distance between the donor fluorophore and the acceptor fluorophore or quencher is altered, leading to a change in measurable fluorescence. The antibody can be designed to emit a shift in emission wavelength, for example, in response to binding a target component. An antibody that exhibits a shift in fluorescent signal in response to binding of an antigen can be generated by labeling the antibody with a solvent-sensitive fluorophore, e.g., dansyl chloride (5-dimethylaminonaphthalene-1-sulfonyl chloride). See, e.g., Brennan *J. Fluor.* 9:295-312, 1999, which is incorporated herein by reference. The antibody is labeled such that binding of the target component to the antibody shields the solvent sensitive fluorescent label near the active binding site from the solvent water, resulting in a 3-5 fold increase in fluorescence intensity. See, e.g., Bright, et al. *Anal. Chem.* 62:1065-1069, 1990, which is incorporated herein by reference.

In an aspect, the bifunctional tag can include at least one structural element that is an antibody that signals binding of a target component using FRET and a flexible arm. For example, an antibody can include a donor fluorophore near the binding site or the target component as well as a flexible arm containing an analog of the target component that is labeled with a quencher and recognized by the antibody. See, e.g. U.S. Patent Application 2006/0172318 A1, which is incorporated herein by reference. As the labeled target component analog moves into proximity to the labeled active site, a baseline FRET signal can be measured. A measurable change in the FRET signal is detected when the analog is competitively displaced by the actual target component. The flexible arm can be composed of DNA, RNA, polymers, protein nucleic acid (PNA), peptides, protein or oligosaccharide. For example, an amino functionalized DNA arm can be treated with a bifunctional NHS-ester activated Cy3.5 dye to add a fluorescent tag to the flexible arm. The analog of the target component is modified with a monoamine and interacted with the bifunctional NHS-ester and attached to the DNA flexible arm. See, e.g., U.S. Patent Application 2006/0172318 A1, which is incorporated herein by reference. The flexible arm can be attached directly to the antibody through a thiol-maleimide linkage such that the DNA flexible arm is modified with a thiol group at one end and linked via maleimide to one or more cysteine groups on the antibody. Alternatively, the flexible arm can be attached to a protein, for example, that is adjacent to the antibody or to which the antibody is bound.

The device can periodically emit electromagnetic energy sufficient to excite the fluorophores associated with, for example, an aptamer or antibody on a bifunctional tag and as such measure emitted fluorescence. The excitation and emission wavelengths used can range from 320 nm to 1000 nm, depending upon the fluorophores used. For example, Cy5 is excited at 649 nm and has a maximum emission at 670 nm. The light source can be a broad band white light source filtered to provide the appropriate excitation wavelength. Alternatively, the light source can be a laser such as, for example, gas lasers, eximer lasers, solid state lasers, and dye lasers. In some instances, one or more laser diodes, for example, can be incorporated into the device. A charge coupled device (CCD) or other light capturing device can be used to detect the emitted fluorescence.

First Reservoirs for Storing and Releasing Bifunctional Tags

The device includes one or more first reservoirs configured to store and controllably release one or more bifunctional tags. In an aspect, the device includes a single first reservoir configured to store one or more bifunctional tags. In an aspect, the device includes multiple first reservoirs wherein each multiple first reservoir is configured to store one or more bifunctional tags. The one or more first reservoirs can be an integral part of the device. Alternatively, the one or more first reservoirs can be a separate part of the device, located proximal to or at a distance from the main body of the device, but in wireless communication with the main body of the device.

Release of one or more bifunctional tags from the one or more first reservoirs can be facilitated by one or more release mechanisms. In an aspect, the bifunctional tags can be continuously released from at least one first reservoir at a constant rate over time. For example, the release mechanism can use one or more of a slow release, controlled release, or extended release biodegradable composition that dissolves or breaks down over time. Examples of slow release, controlled release, or extended release compositions include but are not limited to hydrogels, polymers, gelled and/or cross-linked water swellable polyolefins, polycarbonates, polyesters, polyamides, polyethers, polyepoxides and polyurethanes such as, for example, poly(acrylamide), poly(-hydroxyethyl acrylate), poly(2-hydroxypropyl acrylate), poly(N-vinyl-2-pyrrolidone), poly(n-methylol acrylamide), poly(diacetone acrylamide), poly(-hydroxylethyl methacrylate), poly(allyl alcohol). Other suitable polymers include but are not limited to cellulose ethers, methyl cellulose ethers, cellulose and hydroxylated cellulose, methyl cellulose and hydroxylated methyl cellulose, gums such as guar, locust, karaya, xanthan gelatin, and derivatives thereof. The rate of dissolution of the composition containing the bifunctional tag can be monitored using an impedance-based sensor as described by Johnson et al., in *J. Electrochem Soc.* 152:H6-H11, 2005, which is incorporated herein by reference.

In an aspect, the one or more bifunctional tags can be controllably released from the one or more first reservoirs and can include periods of release followed by periods of non-release. Controlled release from one or more first reservoirs can include a release mechanism that reversibly opens and closes a portion of the first reservoir. The release mechanism can include a variety of different types of release mechanisms, including, for example, a controllable valve. Various examples of micro valves or microelectromechanical systems (MEMS) valves for controlling fluid flow have been described. See, e.g., Luckevich M. *Valve World*, May 2007, pp. 79-83; Givrad TK., et al., *Proceedings of BIOMed2008, 3rd Frontiers in Biomedical Devices Conference*. Jun. 18-20, 2008, Irvine, Calif., USA; U.S. Pat. Nos. 6,612,535; 7,124,773, each of which is incorporated herein by reference.

In an aspect, the one or more first reservoirs are covered with a material that can be controllably removed or punctured to release one or more bifunctional tags. The cover material can be responsive to a directly applied stimulus (e.g., an applied voltage or potential) or to a change in the local environment of the device (e.g., local pH change), or any of a number of other stimuli including but not limited to heat, light (e.g., laser), and magnetic field. See, e.g., U.S. Pat. No. 6,808,522; Grayson, R. et al., *Proceedings of IEEE* 92:6-21, 2004, which are each incorporated herein by reference. As an example, the one or more first reservoirs can be an array of microreservoirs on a microchip in which each aliquot of one or more bifunctional tags is contained in its own reservoir and capped by an environmentally sensitive material. In one aspect, the microreservoirs can be capped with a gold membrane which is weakened and ruptured by electrochemical dissolution in response to application of an anode voltage to the membrane in the presence of chloride ions, resulting in release of drug as described in U.S. Pat. No. 5,797,898 and in Prescott, et al., *Nat. Biotech.*, 24:437-438, 2006, each of which is incorporated herein by reference. Alternatively, the microreservoirs can be capped by a temperature sensitive material which can be ruptured in response to selective application of heat to one or more of the reservoirs as described in U.S. Pat. No. 6,669,683, which is incorporated herein by reference. Wireless induction of a voltage or thermal trigger, for example, to a given reservoir of a microarray of reservoirs by a subject would enable on-demand release of one or more bifunctional tags.

In some instances, the one or more first reservoirs of the device can incorporate a natural and/or synthetic stimulus-responsive hydrogel or polymer which changes confirmation rapidly and reversibly in response to environmental stimuli such as, for example, temperature, pH, ionic strength, electrical potential, light, magnetic field or ultrasound. See e.g., Stubbe, et al., *Pharmaceutical Res.*, 21:1732-1740, 2004, which is incorporated herein by reference. Examples of polymers are described in U.S. Pat. Nos. 5,830,207; 6,720,402; and 7,033,571, each of which is incorporated herein by reference. In some instances, the one or more bifunctional tags can be dissolved or dispersed in the hydrogel or polymer. Alternatively, a hydrogel and/or other stimulus-responsive polymer can be incorporated into the release mechanism. For example, a hydrogel or other polymer or other smart material can be used as an environmentally sensitive actuator to control flow of a therapeutic agent out of an implantable device as described in U.S. Pat. Nos. 6,416,495; 6,571,125; and 6,755,621, each of which is incorporated herein by reference. The one or more first reservoirs can incorporate a hydrogel or other polymer that modulates delivery of one or more bifunctional tags in response to a trigger from the sensor-informed controller.

In some instances, release of one or more bifunctional tags from the first reservoirs can be nonprogammable, delivered as a predetermined dosage. For example, the one or more bifunctional tags can be administered using continuous infusion. Alternatively, the release of one or more bifunctional tag from the first reservoirs can be linked to a timing mechanism associated with the device. For example, the timing mechanism can instruct release of one or more bifunctional tags at a given time of day, a given time of week, a given time of month, and/or a given time of year. The timing mechanism can be further linked to input from the one or more sensors, releasing one or more bifunctional tag at one or more predetermined time following detection of one or more target components.

The release of one or more bifunctional tags from the first reservoirs can be programmable, having on/off and/or variable delivery rates based on either external or internal control. External control can be mediated by manual manipulation of a hand-operated pulsative pump with one-way valves associated with a device implanted near the surface of the skin, for example. Alternatively, external control can be mediated by remote control through an electromagnetic wireless signal such as, for example, infrared or radio waves that are able to trigger an electrical stimulus within the implanted device. Examples of remote control drug delivery devices are described in U.S. Pat. Nos. 5,928,195; 6,454,759; and 6,551,235, each of which is incorporated herein by reference. As such, one or more bifunctional tag can be delivered by continuous infusion in response to an "on" trigger and stopped in response to an "off" trigger, for example. Alternatively, one or more bifunctional tag can be delivered as a microbolus, for example, in response to an "on" trigger as described in U.S. Pat. No. 6,554,822, which is incorporated herein by reference. External control can be initiated by a caregiver. Alternatively, a subject can initiate delivery of one or more bifunctional tag. As such, the system can have a built in mechanism to limit the number of allowable doses by a subject and/or caregiver in a given time frame as described, for example, in U.S. Pat. No. 6,796,956, which is incorporated herein by reference.

Binding of Bifunctional Tag in Second Reservoir

The device disclosed herein further includes one or more second reservoirs. The one or more second reservoirs are configured to bind and sequester one or more target components by selectively capturing bifunctional tags to which are bound one or more target components. The one or more second reservoirs can include one or more reactive components that are binding agents configured to bind one or more structural elements of a bifunctional tag. The one or more binding agents can be used alone to selectively or non-selectively sequester one or more bifunctional tags. Alternatively, the one or more binding agents can be used to capture one or more bifunctional tag in combination with treatment including one or more additional reactive components, e.g., a denaturing agent, a degradative agent, a cell-disrupting agent, a modulator, an energy source, an apoptotic agent, a programmed cell death-inducing agent, a cytotoxic agent, cytostatic agent, a chemotherapeutic agent, an antibody toxin or a combination thereof. Following binding of the one or more bifunctional tags to the one or more binding agents in a second reservoir, one or more additional reactive components can be provided to inactive the one or more target components bound to the bifunctional tag.

The one or more binding agents can include absorbent or adsorbent material that non-selectively binds one or more bifunctional tags. The absorbent or adsorbent material can include, but is not limited to, silica, activated charcoal, non-ionic or uncharged resins or polymers, ionic or charged resins or polymers, anion exchange resins or polymers, cation exchange resins or polymers, neutral exchange resins or polymers, immobilized polymyxin B, immobilized monoclonal antibodies, immobilized inflammatory mediator receptors, immobilized specific antagonists, cellulose, cellulose derivatives, synthetic materials, polysulfone, polyacrylonitrile, polymethylmethacrylate, polyvinyl-alcohol, polyamide, polycarbonate, polystyrene-derivative fibers, and any combination thereof. Specific examples of absorbent or adsorbent materials that have been used in animal and clinical studies for non-specific binding of inflammatory mediators, for example, include, but are not limited to, polystyrene-divinylbenzene copolymer beads with biocompatible polyvinylpyrrolidone coating (CYTOSORB, MedaSorb Corporation, NJ, USA) and 2-methacryloyloxyethyl phosphorylcholine (MPCF-X; see, e.g., Nakada, et al., *Transfus. Apher. Sci.* 35:253-264, 2006, which is incorporated herein by reference.

In an aspect, the one or more binding agents can include one or more biomolecules that non-specifically bind immunoglobulins, examples of which include anti-immunoglobulin antibodies, Protein A and Protein G. In a further aspect, the binding agent can be avidin or streptavidin for binding biotinylated bifunctional tags. Alternatively, the binding agent can be biotin for binding avidin or streptavidin labeled bifunctional tags.

The one or more binding agents can selectively bind one or more structural elements of the bifunctional tag. A selective binding agent can include, but is not limited to, an antibody or fragments thereof, an oligonucleotide or peptide based aptamer, a receptor or parts thereof, a ligand, an artificial binding substrate formed by molecular imprinting, or combinations thereof. The reactive components can further include one or more of an adhesion molecule, a binding mimetic, a polymer, a lectin, integrin, or selectin. In some instances, the one or more structural elements of the bifunctional tag is itself an antibody or fragments thereof, an oligonucleotide or peptide based aptamer, a receptor or parts thereof, a ligand, an artificial binding substrate formed by molecular imprinting, or combinations thereof, in which case, the binding agent can be an antigen, an epitope, a binding partner, a receptor, a ligand, and the like.

The one or more binding agents can include one or more antibodies that bind one or more structural elements of the bifunctional tag. Antibodies or fragments thereof for use as one or more binding agents include, but are not limited to, monoclonal antibodies, polyclonal antibodies, Fab fragments of monoclonal antibodies, Fab fragments of polyclonal antibodies, Fab$_2$ fragments of monoclonal antibodies, and Fab$_2$ fragments of polyclonal antibodies, chimeric antibodies, non-human antibodies, fully human antibodies, among others. Single chain or multiple chain antigen-recognition sites can be used. Multiple chain antigen-recognition sites can be fused or unfused. Antibodies or fragments thereof can be generated using standard methods. See, e.g., Harlow & Lane (*Antibodies: A Laboratory Manual,* Cold Spring Harbor Laboratory Press; 1$^{st}$ edition 1988), which is incorporated herein by reference. Alternatively, an antibody or fragment thereof directed against one or more inflammatory mediators can be generated, for example, using phage display technology. See, e.g., Kupper, et al. *BMC Biotechnology* 5:4, 2005, which is incorporated herein by reference. An antibody, a fragment thereof, or an artificial antibody, e.g., Affibody® artificial antibodies (Affibody AB, Bromma, Sweden) can be prepared using in silico design (Knappik et al., *J. Mol. Biol.* 296: 57-86, 2000, which is incorporated herein by reference.

The one or more binding agents can include one or more aptamers that bind one or more structural elements of the bifunctional tag. The aptamer can be an oligonucleotide RNA- or DNA-based aptamer. Aptamers are artificial oligonucleotides (DNA or RNA) that can bind to a wide variety of entities (e.g., metal ions, small organic molecules, proteins, and cells) with high selectivity, specificity, and affinity. Aptamers can be isolated from a large library of $10^{14}$ to $10^{15}$ random oligonucleotide sequences using an iterative in vitro selection procedure often termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374, 2005; Jayasena *Clin. Chem.* 45:1628-1650, 1999, each of which is incorporated herein by reference.

In an aspect, the one or more binding agents can include one or more aptamers that are peptide based aptamers. Peptide aptamers are artificial proteins in which inserted peptides are expressed as part of the primary sequence of a structurally stable protein. See, e.g., Crawford, et al., *Brief Funct. Genomic Proteomic* 2:72-79, 2003, which is incorporated herein by reference. Peptide aptamers can be generated by screening the one or more structural elements of the bifunctional tag against yeast two-hybrid libraries, yeast expression libraries, bacterial expression libraries and/or retroviral libraries. Peptide aptamers can have binding affinities comparable to antibodies.

In a further aspect, the one or more binding agents can include one or more novel peptides. Novel peptides that bind selective targets can be generated, for example, using phage display methodologies. See, e.g., Spear, et al., *Cancer Gene Ther.* 8:506-511, 2001, which is incorporated herein by reference. In this aspect, the phage express novel peptides on the surface as fusion proteins in association with a phage major or minor coat protein and can be screened for binding interaction with one or more structural element of the bifunctional tag.

The one or more binding agents can include one or more artificial binding substrates formed by the process of molecular imprinting and configured to bind one or more structural elements of the bifunctional tag. In the process of molecular imprinting, a template is combined with functional monomers which upon cross-linking form a polymer matrix that surrounds the template. See Alexander, et al., *J. Mol. Recognit.* 19:106-180, 2006, which is incorporated herein by reference. Removal of the template leaves a stable cavity in the polymer matrix that is complementary in size and shape to the template. In an aspect, functional monomers of acrylamide and ethylene glycol dimethacrylate can be mixed with structural elements of the bifunctional tag in the presence of a photoinitiator and ultraviolet irradiation used to cross-link the monomers. The resulting polymer can be crushed or ground into smaller pieces and washed to remove the structural elements of the bifunctional tag, leaving a particulate matrix material capable of binding one or more structural elements of the bifunctional tag. Examples of other functional monomers, cross-linkers and initiators can be used to generate an artificial binding substrate are provided. See, e.g., U.S. Pat. No. 7,319,038; Alexander, et al., *J. Mol. Recognit.* 19:106-180, 2006, each of which is incorporated herein by reference. In a further aspect, hydrogels can be used for molecular imprinting. See, e.g., Byrne et al., "Molecular imprinting within hydrogels", *Advanced Drug Delivery Reviews,* 54: 149-161, 2002, which is incorporated herein by reference. Other examples of synthetic binders are provided. See, e.g., U.S. Pat. Nos. 6,255,461; 5,804,563; 6,797,522; 6,670,427; and 5,831,012; and U.S. Patent Application 20040018508; and Ye and Haupt, *Anal Bioanal Chem.* 378: 1887-1897, 2004; Peppas and Huang, *Pharm Res.* 19: 578-587 2002, each of which is incorporated herein by reference.

In an aspect, the one or more binding agents can be configured to preferentially bind a bifunctional tag that is bound to or occupied by an appropriate target component. The binding agents are further configured such that unbound or unoccupied bifunctional tags and/or target components are unable to bind to the binding agents and remain in the blood or lymph circulation. Binding agents configured to bind only the bifunctional tag/target component complex can be generated by developing screening assays for binding agents that preferentially bind the complex. For example, an antibody screen can be developed using a phage display library and a bifunctional tag/target component complex as the screening antigen. Once antibodies are found that bind the bifunctional tag/target component complex, additional negative screens are performed to eliminate those antibodies that bind either the bifunctional tag alone or the target component alone. See, e.g., Nemazee & Sato, *Proc. Natl. Acad. Sci, USA.* 79:3828-3832, 1982; Malek et al., *Proc. Natl. Acad. Sci., USA.* 80:5694-5698, 1983; U.S. Pat. No. 5,985,579, which are incorporated herein by reference. A similar differential screening modality can be used to generate binding agents that are aptamers, novel peptides, or artificial binding substrates.

The interaction of the bifunctional tag/target component complex with a binding agent can be monitored with a binding sensor using one or more of the sensor methodologies disclosed herein. In this instance, the binding agent configured to bind a bifunctional tag/target component complex is attached to a component of the sensor. Upon binding of the bifunctional tag/target component complex, the sensor is activated and sends a signal to the controller indicating capture and sequestration of the target component. In response, the controller can optionally initiate release of one or more additional reactive components to inactivate and/or disrupt the sequestered target component.

Reactive Components for Inactivation of Target Components

The device disclosed herein further includes one or more second reservoirs configured to release one or more reactive components for modulating a physiological effect of one or more sequestered target components. A reactive component includes, but is not limited to, a denaturing agent, a degradative agent, a cell-disrupting agent, a modulator, an energy source, an apoptotic agent, a programmed cell death-inducing agent, a cytotoxic agent, cytostatic agent, a chemotherapeutic agent, an antibody toxin or a combination thereof. Reactive components for modulating a physiological effect of one or more sequestered target components can be any of a number of chemical types including but not limited to a protein, a peptide, a small molecule, a chemical, a toxin, an aptamer, or an inhibitory RNA, DNA, or other nucleic acid. The one or more reactive components are incorporated into or released within one or more second reservoirs associated with the device. Alternatively, the one or more reactive components are diffusible components released from a reservoir of the device into the blood of the subject.

In an aspect, the reactive component can be a recombinant protein or peptide. The recombinant protein or peptide can be generated exogenously and incorporated into one or more second reservoirs of the device. In an aspect, the recombinant protein or peptide can be generated by one or more cells incorporated into the device. The one or more cells can be genetically modified to synthesize and secrete the one or more reactive components. Cells that can be used for this purpose include, but are not limited to, mammalian cells, enucleated cells (e.g., erythrocytes), plants cells, bacteria, or yeast. DNA sequences corresponding to one or more reactive components are cloned into an appropriate cell type using standard procedures with appropriate expression vectors and transfection protocols. The genetically modified cells are encapsulated in one or more compartments of the device and secrete the one or more reactive components into the blood fluid or lymph fluid of a vertebrate subject. The genetically modified cells are kept separate from the circulation of a vertebrate subject using a size-limiting biocompatible mesh or membrane filter, for example, that allows passage of the cytotoxic, cytostatic, and/or apoptotic, but not the larger cells.

In an aspect, the one or more reactive components are released from synthetic vesicles or particles. Examples include any of a number of drug delivery vehicles including, but not limited to, phospholipid vesicles (liposomes), nanoparticles, polymers, or hydrogels. The release of the one or more reactive components can be triggered by binding of a specific target to the synthetic vesicle or particle. For example, one or more DNA aptamers can be incorporated into hydrogel and designed to bind one or more specific targets and release the contents of the hydrogel in response to the controller which releases the hydrogel into the blood fluid or lymph fluid of the subject.

Reactive components can include denaturing agents that modulate a physiological effect of the one or more target components. The device including one or more reactive components can include one or more denaturing agents. The physiological effect of one or more target components can be modulated by the process of denaturation in which the secondary, tertiary or quaternary structure of one or more target components are altered by denaturing agents. Examples of denaturing agents include, but are not limited to, acids such as acetic acid, trichloroacetic acid (TCA), sulfosalicyclic acid, picric acid; solvents such as methanol, ethanol, and acetone; cross-linking agents such as formaldehyde and gluteraldehyde; chaotropic agents such as urea, guanidinium chloride, and lithium perchlorate; and disulfide bond reducers such as 2-mercaptoethanol, dithithreitol, and TCEP. In an aspect, acids can be used to denature a protein molecule by exposing the protein molecule to a pH below its isoelectric point. Under these conditions, the protein molecule will lose its negative charge and retain only positive charges. The like positive charges can repel one another and in areas of large charge density, the intramolecular repulsion can be sufficient enough to cause unfolding of the protein. The one or more denaturing agents can be incorporated into or released within one or more second reservoirs of the device. Alternatively, the one or more denaturing agents can be released by the device as diffusible agents into the blood.

Reactive components can include degradative agents that modulate a physiological effect of the one or more target components. The physiological effect of one or more target components can be modulated by the one or more degradative agents that act by breaking peptide bonds within the primary amino acid sequence of the one or more inflammatory mediators. The one or more degradative agents can include any of a number of agents designed to cleave one or more peptide bonds of the primary amino acid sequence of one or more target components. Examples of degradative agents, include but are not limited to proteases, strong acids, strong bases, free radicals, natural or synthetic proteasomes, or photoactivatable agents. The one or more degradative agents can be incorporated into or released within one or more second reservoirs of the device. Alternatively, the one or more degradative agents can be released by the device as diffusible agents into the blood.

The device including one or more degradative agents can include one or more proteases. Examples of proteases include, but are not limited to, serine proteases, e.g., as trypsin, chymotrypsin, elastase, dipeptidyl peptidase IV, and subtilisin; cysteine proteases, e.g., papain, cathepsins, caspases, calpains; aspartic acid proteases, e.g., pepsin, renin, and HIV-proteases; metalloproteases, e.g. carboxypeptidases, aminopeptidases, and matrix metalloproteases, e.g. MMP1 through MMP28. The one or more proteases can be free in solution. Alternatively, the one or more proteases can be bound to a substrate. In an aspect, trypsin can be bound to glass beads. See, e.g., Lee, et al., *J. Dairy Sci.*, 58:473-476, 1974, which is incorporated herein by reference. Alternatively, trypsin and other proteases can be bound to an agarose matrix. Sources of immobilized proteases including trypsin and pepsin are available from commercial sources (Pierce Chemicals, Rockford, Ill.; Applied Biosystems, Foster City, Calif.).

The device including one or more degradative agents can include a natural or synthetic complex of proteases. In an aspect, the one or more target components can be subject to degradation using proteasomes. A proteasome is a naturally occurring large protein complex that contains multiple subunits. The complex includes several protease activities, for example, chymotrypsin-like activity, trypsin-like activity, glutamic acid protease activity, and threonine protease activity. Proteasome complexes can be purified from fractionated cells using ultracentrifugation through a 10-40% glycerol gradient. See, e.g., Pervan, et al., *Mol. Cancer. Res.* 3:381-390, 2005, which is incorporated herein by reference. Proteasomes can be isolated using a commercially available isolation kit. (Proteasome Isolation Kit, Human 539176-1KIT, Calbiochem (EMD Chemicals, Inc.; Gibbstown, N.J.).

The device including one or more degradative agents can include an agent that selectively targets one or more target component for degradation. In an aspect, the one or more target components can be covalently tagged with ubiquitin for selective destruction by proteasomes. Ubiquitin is a small and highly conserved protein. An isopeptide bond links the terminal carboxyl of ubiquitin to the $\epsilon$-amino group of a lysine residue of a protein targeted for degradation. The joining of ubiquitin to the targeted protein is ATP-dependent. Three enzymes are involved, designated E1, E2 and E3. Initially, the terminal carboxyl group of ubiquitin is joined in an ATP-dependent thioester bond to a cysteine residue on ubiquitin-activating enzyme (E1). The ubiquitin is then transferred to a sulfhydryl group on a ubiquitin-conjugating enzyme (E2). A ubiquitin-protein ligase (E3) then promotes transfer of ubiquitin from E2 to the ε-amino group of a lysine residue of a protein recognized by that E3, forming an isopeptide bond. There are distinct ubiquitin ligases with differing substrate specificity. In addition, some proteins have specific sequences termed a "destruction box" that is a domain recognized by a corresponding ubiquitin ligase. In general, E1, E2, and E3 can be isolated from natural sources or generated using standard molecular biology techniques and used to ubiquinate proteins in vitro. See, e.g., Chen, et al., *EMBO Rep.* 2:933-938, 2001, which is incorporated herein by reference. In an aspect, the E2 ligase can be genetically engineered in such a manner as to recognize a specific substrate. See, e.g., Colas, et al., *PNAS* 97:13720-13725, 2000, which is incorporated herein by reference. The device including the treatment region can further include one or more genetically engineered E2 ligase enzymes capable of adding ubiquitin to and facilitating degradation of the one or more target components in the blood of the subject.

In a further aspect, the ubiquitin can be indirectly associated with the one or more target components. In an aspect, the ubiquitin can be linked to an antibody or aptamer structural component of the bifunctional tag. Binding of the ubiquitin-labeled antibody or aptamer to one or more target components can mark the protein conjugate for degradation by proteasomes.

The device including one or more degradative agents can include a strong acid. Acid hydrolysis can result in degradation of the one or more target components. In this aspect, strong acids such as hydrochloric acid or sulfuric acid can be used to break the carbon-nitrogen peptide bond. Degradation of one or more target components by acid hydrolysis can be optionally performed in combination with elevated temperature, a nitrogen atmosphere and/or microwave energy.

The device including one or more degradative agents can include one or more reactive oxygen species. Examples of reactive oxygen species include, but are not limited to, singlet molecular oxygen, superoxide ion, hydrogen peroxide, hypochlorite ion, hydroxyl radical. Reactive oxygen species can react directly with proteins, targeting peptide bonds or amino acid side chains, for example, reacting with the one or more target components bound by an affinity binding component to a surface of the treatment region. See, e.g., Davies, *Biochem. Biophys. Res. Commun.* 305:761-770, 2003, which is incorporated herein by reference. A number of the reactions mediated by reactive oxygen species lead to introduction of carbonyl groups into the protein which in turn can result in inactivation of the protein by cleavage of the peptide bound to yield lower-molecular weight products, cross-linking of proteins to yield higher-molecular weight products, or loss of catalytic function or structural function by distorting secondary and tertiary structure, or combination thereof. Reactive oxygen species can induce a amidation, diamide, glutamate oxidation and/or proline oxidation which can lead to cleavage of peptide bonds. Reactive oxygen species can be formed by the interaction of biological molecules with components including, but not limited to, ionizing radiation, as a byproduct of cellular respiration, and dedicated enzymes such as NADPH oxidase and myeloperoxidase.

In an aspect, the device including one or more degradative agents can include reactive oxygen species that are singlet oxygen species. Singlet oxygen can cause damage to both the side-chains and backbone of amino acids, peptides, and proteins. See, e.g., Davies, *Biochem. Biophys. Res. Commun.* 305:761-770, 2003, which is incorporated herein by reference. Singlet oxygen species can react with tryptophan, tyrosine, histidine, methionine and/or cysteine and cystine residues within a polypeptide and can cause increased susceptibility to proteolytic enzymes, an increased extent/susceptibility to unfolding, changes in conformation, an increase in hydrophobicity, and changes in binding of co-factor and metal ions. In particular, the interaction of tyrosine with singlet oxygen species can lead to fragmentation or cleavage of the polypeptide. See, e.g., Davies, *Biochem. Biophys. Res. Commun.* 305:761-770, 2003, which is incorporated herein by reference.

The device including one or more degradative agents can include one or more singlet oxygen species generated by a photosensitizer, a chemical which upon exposure to a given wavelength of light emits singlet oxygen species. Examples of photosensitizers include, but are not limited to, porphyrin derivatives such as porfimer sodium, which is excited by red light at 630 nm; chlorins and bacteriochlorins such as bonellin (maximum absorbance 625 nm), mono-L-aspartyl chlorine e6 (max abs 654), m-tetrahydroxyphenyl chlorine (mTHPC, max abs 652 nm), and tin etiopurpurin (SnET2, maximum absorbance 660 nm); benzoporphyrin derivatives such as veteroporfin (also labeled BPD-MA, maximum absorbance 690 nm), 5-aminolaevulinic acid (ALA, porphoryin precursor to PpIX (maximum absorbance 635 nm)); texaphyrins such as lutetium texaphyrin (Lu-Tex, maximum absorbance 732), Phthalocyanines and naphthalocyanines (maximum absorbance 670-780 nm); and cationic photosensitizers such as rhodamine 123 and methylene blue. See, e.g., Prasad (2003) *Introduction to Biophotonics*, John Wiley & Sons, Inc. Hoboken, N.J. Tunable quantum dots (QDs), especially those absorbing in the wavelength range of 600 to 800 nm, also emit singlet oxygen species in response to light provided by the device. The tunable quantum dots can be useful as photosensitizers. See, e.g., Samia, et al., *Photochem. Photobiol.* 82:617-625, 2006, which is incorporated herein by reference.

Reactive components can include cell-disrupting agents that modulate a physiological effect of the one or more target components. The device including one or more reactive components can include one or more cell-disrupting agents. Examples of cell-disrupting agents include, but are not limited to, alcohols and other organic solvents such as methanol, ethanol, isopropanol, and acetone; cross-linking aldehydes such as formaldehyde and gluteraldehyde; oxidizing agents such as sodium hypochlorite, calcium hypochlorite, chloramine, chlorine dioxide, hydrogen peroxide, iodine, ozone, acidic electrolyzed water, peracetic acid, performic acid, potassium permanganate, potassium peroxymonosulfate; acids such as acetic acid, trichloroacetic acid (TCA), sulfosalicyclic acid, picric acid; phenolics such as phenol, O-phenylphenol, chloroxylenol, hexachlorophene, thymol; chaotropic agents such as urea, guanidinium chloride, and lithium perchlorate; and disulfide bond reducers such as 2-mercaptoethanol, dithiothreitol; and quaternary ammonium compounds. For example, organic solvents such as methanol, ethanol or acetone can disrupt a cell by solubilizing the lipids in the plasma membrane and allowing the soluble contents of the cell to be released. In an aspect, the one or more cell-disrupting agents are incorporated into or released within one or more second reservoirs of the device. In an aspect, the one or more cell-disrupting agents are released by the device as diffusible agents into the blood.

The physiological effect of one or more target components can be modulated by the one or more cell-disrupting agents that act by breaking peptide bonds within the primary amino acid sequence of proteins and peptides associated with one or more target components. In an aspect, the device including one or more cell-disrupting agents can include one or more proteases. Examples of proteases include, but are not limited to, serine proteases, e.g., as trypsin, chymotrypsin, elastase, dipeptidyl peptidase IV, and subtilisin; cysteine proteases, e.g., papain, cathepsins, caspases, calpains; aspartic acid proteases, e.g., pepsin, renin, and HIV-proteases; metalloproteases, e.g. carboxypeptidases, aminopeptidases, and matrix metalloproteases, e.g. MMP1 through MMP28. In one aspect, the one or more proteases are free in solution. In an aspect, the one or more proteases are bound to a substrate.

The device including one or more cell-disrupting agents can include one or more free radical reactive oxygen species. Examples of reactive oxygen species include, but are not limited to, singlet molecular oxygen, superoxide ion, hydrogen peroxide, hypochlorite ion, hydroxyl radical. Reactive oxygen species can react directly with proteins associated with the one or more target components, targeting peptide bonds or amino acid side chains. In an aspect, the device including one or more cell-disrupting agents can include reactive oxygen species that are singlet oxygen species. Singlet oxygen can cause damage to both the side-chains and backbone of amino acids, peptides, and proteins. See, e.g., Davies, *Biochem. Biophys. Res. Commun.* 305: 761-770, 2003, which is incorporated herein by reference. The cell-disrupting agents can further include one or more singlet oxygen species generated by a photosensitizer. Examples of photosensitizers various classes of photosensitizers have been disclosed herein. A number of cell types including cancer cells and bacterial pathogens are at least partially inactivated in response to treatment with photosensitizers such as phthalocyanines, phenothiazines, and porphyrins. See, e.g., Miller, et al., *Toxicol. Appl. Pharmacol.* 224:290-299, 2007; Jori, et al., *Lasers Surg. Med.* 38:468-481, 2006; Keefe, et al., *Lasers Surg. Med.* 31:289-293, 2002, each of which is incorporated herein by reference.

Modulators can modulate a physiological effect of the one or more target components. The device can include one or more reactive components that are one or more modulators that either directly or indirectly modulate the activity of one or more target components in the blood of a vertebrate subject. The one or more modulators can be incorporated into or released within one or more second reservoirs of the device. Alternatively, the one or more modulators can be released by the device as diffusible agents into the blood. A modulator can alter, modify, reduce or eliminate the activity of one or more target components by preventing the binding of one or more target components to their respective cognates. Alternatively, a modulator can alter, modify, reduce or eliminate the activity of one or more target components by inhibiting the enzymatic activity, e.g., phosphorylation activity, of the one or more target components. Alternatively, the one or more modulators can indirectly alter, modify or eliminate the activity of one or more target components by attenuating the gene expression of one or more target components. In an aspect, the one or more modulators can indirectly alter or eliminate the activity of one or more target components by increasing the expression of endogenous antagonists of the one or more target components.

In general, the one or more modulator can be a protein, a peptide, a small molecule, an aptamer, or an inhibitory RNA, DNA, or nucleic acid. Modulators are contemplated that either directly or indirectly antagonize the activity of one or more target components and/or attenuate expression of one or more target components.

In an aspect, the one or more modulator is designed to block the activity or binding properties of one or more target components that is an inflammatory mediator. Examples of modulators of inflammatory mediator activity and binding include but are not limited to antibodies, e.g., infliximab, adalimumab, basiliximab efalizumab; soluble receptors, e.g., etanercept, abatacept, alefacept; corticosteroids, e.g., hydrocortisone, cortisone, prednisone, prednisolone, methylprednisolone, meprednisone, triamcinolone, paramethsone, fluprednisolone, betametasone, and dexamethasone; nonsteroidal anti-inflammatory drugs (NSAIDS), e.g., selective cycloxygenase (COX) inhibitors exemplified by celecoxib, etoricoxib, meloxicam, and valdecoxib and non-selective COX inhibitors exemplified by diclofenac, difluisal, etodolac, fenoprofen, fluripofen, ibuprofen, indomethacin, ketoprofen, ketorolac, nabumetone, naproxen, oxaprozin, piroxicam, sulindac, tenoxica, tiaprofen, tolmetin, azapropazone, and carprofen; and, e.g., methotrexate, azathioprine, pennicillamine, hydroxychloroquine, chloroquine, cyclophosphamide, cyclosporine, mycophenolate mofetil, gold, and sulfasalazine.

Reactive components can include cytotoxic, cytostatic, apoptotic, and/or chemotherapeutic agents that modulate a physiological effect of the one or more cellular target components. The device including one or more reactive component can include one or more of a cytotoxic, a cytostatic, an apoptotic, and/or a chemotherapeutic agent. Reactive components that are cytotoxic, cytostatic, apoptotic, and/or chemotherapeutic agents are contemplated that either directly or indirectly inactivate or kill one or more target components or target cells. Examples of cytotoxic, cytostatic, apoptotic, and/or chemotherapeutic agents include but are not limited to vinca alkaloids (e.g., vinblastine, vincristine, vinflunine, vindesine, vinorelbine); taxanes (e.g., docetaxel, larotaxel, ortataxel, paclitaxel, tesetaxel); epothilones (e.g., ixabepilone); dihydrofolate reductase inhiitors (e.g., aminopterin, methotrexate, pemetrexed); thymidylate synthase inhibitors (e.g., raltitrexed); adenosine deaminase inhibitor (e.g., pentostatin); halogenated/ribonucleotide reductase inhibitors (e.g., cladribine, clofarabine, fludarabine); thiopurine (e.g., thioguanine, mercaptopurine); thymidylate synthase inhibitors (e.g., fluorouracil, capecitabine, tegafur, carmofur, floxuridine); DNA polymerase inhibitors (e.g., cytarabine); ribonucleotide reductase inhibitor (e.g., gemcitabine, hydroxyurea); hypomethylating agent (e.g., azacitidine, decitabine); camptotheca (e.g., camptothecin, topotecan, irinotecan, rubitecan, belotecan); podophyllum (e.g., etoposie, teniposide); anthracyclines (e.g., aclarubicin, daunorubicin, doxorubicin, epirubicin, idarubicin, amrubicin, pirarubicin, valrubicin, zorubicin); anthracenediones (e.g., mitoxantrone, pixantrone); nitrogen mustards (e.g., mechlorethamine, cyclophosphamide, chlorambucil, bendamustine, uramustine, estramustine); nitrosureas (e.g., carmustine, lomustine, fotemustine, nimustine, ranimustine, streptozocin); aziridines (e.g., carboquone, thioTEPA, triziquone, triethylenemelamine); platinum (e.g., carboplatin, cisplatin, nedaplatin, oxaliplatin, triplatin, tetranitrate, satraplatin); hydrazines (e.g., procarbazine); triazenes (e.g., dacarbazine, temozolomide, altretamine, mitobronitol); *streptomyces* (actinomycin, bleomycin, mitomycin, plicamycin); aminolevulinic acid/methyl aminolevulinate; efaproxiral; porphyrin derivatives (porfimer sodium, talaporfin, temoporfin, verteporfin); farnesyltransferase inhibitors, cyclin-dependent kinase inhibitors, proteasome inhibitors, phosphodiesterase inhibitors, IMP dehydrogenase inhibitors, lipooxygenase inhibitors, PARP inhibitors, endothelin receptor antagonists (e.g., atrasentan); retinoid X receptor (e.g., bexarotine); sex steroid (e.g., testolactone); amsacrine, trabectedin, alitretinoin, tretinoin, arsenic trioxide, celecoxib, demecolcine, elesclomol, elsamitrucin, etoglucid, lonidamine, lucanthone, mitoguazone, mitotane, oblimersen, temsirolimus, vorinostat. The cytotoxic agent can further be a biological agent, e.g., a peptide, a protein, an enzyme, a receptor and/or an antibody. Examples of biological agents currently used to treat cancer include, but are not limited to, cytokines such as interferon-α, interferon-γ, and interleukin-2, an enzyme such as asparaginase, and monoclonal antibodies such as alemtuzumab, bevacizumab, cetuximab, gemtuzumab, rituximab, and trastuzumab.

The device including one or more reactive components that are cytotoxic, cytostatic, apoptotic, and/or chemotherapeutic agents can include one or more of an antibacterial drug. Examples of antibacterial drugs include, but are not limited to, beta-lactam compounds (e.g., penicillin, methicillin, nafcillin, oxacillin, cloxacillin, dicloxacilin, ampicillin, ticarcillin, amoxicillin, carbenicillin, and piperacillin); cephalosporins and cephamycins (e.g., cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxine, ceftriaxone, cefixime, cefpodoxime, proxetil, cefdinir, cefditoren, pivoxil, ceftibuten, moxalactam, and cefepime); other beta-lactam drugs (e.g., aztreonam, clavulanic acid, sulbactam, tazobactam, ertapenem, imipenem, and meropenem); other cell wall membrane active agents (e.g., vancomycin, teicoplanin, daptomycin, fosfomycin, bacitracin, and cycloserine); tetracyclines (e.g., tetracycline, chlortetracycline, oxytetracycline, demeclocycline, methacycline, doxycycline, minocycline, and tigecycline); macrolides (e.g., erythromycin, clarithromycin, azithromycin, and telithromycin); aminoglycosides (e.g., streptomycin, neomycin, kanamycin, amikacin, gentamicin, tobramycin, sisomicin, and netilmicin); sulfonamides (e.g., sulfacytine, sulfisoxazole, silfamethizole, sulfadiazine, sulfamethoxazole, sulfapyridine, and sulfadoxine); fluoroquinolones (e.g., ciprofloxacin, gatifloxacin, gemifloxacin, levofloxacin, lomefloxacin, moxifloxacin, norfloxacin, and ofloxacin); antimycobacteria drugs (e.g., isoniazid, rifampin, rifabutin, rifapentine, pyrazinamide, ethambutol, ethionamide, capreomycin, clofazimine, and dapsone); and miscellaneous antimicrobials (e.g., colistimethate sodium, methenamine hippurate, methenamine mandelate, metronidazole, mupirocin, nitrofurantoin, polymyxin B, clindamycin, choramphenicol, quinupristin-dalfopristin, linezolid, spectrinomycin, trimethoprim, pyrimethamine, and trimethoprim-sulfamethoxazole).

The device including one or more reactive components that are cytotoxic, cytostatic, apoptotic, and/or chemotherapeutic agents can include one or more of an antifungal agent. Examples of antifungal agents include, but are not limited to, anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

The device including one or more reactive components that are cytotoxic, cytostatic, apoptotic, and/or chemotherapeutic agents can include one or more of an anti-parasite agent. Examples of anti-parasite agents include, but are not limited to, antimalaria drugs (e.g., chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins); treatments for amebiasis (e.g., metronidazole, iodoquinol, paromomycin, diloxanide furoate, pentamidine, sodium stibogluconate, emetine, and dehydroemetine); and other anti-parasite agents (e.g., pentamidine, nitazoxanide, suramin, melarsoprol, eflornithine, nifurtimox, clindamycin, albendazole, and tinidazole).

The device including one or more reactive components that are cytotoxic, cytostatic, apoptotic, and/or chemotherapeutic agents can include one or more of an antiviral agent. Examples of antiviral agents include, but are not limited to, nucleoside analogs used to treat herpes simplex virus (HSV) and varicella-zoster virus (VZV) (e.g., valacyclovir, famciclovir, penciclovir, and trifluridine); nucleoside analogs used to treat cytomegalovirus (CMV) (e.g., ganciclovir, valganciclovir, and cidofovir); nucleoside and nonnucleoside reverse transcriptase inhibitors used to treat HIV (e.g., abacavir, didanosine, emtricitabine, lamivudine, stavudine, tenofovir, zalcitabine, zidovudine, delavirdine, efavirenz, and nevirapine); protease inhibitors used to treat HIV (e.g., atazanavir, darunavir, fosamprenavir, indinavir, lopinavir, nelfinavir, ritonavir, saquinavir, and tipranavir); and drugs used to treat hepatitis (e.g., interferon alfa, adefovir dipivoxil, entecavir, and ribavirin).

The device can include one or more reservoirs that store one or more reactive components. The one or more reservoirs of the device are configured to controllably release one or more reactive components. Each reservoir can contain one or more reactive components. Release of the reactive component from a reservoir is controlled by the controller component of the device. In an aspect, the reactive components can be housed in multiple reservoirs associated with the device. For example, the device can include one or more microchips each with multiple reservoirs sealed with removable caps to enable controlled release of one or more a denaturing agent, a degradative agent, a cell-disrupting agent, a modulator, an energy source, an apoptotic agent, a programmed cell death-inducing agent, a cytotoxic agent, cytostatic agent, a chemotherapeutic agent, an antibody toxin or a combination thereof. See, e.g., U.S. Pat. No. 7,413,846; Maloney & Santini, Proceedings 26$^{th}$ Annual International Conference IEEE EMBS, San Francisco, Calif., USA, Sep. 1-5, 2004, each of which is incorporated herein by reference.

Energy sources can modulate a physiological effect of the one or more target components. The device can include one or more reactive components that include one or more energy sources configured to modulate a physiological effect of the of one or more target components. The one or more energy sources can be directed to blood within the second reservoir or can be directed outside the device to the blood. The one or more energy sources provide energy types including, but not limited to, electromagnetic radiation, e.g., ultraviolet, infrared, optical, microwave, or millimeter wave; acoustic energy, e.g., ultrasonic acoustic energy; heat; atmospheric pressure glow discharge; electron beam radiation; or gamma radiation. In an aspect, the energy source itself can modulate a physiological effect of one or more target components. Alternatively, heat generated by the energy source can modulate a physiological effect of the one or more target components.

The application of one or more energy sources to the blood in the form of electromagnetic, acoustic, and/or electronic energy can induce denaturation and/or degradation of one or more target components. An energy source can denature target component by unfolding the structure and/or inducing changes in amino acid chains and/or other side chains. The energy source can degrade a target component by cleaving one or more chemical bonds such as peptide bonds. The energy source can otherwise modulate a physiological effect of the one or more target components by inducing aggregation of the one or more target components. The energy source can induce cellular disruption of a cellular target component leading to inactivation, apoptosis or death of the target cell.

The device including the one or more energy sources can provide a set of differing energy inputs specifically directed to modulating a physiological effect of one or more target components. The set of differing energy inputs selectively resonates a plurality of resonant structures in the one or more target components and can modulate a physiological effect of the one or more target components. See, e.g., U.S. Patent Application 2007/0021927 A1, which is incorporated herein by reference. The differing energy inputs are selected to resonate one or more resonant structures among the group of proximate atoms comprising the one or more target components. Application of a series of differing energy inputs can have a physical effect, such as transferring substantially more energy to a group of proximate atoms relative to other atoms in the surrounding medium, breaking a predetermined bond between two members of the group of proximate atoms, or changing a kinetic parameter of a reaction involving a member of the group of proximate atoms. The one or more resonant structures can be resonated simultaneously, sequentially, and/or in a temporally overlapping fashion. The series of differing energy inputs can be applied simultaneously, sequentially, and/or in a temporally overlapping fashion.

The set of differing energy inputs can be electromagnetic beams, each of which can have one or more characteristics including, but not limited to, a selected set of frequencies, a selected set of phases, a selected set of amplitudes, a selected temporal profile, a selected set of polarizations, or a selected direction. The temporal profile of the set of differing energy inputs can be characterized by a selected beam duration, and/or by a selected change in frequency, modulation frequency, phase, amplitude, polarization, or direction during a selected time interval. At least one electromagnetic beam can be polarized, amplitude modulated, or frequency modulated, and it can be, for example, an infrared beam. A plurality of electromagnetic beams can differ in frequency, modulation frequency, phase, amplitude, polarization, or direction, and/or can intersect at a target location. The method can include scanning at least one electromagnetic beam.

In an aspect, the device can include reactive components that include an energy field including, but not limited to, an electric field, a magnetic field, an electromagnetic field, a mechanical stress, a mechanical strain, a lowered or elevated temperature, a lowered or elevated pressure, a phase change, an adsorbing surface, a catalyst, an energy input, or a combination of any of these. The energy field can result in inactivation of the one or more target components. Mechanical stress, mechanical strain, lowered or elevated pressure, phase change, or adsorbing surface can provide energy to result in cellular disruption of target cells.

The device including the one or more energy sources can generate heat that induces inactivation of one or more target components. Exposure of most proteins or peptides to high temperature results in irreversible denaturation due to the weakening of long range bonds associated with tertiary structure and cooperative hydrogen bonds associated with helical structure. As these noncovalent bonds are broken, the protein molecule becomes more flexible and exposed to the solvent. Water molecules associated with the solvent form new hydrogen bonds that cannot be energetically overcome even as the protein molecule is cooled, leaving the protein molecule in an altered or denatured state. In an aspect, the one or more target components can be inactivated by treatment with a heat source. The heat source can be electrical, heating the entirety of the one or more second reservoirs of the device. Alternatively, the heat source can heat a substrate of the device to which one or more target components are attached. Alternatively, the heat source can be more focused such as that experienced from exposure to focused electromagnetic energy, e.g. from a laser. In an aspect, the one or more target components can bind to specific binding agents associated with one or more carbon nanotubes, the latter of which can emit heat in response to near infrared (NIR) radiation. See, e.g., Kam, et al., *PNAS* 102:11600-11605, 2005, which is incorporated herein by reference.

The device including the one or more energy sources can generate microwave energy for use in modulating a physiological effect of one or more target components. An energy source that incorporates microwave energy can result in degradation of the one or more target components. Microwaves are electromagnetic radiation with wavelengths between 0.01 and 1 meter and a frequency range between 0.3 and 30 GHz. The efficiency of microwave denaturation and/or degradation can be enhanced by including an acid, a protease, a chemical or combination thereof. The effects of microwave energy on peptide bond integrity can provide more that just rapid heating and suggests that some non-heat component of microwaves facilitates breakdown of the peptide bond. See, e.g., Lill, et al., *Mass. Spectrometry Rev.* 26:657-671, 2007, which is incorporated herein by reference.

The device including the one or more energy sources can generate focused ultrasound energy for use in modulating a physiological effect of one or more target components. Sonication in the form of focused ultrasound energy can result in degradation of the one or more target components. In an aspect, high intensity focused ultrasound produces cavitation bubbles that when collapsed yield very high localized pressures and high temperatures along with shear forces, jets and shock waves. The local increase in temperature and pressure can effectively denature proteins. See, e.g., Lopez-Ferrer, et al., *J. Proteome Res.* 7:3860-3867, 2008, which is incorporated herein by reference.

The device including the one or more energy sources can generate plasma by atmospheric dielectric-barrier discharge for use in modulating a physiological effect of one or more target components. Plasma generated by atmospheric dielectric-barrier discharge can result in degradation of the one or target components. See, e.g., Hou, et al., *IEEE Transactions on Plasma Science* 36:1633-1637, 2008, which is incorporated herein by reference. Plasma is an ionized gas in which a certain proportion of the electrons are free rather than bound to an atom or molecule. The plasma can be generated by a non-thermal discharge at atmospheric pressure by application of high voltages across small gaps. The atmospheric dielectric-barrier discharge can be scalable from one millimeter to one meter (Walsh, et al., IEEE Transactions on Plasma Science 36:1314-1315, 2008, which is incorporated herein by reference. A plasma jet and/or a plasma brush can be used to degrade one or more target components.

The device including the one or more energy sources can generate high energy radiation for use in modulating a physiological effect of one or more target components. High energy radiation can result in degradation of the one or more target components. Gamma radiation in the range of about 2.0 kGy to about 23.0 kGy is able to denature protein in a dose dependent manner as determined by size chromatography. See, e.g., Vuckovic, et al., *J. Serb. Chem. Soc.* 70:1255-1262, 2005, which is incorporated herein by reference. Sources of gamma radiation that can be included in the device include but are not limited to cobalt-60, cesium-137, and technetium-99.

The device including the one or more energy sources can generate electron beam radiation for use in modulating a physiological effect of one or more target components. Electron beam radiation can result in degradation of the one or more target components. Electron beam energy of 92.9 kGy induces physical changes and loss of protein antigenicity (Katial, et al., *J. Allergy Clin. Immunol.* 110:215-219, 2002, which is incorporated herein by reference. A nanoscale electron beam generator can be devised from a network array structure of carbon nanotubes. See, e.g., U.S. Pat. No. 7,355, 334, which is incorporated herein by reference.

The device including one or more energy source can emit electrical energy in a focused area within the treatment region to inactivate one or more cellular target components. For example, cancer cells in suspension can be at least partially ablated using electrical pulses sufficient to induce irreversible electroporation of the cells. See, e.g., Miller et al. *Technol. Cancer Res. Treat.* 4:699-705, 2005, which is incorporated herein by reference. In an aspect, at least partial inactivation of one or more cellular target components can be achieved by exposure to 10-30, 0.3 millisecond pulses at 500 to 2500 V/cm.

The device including one or more energy source can emit electromagnetic energy sufficient to modulate a physiological effect of one or more cellular target components. The electromagnetic energy can range over a the spectrum of frequencies from gamma ray, x-ray, ultraviolet, visible, near infrared, infrared, microwave, to radiowaves.

The device including one or more energy source can emit ultraviolet radiation to modulate a physiological effect of one or more cellular target components. A number of pathogens are inactivated or killed by ultraviolet germicidal irradiation. Ultraviolet light ranges from UVA (400-315 nm; long wave or 'blacklight'), UVB (315-280 nm, medium wave), and UVC (<280 nm, short wave or 'germicidal'). The bacterium *Escherichia coli* is partially or completely inactivated by exposure to a UV electromagnetic energy source at wavelengths of 100-280 nm. *Escherichia coli* as well as *Salmonella enteritidis* is also inactivated using pulsed broad-spectrum electromagnetic energy with high UV content from, for example, a Xenon lamp. In this instance, targeted bacteria are subjected to 100-1000 pulses of broad-spectrum light with each pulse lasting, for example, 85 ns and having, for example, a power output of 10 MW. See, e.g., Anderson et al. *IEEE Transactions on Plasma Science* 28:83-88, 2000; Hancock et al. *IEEE Transactions on Plasma Science* 32:2026-2031, 2004, each of which is incorporated herein by reference. Viruses and fungi (e.g., *Aspergillus flavus* and *Aspergillus fumigatus*) are also inactivated by ultraviolet irradiation. See, e.g., Tseng & Li, *J. Occup. Envirn. Hyg.* 4:400-405, 2007; Green et al. *Can. J. Microbiol.* 50:221-224, 2004, each of which is incorporated herein by reference.

The device including one or more energy source can emit visible light to modulate a physiological effect of one or more cellular target components. *Staphylococcus aureus* and *Pseudomonas aeruginosa* can be inactivated using a wavelength of 405 nm at doses ranging from 1-20 J/cm$^2$. See, e.g., Guffey et al. *Photomed. Laser Surg.* 24:680-683, 2006, which is incorporated herein by reference. *Pseudomonas aeruginosa* as well as *Escherichia coli* are partially inactivated using a wavelength of 630 nm at 1-20 J/cm$^2$. See, e.g., Nussbaum et al. *J. Clin. Laser Med. Surg.* 20:325-333, 2002, which is incorporated herein by reference. In an aspect, a pathogen such as *Escherichia coli* can be at least partially inactivated or killed using a 810 nm diode laser with doses ranging from 130-260 J/cm$^2$. See, e.g., Jawhara et al. *Lasers Med. Sci.* 21:153-159, 2006, which is incorporated herein by reference. In some aspect, visible or near infrared energy (e.g., 465 nm, 600 nm, and 950 nm) can be used to alter the structural function of iron dependent pathogens by altering the function of heme iron prophyrins. See, e.g., U.S. Pat. No. 6,030,653, which is incorporated herein by reference. In an aspect, viruses can be at least partially inactivated using a very low power laser emitting 80 femtosecond pulses at a wavelength of 425 nm and frequency of 80 MHz. See, e.g., Tsen et al. *Virol. J.* 4:50, 2007, which is incorporated herein by reference.

In an aspect, visible light energy can be combined with one or more reactive component that include a photosensitive agent to modulate a physiological effect of one or more target cells. See, e.g., Maisch *Lasers Med. Sci.* 22:83-91, 2007; Jori et al. *Lasers Surg. Med.* 38:468-481, 2006, each of which is incorporated herein by reference. The visible light energy combined with the one or more photosensitive agents can be focused to a site of bacterial infection in the vertebrate subject, or can be focused onto the target cell or target component within the target region in the vertebrate subject. For example, *Staphylococcus aureus* and *Pseudomonas aeruginosa* are inactivated using either a 0.95-mW helium-neon laser (632 nm) or a 5-mW indium-gallium-aluminum-phosphate laser (670 nm) with exposure doses ranging from 0.1 to 10.0 J/cm$^2$ in combination with the bacterial sensitizing agent, toluidine blue O. See e.g., DeSimone et al. *Phys. Ther.* 79:839-846, 1999, which is incorporated herein by reference. Similarly, bacterial inactivation by a laser diode or light-emitting diode at 630 nm to 665 nm is enhanced in combination with methylene blue. See e.g., Chan et al. *Lasers Surg. Med.* 18:51-55, 2003, which is incorporated herein by reference. A fluorescing dye, e.g., indocyanine green (ICG) can be used in combination with a diode laser emitting at 808 nm to inactive a pathogen or pathogens. See e.g., Bartels et al. *SPIE* 2395:602-606, 1995, which is incorporated herein by reference. In an aspect, a target cell, e.g., bacteria, can be inactivated using a polycationic photosensitizer in combination with irradiation with a laser diode or light-emitting diode at 630 nm to 665 nm at doses ranging up to a total fluence of 160 J/cm$^2$, e.g., in four 40 J/cm$^2$ aliquots, with imaging taking place after each aliquot of light. See e.g., Hamblin et al. *Photochem. Photobiol.* 75:51-57, 2002, which is incorporated herein by reference. In an aspect, a target cell, e.g., *Staphylococcus aureus*, can be at least partially inactivated using energy from an argon-ion pumped dye laser (wavelength of 630 nm with total light dose up to 180 J/cm$^2$, fluence rate 250 mW/cm$^2$, wherein the total light dose can be provided in one or more lower light energy aliquots) in combination with 5-aminolevulinic acid or porphyrin sodium. Effective photokilling of a target cell, e.g., *Staphylococcus aureus* or *Escherichia coli*, by endogenous porphyrins or exogenous porphyrins can be achieved by application of light at 400-450 nm at approximately 50 J/cm$^2$. With 600-700 nm light, a 10-fold higher light dose can provide a similar result for *S. aureus* killing. With dye laser light at 632.8 nm, 50 J/cm$^2$ can provide 3 orders of decrease in the viability of *S. aureus*. With white light, 75 J/cm$^2$ can provide 2-3 orders of decrease of *S. aureus* viability. See e.g., Karrer et al. *Lasers Med. Sci.* 14:54-61, 1999; Nitzan et al. *Lasers Med. Sci.* 14:269-277, 1999, each of which is incorporated herein by reference.

The device including the one or more energy sources can generate heat that alters the structural function of one or more cellular target components. In an aspect, the structural function of one or more cellular target components can be altered by laser-induced thermal energy. Lasers are commonly used to treat cancers including but not limited to basal cell carcinoma and the very early stages of cervical, penile, vaginal, vulvar, and non-small cell lung cancer. See e.g., National Cancer Institute *Laser in Cancer Treatment FactSheet*, 2004, which is incorporated herein by reference. In an aspect, the device can include one or more laser-type component capable of emitting electromagnetic energy sufficient to alter the structural function of circulating tumor cells or other target cells. Examples include but are not limited to a carbon dioxide ($CO_2$) laser (10,600 nm, 0.1-0.2 mm penetration depth), a Yttrium-Aluminium-Garnet (YAG) laser with Neodymium (Nd, 1064 nm or 1320 nm, 3-4 mm penetration depth), Erbium (Eb, 2940 nm, with <0.1 mm penetration depth), or Holmium (Ho, 2070 nm), diode laser (600-1600 nm), argon laser (488 nm and 514 nm, 1-1.5 mm penetration depth), or an excimer laser (180-350 nm, cell/tissue disintegration). As an example, melanoma and cervical cancer cells can be ablated with a $CO_2$ laser using a power output ranging from 40 W to 80 W. See, e.g., Gibson, et al. *Br. J. Surg.* 91:893-895, 2004; Bekassy et al. *Lasers. Surg. Med.* 20:461-466, 1997; Norberto et al. *Surg. Endosc.* 19:1045-1048, 2005; Hansen et al. *Minim. Invasive Ther. Allied Technol.* 15:4-8, 2006, each of which is incorporated herein by reference. Laser-induced thermal energy generated by a $CO_2$ or Nd:YAG laser can also be used to at least partially inactivate a pathogen. See, e.g. Bartels et al. *SPIE* 2395:602-606, 1995; Yeo et al. *Pure Appl. Opt.* 7:643-655, 1998; U.S. Pat. No. 6,030,653; Gronqvist et al. *Lasers Surg. Med.* 27:336-340, 2000, each of which is incorporated herein by reference.

The device including the one or more energy sources can emit electromagnetic energy in the form of x-rays to alter the structural function of one or more cellular target components. In an aspect, the device can contain a miniature X-ray emitter, such as that described in U.S. Patent Application 2004/0218724 A1, which is incorporated herein by reference. In an aspect, the device can contain radioisotopes, e.g., cobalt 60, cesium 137, or europium 152, that emit strong gamma rays and can be used to ablate cancerous cells. Optionally, the device can contain other intrinsically radioactive isotope such as those that might be used for brachytherapy, including, for example, iodine 125, iodine 131, strontium 89, phosphorous, palladium, or phosphate. In an aspect, the device can include an energy source that is an electron beam-driven x-ray source. For example, breast cancer cells can be ablated using a miniature electron beam-driven x-ray source at doses of 5 to 20 Gy. See, e.g., Ross et al. *Breast Cancer Res.* 7:110-112, 2005, which is incorporated herein by reference. A nanoscale electron beam generator can be devised from a network array structure of carbon nanotubes. See, e.g., U.S. Pat. No. 7,355,334, which is incorporated herein by reference.

The device including the one or more energy sources can generate electromagnetic energy in the form microwave or radiofrequency waves to alter the structural function of one or more cellular target components. The microwave range includes ultra-high frequency (UHF) (0.3-3 GHz), super high frequency (SHF) (3-30 GHz), and extremely high frequency (EHF) (30-300 GHz) signals. Microwave radiation at a frequency of 29.8 GHz (Ka-band), for example, can be used to selectively kill bacteria with minimal damage to healthy human cells See, e.g., Arndt et al. *Microwave radiation—Therapeutic application for cure of subcutaneous bacterial infections. Space Life Sciences*, NASA Research and Technology Development. Biennial Research and Technology Report, which is incorporated herein by reference.

The device including the one or more energy sources can use focused ultrasound to generate heat to alter the structural function of one or more cellular target components. Ultrasound causes tissue damage through conversion of mechanical energy into heat and through cavitation. High-intensity focused ultrasound (HIFU) uses short exposures of focused ultrasound that rapidly increases cellular temperature above 80 degrees centigrade and is used for ablation, for example, of hepatocellular carcinoma, prostate carcinoma, bladder and kidney cancers. See, e.g., Kennedy et al. *Br. J. Radiology* 76:590-599, 2003, which is incorporated herein by reference.

Optionally, the device can emit a laser-generated stress wave sufficient to disrupt a biological target. For example, stress waves sufficient to disrupt cell membranes can be generated with an ArF (193 nm) or a KrF (248 nm) eximer laser. Blood mononuclear cells and red blood cells are damaged using, for example, 5 pulses of pressure ranging from 700 to 1000 bar. See e.g., Lee et al. *IEEE Journal of Selected Topics in Quantum Electronics* 5:997-1003, 1999, which is incorporated herein by reference.

Two or more reactive components can be combined modulate a physiological effect of one or more target components. The device can include two or more reactive components that have been combined to inactivate or disrupt one or more target components. The two or more combined reactive components can be one or more binding agent combined with one or more a denaturing agent, a degradative agent, a cell-disrupting agent, a modulator, an energy source, an apoptotic agent, a programmed cell death-inducing agent, a cytotoxic agent, cytostatic agent, a chemotherapeutic agent, an antibody toxin or a combination thereof.

In an aspect, the two or more reactive components of the device can be incorporated into a single biomolecule. For example, the first reactive component can be a binding agent, e.g., an antibody, that includes a second reactive component that is a degradative activity. Certain antibodies are capable of cleaving the amide bond of peptide bonds. See, e.g., Janda, et al., *Science* 241:1188-1191, 1988; Lacroix-Desmazes, et al., *J. Immunol.* 177:1355-1365, 2006; Ponomarenko, et al., *PNAS,* 103:281-286, 2006; and U.S. Pat. No. 6,387,674, each of which is incorporated herein by reference. Alternatively, the first reactive component can be a binding agent, e.g., an antibody, and includes a second reactive component that is a reactive oxygen species. The one or more bifunctional tag/target component complex can bind to one or more binding agents that are catalytic antibodies capable of generating the reactive oxygen species $H_2O_2$ in response to UV radiation. See, e.g., Wentworth, et al., *Science* 293:1806-181811, 2001; Wentworth, *Science* 296:2247-2248, 2002; Wentworth, et al., *Proc. Natl. Acad. Sci. USA,* 97: 10930-10935, 2000, each of which is incorporated herein by reference. One or more antibodies or other binding agents can be generated for both binding and degradation of one or more bifunctional tag.

In an aspect, the first reactive component can be a binding agent, e.g., an antibody that includes a second reactive component that is a cellular toxin. For example, the first reactive component can be an antibody that binds a cellular target component and the second reactive component can be a photosensitizer which is activated upon exposure to electromagnetic energy. See, e.g., Serebrovskaya, et al., *Proc. Natl. Acad. Sci. USA.* 106: 9221-9225, 2009, which is incorporated herein by reference. In another example, the first reactive component can be an antibody directed against a cancer cell or other cellular target component and the second reactive component can be one or more of an auristatin, inhibitors of tubulin polymerization. See, e.g., Ma, et al., *Clin. Cancer Res.* 12: 2591-2596, 2006, which is incorporated herein by reference.

In an aspect, the two or more reactive components of the device can be incorporated into a single biomolecule and can include a first component that is a binding agent, e.g., an aptamer, and a second component that is a degradative agent, e.g., a protease. For example, one or more proteases can be conjugated or chemically linked to one or more oligonucleotide-based aptamers. The oligonucleotide-based aptamers are designed to bind bifunctional tags/target component complexes. Upon binding to the oligonucleotide-based aptamers, the one or more bifunctional tags/target component complexes are brought into proximity to the one or more proteases resulting in proteolytic degradation of the one or more bifunctional tags/target component complexes. Examples of proteases have been provided herein and can be linked to oligonucleotide-based aptamers using any of a number of methods for conjugating a polypeptide to an oligonucleotide. In a further aspect, a polypeptide protease can be conjugated to an oligonucleotide-based aptamer using a streptavidin-biotin bridge by introducing a biotinylated oligonucleotide into the aptamer sequence and linking it to a biotinylated protease through a streptavidin bridge. Alternatively, the polypeptide protease can be conjugated to the oligonucleotide-based aptamer using a thiol-maleimide linkage in which a carbon with an attached thiol group is placed on the aptamer and reacts with a maleimide group added to the C terminus of the protease. See, e.g., Nitin, et al., *Nucleic Acids Res.* 32:e58, 2004, which is incorporated herein by reference. A number of modified nucleotides are commercially available for use in synthesizing oligonucleotide aptamers with amines or other side chains for cross-linking (TriLink Biotechnologies, San Diego, Calif.; Sigma Aldrich, St. Louis, Mo.).

In a further aspect, the first reactive component can be a binding agent linked to a second reactive component encapsulated in a tunable vesicle. For example, the second reactive component, e.g., a denaturing and/or degradative agent, can be encapsulated in a tunable hydrogel. The binding of one or more bifunctional tags/target component complexes to the first reactive component, e.g., binding agent, releases the denaturing and/or degradative agent from the hydrogel. In an aspect, target-responsive hydrogels can be generated in which the contents of the hydrogel are selectively released in response to binding a specific target. The hydrogel can incorporate one or more binding agents that are antibodies. The hydrogel can release its contents in response to an antibody-antigen interaction. See, e.g., Miyata, et al., *PNAS* 103:1190-1193, 2006, which is incorporated herein by reference. In an aspect, the target-responsive hydrogel can incorporate one or more binding agents that are oligonucleotide-based aptamers and release its contents in response to an aptamer-ligand interaction. See Yang, et al., *J. Am. Chem. Soc.* 130:6320-6321, 2008, which is incorporated herein by reference. In the latter case, two or more distinct aptamers configured to partially overlap during hybridization can be copolymerized into a polyacrylamide hydrogel. At least one of the two or more aptamers further binds to a specific target, e.g., bifunctional tag/target component complex. When the bifunctional tags/target component complexes binds to the aptamer, the number of nucleotide bases available for hybridization between the overlapping aptamers is reduced, causing them to separate. This separation allows the hydrogel to dissolute and release its contents. A target responsive hydrogel can be generated which incorporates aptamers that specifically recognize one or more inflammatory mediators. The hydrogel itself can be loaded with one or more proteases or other reactive components that are configured to modulate a physiological effect of inflammatory mediators. The contents of the hydrogel are released upon binding of the one or more inflammatory mediators to the aptamers associated with the hydrogel. In a further aspect, hydrogels can be used for molecular imprinting. See, e.g., Byrne et al., "Molecular imprinting within hydrogels," *Advanced Drug Delivery Reviews,* 54: 149-161, 2002, which is incorporated herein by reference.

Substrates for One or More Reactive Components

The one or more reactive components including binding agents, denaturing agents, degradative agents, modulators, or combinations there of can be free in solution within one or more second reservoirs of the device. Lower concentration of the reactive components can be used to act locally at the site of the treatment region. Alternatively, the one or more reactive components can be immobilized on a solid substrate within the one or more second reservoirs of the device. The solid substrate can be a matrix, e.g., a bead or filter that is added to one or more second reservoirs of the device. Examples of applicable solid substrates include, but are not limited to, beads, particles, membranes, semi-permeable membranes, capillary, or microarrays. The solid substrate can be comprised of an inorganic material, e.g., glass, alumina, silica, silicon, zirconia, graphite, magnetite, semiconductors, or combinations thereof. Alternatively, the solid substrate can be comprised of an organic material, e.g., polysaccharides including agarose, dextran, cellulose, chitosan, and polyacrylamide, polyacrylate, polystyrene, polyvinyl alcohol, or combinations thereof. Alternatively, the one or more specific binding agents or one or more reactive components can be associated with a solid substrate that are cells, e.g., mammalian cells, enucleated erythrocytes, bacteria, or viral particles or vesicles such as liposomes or other micellular vesicles.

In an aspect, the one or more reactive components, either free in solution or bound to a solid substrate, can be contained near the one or more second reservoirs including the treatment region of the device either by size exclusion using a filter or mesh near the treatment region, containment within a hydrogel or polymer, or by physical attachment to the treatment region of the device. In this aspect, one or more bifunctional tag/target component complexes present in the blood can bind to the one or more reactive components and can be sequestered for inactivation as the blood passes through the device.

The one or more reactive components can be bound to the solid substrate either directly or indirectly. For example, the one or more reactive components can be coupled to the solid substrate by covalent chemical bonds between particular functional groups on the specific binding agent (e.g., primary amines, sulfhydryls, carboxylic acids, hydroxyls, and aldehydes) and reactive groups on the solid substrate. A variety of activating compounds and schemes for directly bonding ligands to solid substrates are known. Some examples include, but are not limited to, cyanogen bromide, cyanuric chlorde, epichlorohydrin, divinyl sulphone, p-toluenesulphonyl chloride, 1,1'-carbonyldiimidazole, sodium meta-periodate, 2-fluoro-1-methylpyridiniumtoluene-4-sulphonate, glycidoxypropyl-trimethoxysilane and 2,2,2-trifluoroethanesulphonyl chloride. For example, cyanogen bromide in base reacts with hydroxyl (OH) groups on agarose solid substrate to form cyanate esters or imidocarbonates. These groups readily react with primary amines under mild conditions resulting in a covalent coupling of the ligand to the agarose solid substrate. Reactive imidocarbonates can also be formed on carbon nanotubes, for example, through reactive carboxyl groups generated by treatment of the nanotubes with oxidizing agents. See, e.g., Bianco, et al., in *Nanomaterials for Medical Diagnosis and Therapy.* pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference. Functionalization of silicon chips with carboxyl groups can be subsequently used to immobilize proteins in the presence of N-ethyl-N'-(3-dimethylaminopropyl) carbodiimide hydrochloride (EDC) and N-hydroxysuccinimide ester (NHS). See, e.g., Hu, et al., *Rapid Commun. Mass Spectrom.* 21:1277-1281, 2007, which is incorporated herein by reference.

The one or more reactive components may or may not have linking or spacer groups bound to the C-terminus which when present can be used to bind the specific binding agent to the solid substrate indirectly. When present the linking group can be a polymer or a monomer. A linking group can be a chain of from 1-10 amino acids. Other examples of linking groups include, but are not limited to, polyethylene glycol, polypropylene glycol, polyesters, polypeptides, polyethers, polysaccharides, glycidoxyalkyl, alkoxyalkyl, alkyl, glycidoxypropyl, ethyl, propyl, phenyl and methacryl; and silicon containing linking groups such as diethyl(triethoxysilylpropyl)malonate; 3-mercaptopropyltrimethoxysilane; 3-aminopropyltrimethoxysilane; N-[(3-trimethoxysilyl)propyl]ethylenediaminetriacetic acid; p-(chloromethyl)phenyltrimethoxysilane; vinyltriethoxysilane; 3-bromopropyltriethoxysilane; and 3-glycidoxypropyltrimethoxysilane.

In general, any of a number of homobifunctional, heterofunctional, and/or photoreactive cross linking agents can be used to conjugate one or more reactive components to an appropriately derivatized substrate. Examples of homobifunctional cross linkers include, but are not limited to, primary amine/primary amine linkers such as BSOCES ((bis(2-[succinimidooxy-carbonyloxy]ethyl) sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2'pyridyldithio]-propionamido) butane). Examples of heterofunctional cross linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-gamma-maleimidobutyryl-oxysuccinimide ester), Sulfo GMBS (N-γ-maleimidobutyryloxysulfosuccinimide ester), EMCS(N-(epsilon-maleimidocaproyloxy) succinimide ester), Sulfo EMCS(N-(epsilon-maleimidocaproyloxy) sulfo succinimide), SIAB (N-succinimidyl(4-iodoacetyl)aminobenzoate), SMCC (succinimidyl 4-(N-maleimidomethyl) cyclohexane-1-carboxylate), SMPB (succinimidyl 4-(rho-maleimidophenyl) butyrate), Sulfo SIAB (N-sulfosuccinimidyl(4-iodoacetyl)aminobenzoate), Sulfo SMCC (sulfosuccinimidyl 4-(N-maleimidomethyl)cyclohexane-1-carboxylate), Sulfo SMPB (sulfosuccinimidyl 4-(rho-maleimidophenyl) butyrate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH (N-(epsilon-maleimidocaproic acid) hydrazide); and amine/carboxyl linkers such as EDC (1-ethyl-3-(3-dimethylaminopropyl) carbodiimide hydrochloride).

In an aspect, the one or more reactive components can be linked to a solid substrate through non-covalent interactions. Examples of non-covalent interactions include, but are not limited to, protein-protein interactions such as those between avidin/streptavidin and biotin, protein A and immunoglobulins, protein G and immunoglobulins, or secondary antibodies with primary antibodies. For example, the one or more reactive components can be modified with biotin using standard methods and bound to a solid substrate derivatized with streptavidin. Alternatively, one or more reactive components can be modified with streptavidin and bound to a solid substrate derivatized with biotin. A single chain antibody can incorporate streptavidin as part of a fusion protein to facilitate attachment of the antibody to the solid substrate via a biotin-streptavidin linkage. See, e.g., Koo, et al. *Appl. Environ. Microbiol.* 64:2497-2502, 1999, which is incorporated herein by reference. Solid substrates such as beads or other particulate substrates derivatized with protein A, protein G, streptavidin, avidin, biotin, secondary antibodies are available from commercial sources (from, e.g., Pierce-Thermo Scientific, Rockford, Ill., Sigma-Aldrich, St. Louis, Mo.). In an aspect, the one or more reactive components can bind to the solid substrate through a non-covalent interaction and be further cross-linked to the solid substrate using a cross-linking agent.

In an aspect, the one or more reactive components can be associated with a solid substrate that are cells, e.g., mammalian cells, enucleated erythrocytes, bacteria, or viral particles, or vesicles such as liposomes or other micellular vesicles. Cells and vesicles can be modified with one or more reactive components using many of the same methods as provided herein. One or more reactive components can be bound to cells or vesicles using one or more homobifunctional or heterofunctional cross-linkers through primary amines and carboxyl groups. Alternatively, cells can be modified with one or more reactive components using a biotin-streptavidin bridge. For example, one or more reactive components can be biotinylated and linked to a non-specifically biotinylated cell surface through a streptavidin bridge. An antibody, aptamer, or receptor can be biotinylated using standard procedures. The surface membrane proteins of a cell can be biotinylated using an amine reactive biotinylation reagent such as, for example, EZ-Link Sulfo-NHS-SS-Biotin (sulfosuccinimidyl 2-(biotinamido)-ethyl-1,3-dithiopropionate; Pierce-Thermo Scientific, Rockford, Ill., USA. See, e.g., Jaiswal, et al. *Nature Biotech.* 21:47-51, 2003; U.S. Pat. No. 6,946,127, which is incorporated herein by reference.

In an aspect, the one or more reactive components can be associated with lipid or micellular vesicles. In an aspect, the one or more reactive components can be antibodies attached to a liposome. Antibodies can be added to liposomes using cross-linking agents and protein A. See, e.g., Renneisen, et al., *J. Bio. Chem.,* 265:16337-16342, 1990, which is incorporated herein by reference. The liposomes are formed from dry lipid in the presence of an aqueous solution, e.g., a buffer of appropriate pH followed by extrusion through a high pressure device fitted with a polycarbonate filter with the desired pore size to form liposomes of a specific size range. The liposomes are modified with N-succinimidyl 3-(2-pyridyldithio) propionate-modified protein A. The one or more antibodies are linked to the liposomes through selective binding to the protein A. Alternatively, thiolated antibodies can be covalently linked to liposomes prepared with 4-(p-maleimidophenyl) butyrylphosphatidyl-ethanolamine. See, e.g., Heath, et al., *PNAS* 80:1377-1381, 1983, which is incorporated herein by reference.

In an aspect, the one or more reactive components can be expressed on the surface of a cell. The one or more reactive components can be naturally expressed on the surface of a cell, such as a receptor of a specific inflammatory mediator on a specific cell type. Alternatively, the one or more reactive components can be expressed on the surface of a cell using genetic manipulation. For example, cells can be genetically manipulated to express a receptor that binds one or more structural elements of the bifunctional tag. In one example, cells can be genetically manipulated to express one or more specific antibodies on the cell surface. Methods have been provided for cell surface expression of single chain Fv antibody fragments (scFv) fused to membrane-associated proteins. See, e.g., Ho, et al., *Proc. Natl. Acad. Sci. USA* 103: 9637-9642, 2006; Francisco, et al., *Proc. Natl. Acad. Sci. USA* 90:10444-10448, 1993; U.S. Pat. Appl. No. 2006/0083716, each of which is incorporated herein by reference. In this aspect, the cDNA sequence encoding all or part of an antibody recognizing a structural element of a bifunctional tag is fused in an expression construct in frame with a membrane-associated protein and expressed in an appropriate cell type.

PROPHETIC EXAMPLES

Example 1

Device Including Bifunctional Tags for Sensing and Sequestering Inflammatory Mediators for Treatment of an Inflammatory Condition or Disease A device is described for treating an inflammatory condition or inflammatory disease associated with elevated levels of tumor necrosis factor alpha (TNF-$\alpha$) in the blood fluid or lymph fluid of a vertebrate subject. The device includes one or more aptamer-based piezoelectric sensors to sense target TNF-$\alpha$ in the blood fluid or lymph fluid of the vertebrate subject and to signal a controller on the device. A controller is configured to control flow of the blood fluid or lymph fluid through a lumen of the device in response to the aptamer-based piezoelectric sensor having sensed elevated levels target TNF-$\alpha$ in the blood fluid or lymph fluid. Upon detection of elevated levels of TNF-$\alpha$ in the blood fluid or lymph fluid, the controller responds by signaling a first set of reservoirs to release one or more bifunctional tags that include antibodies directed against TNF-$\alpha$, which are structural elements capable of binding TNF-$\alpha$. The device further includes binding agents configured to bind the bifunctional tag/target component complex to remove it from the blood fluid or lymph fluid. The binding agents for capturing the bifunctional tag/target component complex are within a second set of reservoirs of the device. The device includes the controller in communication with the sensors, wherein the controller is configured to control flow of the blood fluid or lymph fluid through a lumen of the device and to adjust release of the bifunctional tags to bind and sequester TNF-$\alpha$ to achieve a target value of TNF-$\alpha$, that is, a reduced level of TNF-$\alpha$ compared to elevated levels in the blood fluid or lymph fluid as a result of the inflammatory condition or inflammatory disease in the vertebrate subject. The device includes a receiver for receiving and processing data regarding the sensed levels of TNF-$\alpha$ and a transmitter for transmitting data to an external controller, a computing device, a physician, or a caregiver.

The device is placed in or proximal to one or more blood vessels of a vertebrate subject. The device is a hollow stent-like structure that is placed into a vessel at or near the site of inflammation using a catheter guide wire. The components of the device, including sensors, first and second reservoirs, controller and binding agents, are affixed to and/or incorporated into one or both surfaces of the stent-like structure. The device is configured such that blood fluid or lymph fluid in the vessel is allowed to flow through the lumen either restricted by the controllable flow barrier and the controller, or essentially unobstructed.

The device includes one or more piezoelectric sensors that sense the levels of TNF-$\alpha$ in the blood of the vertebrate subject. The piezoelectric sensors respond to signals from aptamers as target-recognition elements directed against TNF-$\alpha$. Methods for generating aptamers against TNF-$\alpha$ using Systemic Evolution of Ligands by Exponential Enrichment (SELEX) have been described. See, e.g., U.S. Pat. No. 7,309,789, which is incorporated herein by reference. The interaction of TNF-$\alpha$ with the aptamer target recognition elements triggers the piezoelectric sensor to send a signal to the controller. The controller is an integral component of the device. The controller calculates the levels of TNF-$\alpha$ in the blood based on the input from the sensors and compares these data with target values, e.g., desired concentrations of TNF-$\alpha$. The level of TNF-$\alpha$ in a normal human subject is less than about 5 pg/ml. By contrast, a human subject experiencing septic shock may have elevated levels of TNF-$\alpha$ of 140 pg/ml or higher. See, e.g., Ueda, et al., *Am. J. Respir. Crit. Care Med.* 160:132-136, 1999 which is incorporated herein by reference. The target value for TNF-$\alpha$ may be that observed in a normal subject not experiencing an inflammatory disease or a disease resulting in an inflammatory response. In other instances, the target value for TNF-$\alpha$ may represent a reduction of at least 60%, relative to the current level of TNF-$\alpha$ in the blood of the subject. The controller sends a wireless signal to an external controller to alert the subject and/or one or more caregivers as to the levels of TNF-$\alpha$ in the blood of the subject.

The device including the controller releases one or more bifunctional tags from the first reservoir of the device in response to sensing elevated levels of TNF-$\alpha$ in the blood fluid or lymph fluid of a vertebrate subject. The bifunctional tags are stored and controllably released from one or more micro-reservoirs incorporated into the device. The micro-reservoirs are covered by a seal that is disrupted in response to an electrical signal from the controller. See, e.g., U.S. Pat. No. 7,413,846; Maloney & Santini, Proceedings $26^{th}$ Annual International Conference IEEE EMBS, San Francisco, Calif., USA, Sep. 1-5, 2004, each of which is incorporated herein by reference.

The bifunctional tags include a first structural element configured to bind TNF-$\alpha$ and a second structural element configured to interact with a binding agent of the device. The first structural element of the bifunctional tag is an antibody directed against TNF-$\alpha$. Antibodies to TNF-$\alpha$ are available from commercial sources (from, e.g., Sigma-Aldrich, St. Louis, Mo.; or R&D Systems, Inc., Minneapolis, Minn.) or are readily generated using standard methods. The second structural element of the bifunctional tag is biotin configured to bind the binding agent, streptavidin. Biotin is incorporated into the TNF-$\alpha$ antibody and streptavidin is bound to the treatment region of the device. Biotin is incorporated into the TNF-$\alpha$ antibody using standard methods and commercially available labeling kits (e.g., NHS-PEO4-Biotinylation Kit from Thermo Fisher Scientific, Rockford, Ill.). Biotinylated TNF-$\alpha$ antibodies are also be available from commercial sources (e.g., from BioLegend, San Diego, Calif.)

The device further includes one or more binding agents in the treatment region for capturing the bifunctional tag/target component complex. The binding agent is streptavidin configured to bind the biotin structural element of the anti-TNF-$\alpha$ antibody/biotin bifunctional tag in the treatment region of the device. The binding agent, e.g., streptavidin, is incorporated into one or more second reservoirs of the device. A second reservoir of the device is part of the lumen through which all or a portion of the blood fluid or lymph fluid is diverted in response to the sensor and controller sensing elevated levels of the target component. The streptavidin is coated on one or more surfaces of the second reservoir. Streptavidin is coated onto a metal surface using a biotinylated polyelectrolyte linker. See, e.g., Rossetti, et al., *European Cells Mater.* 6 (Suppl. 1):83, 2003, which is incorporated herein by reference. Alternatively, the streptavidin is coated on particles, e.g., silica beads, magnetic beads, or polystyrene beads, which are incorporated into the second reservoir. Streptavidin coated beads are available from a variety of commercial sources (from, e.g., Polysciences, Inc. Warrington, Pa.; Invitrogen, Carlsbad, Calif.; Bangs Laboratories, Inc., Fishers, Ind.). As blood fluid or lymph fluid pass through the lumen of the device, the biotinylated TNF-α antibody/TNF-α complexes bind to the streptavidin in the one or more second reservoirs and are removed from the peripheral circulation of the vertebrate subject. The antibody/TNF-α complexes are ablated in response to irradiation from a near-infrared energy source.

Example 2

Device Including Bifunctional Tags for Sensing and Controllably Sequestering Inflammatory Mediators for Treatment of an Inflammatory Condition or Disease A device is described for treating an inflammatory condition or inflammatory disease associated with elevated levels of interleukin 6 (IL-6) in the blood fluid or lymph fluid of a vertebrate subject. The device includes a sensor that is an aptamer-based molecular beacon to sense IL-6 in the blood fluid or lymph fluid of the vertebrate subject and to signal a controller on the device. A controller is configured to control flow of the blood fluid or lymph fluid through a controllable flow barrier into a lumen of the device in response to the sensor having sensed elevated levels of IL-6 in the blood fluid or lymph fluid. The one or more bifunctional tags include one or more structural elements capable of binding IL-6. The structural elements include antibodies directed against IL-6 and a binding element to the treatment region of the device. The device further includes binding agents configured to bind the bifunctional tag/target component complex to remove it from the blood fluid or lymph fluid. The binding agents for capturing the bifunctional tag/target component complex are within a second set of reservoirs of the device. The binding agents are configured to only bind the bifunctional tag when target component is bound. The device includes the controller in communications with the sensors, wherein the controller is configured to control flow of the blood fluid or lymph fluid through a lumen of the device and to adjust release of the bifunctional tags to bind and sequester IL-6 to achieve a target value of IL-6, that is, a reduced level of IL-6 compared to elevated levels in the blood fluid or lymph fluid as a result of the inflammatory condition or inflammatory disease in the vertebrate subject. The device includes a receiver for receiving and processing data regarding the sensed levels of IL-6 and a transmitter for transmitting data to an external controller, a computing device, a physician, or a caregiver.

The device includes one or more sensors configured to detect the levels IL-6 in the blood of the vertebrate subject. The one or more sensors are aptamer-based molecular beacons designed to fluoresce in response to selectively binding one or more inflammatory mediators. The aptamer-based molecular beacon includes a recognition element, a fluorescing moiety, and a quenching moiety. The recognition element selectively interacts with the target component, e.g., IL-6. Fluorescence induced by electromagnetic energy emitted by the device is quenched in the absence of IL-6. The binding of IL-6 to the selective aptamer induces a conformational change in the aptamer and increases the distance between the fluorescing moiety and the quenching moiety resulting in a fluorescent signal in response to electromagnetic energy. The level of fluorescent signal is proportional to the level of IL-6 in the blood fluid or lymph fluid. The emitted fluorescence is captured by a CCD or CMOS detector in the sensor and a corresponding signal is sent to the controller.

The one or more sensors is operably coupled to the controller, either wirelessly or by circuit, and can transmit data to the controller regarding the detection and/or levels (relative or absolute) of IL-6 in the blood fluid or lymph fluid of the subject. The controller is an integral component of the device. The controller controls an energy source directed against the bound IL-6. The controller includes access to stored data, or data that is stored off-site and coupled either wirelessly or by circuit to the sensor and the controller. The controller also has access to one or more remote databases that include the stored data. The stored data includes data regarding the normal level of IL-6 in normal or healthy subjects without an inflammatory disease or condition. The stored data includes data regarding the baseline level of IL-6 in a subject prior to onset of the inflammatory disease or condition. The stored data also includes data regarding the level of IL-6 in a subject at one or more previous time points. The controller calculates the levels of IL-6 in the peripheral blood based on the input from the sensors and compares these data with target values, e.g., desired concentrations of IL-6. The target value for IL-6 is that observed in a normal subject not experiencing an inflammatory disease or a disease resulting in an inflammatory response. The target value of IL-6 is a low serum level of IL-6 (mean of 15 pg/ml) as compared to a high serum level of IL-6 (mean of 735 pg/ml), the latter of which may be associated with development of severe sepsis and increased risk of death. See, e.g., Kellum, et al., *Arch. Intern. Med.* 167:1655-1663, 2007; Presterl, et al., *Am. J. Respir. Crit. Care Med.* 156:825-832, 1997; which are incorporated herein by reference. The target value for IL-6 represents a reduction of at least 60% relative to the current level of IL-6 in the peripheral blood of the subject. The controller sends a wireless signal to an external controller to alert the subject and/or one or more caregivers as to the levels of IL-6 in the peripheral blood of the subject.

The controller releases the bifunctional tags from the first reservoir of the device in response to molecular beacon sensing elevated levels of IL-6 in the blood fluid or lymph fluid of a vertebrate subject. The bifunctional tags include a first structural element configured to bind IL-6 and a second structural element configured to interact with a binding agent of the device. The first structural element of the bifunctional tag is an antibody directed against IL-6. Antibodies to IL-6 are available from commercial sources (from, e.g., Sigma-Aldrich, St. Louis, Mo.; or R&D system, Inc., Minneapolis, Minn.) or are readily generated using standard methods. The second element of the bifunctional tag is a conformational epitope generated by the binding of IL-6 to the anti-IL-6 antibody and selectively recognized by one or more binding agents at a treatment region of the device.

The device further includes a conformation-specific antibody that includes binding agent for capturing the bifunctional tag/target component complex. The bifunctional tag is configured such that the conformation-specific antibody has an increased affinity for the bifunctional tag bound to the target component (e.g., antibody/IL-6 complex) compared to an affinity for the bifunctional tag unbound to the target component. The conformation-specific antibody is configured to recognize a conformational epitope formed by the binding of IL-6 to an anti-IL-6 antibody. Conformation specific antibodies are generated that selectively bind to an antibody-antigen complex but are unable to bind to either the antibody alone or the antigen alone. See, e.g., Nemazee &

Sato, *Proc. Natl. Acad. Sci, USA.* 79:3828-3832, 1982; U.S. Pat. No. 5,985,579, which are incorporated herein by reference. The binding agent, e.g., the conformation specific antibody, is incorporated into one or more second reservoirs of the device. The second reservoir includes all or part of a lumen through which all or a portion of the blood fluid or lymph fluid has been diverted in response to sensing elevated levels of the IL-6 target component. The conformation-specific antibody is coated on one or more surfaces of the second reservoir and binds the IL-6/anti-IL-6 antibody bifunctional reagent as it passes through the lumen of the device thus removing IL-6 from the peripheral circulation of the vertebrate subject. The antibody/IL-6 complexes are ablated in response to irradiation from a near-infrared energy source.

Example 3

Device Including Bifunctional Tags for Sensing, Binding and Altering Metastatic Tumor Cells for Treatment of a Neoplastic Disease or Condition A device is described for treating a neoplastic disease or condition including one or more light-scattering sensors to sense one or more circulating tumor cells in blood fluid or lymph fluid of a vertebrate subject, a controller configured to release one or more bifunctional tags from a first set of reservoirs in response to the light-scattering sensor. The bifunctional tags are structural elements configured to bind circulating lung tumor cells. The structural elements are antibodies configured to selectively bind an epithelial cell-specific antigen, the epithelial cell-cell adhesion molecule (EpCAM), which is a tumor antigen specific to metastatic tumor cells of epithelial origin. The controller is further configured to control flow of the blood fluid or lymph fluid through a controllable flow barrier into a lumen of the device in response to the sensor, and a reactive component in a treatment region including localized high concentrations of one or more cytotoxic chemotherapeutic agents configured to bind and inactivate the one or more circulating tumor cells. The device is placed in or proximal to one or more blood vessels and includes multiple lumens configured to receive a portion of the blood through a flow route, wherein the controller configured to control flow of blood through the flow route into the lumen. The lumen includes one or more second reservoirs configured with conformational-specific antibodies to the anti-EpCAM/ circulating lung tumor cell complex and are used to sequester the metastatic lung tumor cells within the second reservoir. The second reservoir further includes one or more reactive components including localized high concentrations of one or more cytotoxic chemotherapeutic agents to induce apoptosis or necrosis of the circulating metastatic tumor cells. The second reservoirs can release the components of an AT chemotherapy regimen: doxorubicin, either alone or in combination with paclitaxel. The device includes a receiver for receiving and processing data regarding the sensed levels of circulating metastatic lung tumor cells and a transmitter for transmitting data to an external controller, a computing device, a physician, or a caregiver.

The device includes one or more light-scattering sensors that sense the levels of circulating metastatic lung tumor cells in the blood of a vertebrate subject. Differential light scattering is used to detect circulating tumor cells derived from metastasis of solid tumors. In general, a circulating metastatic lung tumor cell is characterized by its large size, immature appearance, increased nuclear to cytoplasmic ratio, abnormally shaped nuclei, and disproportionately large nucleolus or multiple nucleoli. The size differential between a circulating tumor cell and components of the blood is used to specifically detect the cancerous cells. For example, the average diameter of neutrophils, red bloods cells, and platelets is 10.5-12.5 microns, 7-8 microns, and 3 microns, respectively. In contrast, the average size of circulating tumor cells isolated from subjects with breast, colon, stomach, and lung cancers range from 18.3 to 20.6 microns in diameter. Circulating neuroblastoma tumor cells, for example, are greater than 20 microns in diameter. See, e.g., Moore et al. *Cancer* 13:111-117, 1960; Mohamed et al. *IEEE Transactions on Nanobioscience,* 3:251-256, 2004, each of which is incorporated herein by reference. The size of a cell or cells passing by the one or more sensors is determined using forward and side light scattering. The size, as measured in diameter, is compared with known parameters regarding the size of normal blood components.

The controller calculates the number of circulating metastatic lung tumor cells in the blood fluid or lymph fluid based on the input from the sensors and compares these data with target values, e.g., reduced concentrations of circulating metastatic lung tumor cells to a target value of zero metastatic lung tumor cells in the blood fluid or lymph fluid. However, in some instances, simply lowering the number of circulating metastatic lung tumor cells may improve prognosis. For example, breast cancer patients with levels of circulating tumor cells equal to or higher than five cells per 7.5 milliliters of blood have a shorter median progression-free survival (2.7 months vs. 7.0 months) and shorter overall survival (10 .1 months versus greater than 18.0 months) as compared with breast cancer patients with less than five cells per 7.5 milliliters of blood. See, Cristofanilli et al. *N. Engl. J. Med.* 351: 781-791, 2004, which is incorporated herein by reference. As such, the target value for circulating tumor cells may represent a reduction of at least 60%, relative to the current level of circulating metastatic lung tumor cells in the blood of the subject.

The controller releases bifunctional tags, anti-EpCAM antibody complexed to a secondary binding agent, biotin, from one or more first reservoirs of the device in response to sensing elevated levels of circulating tumor cells in the blood fluid or lymph fluid of a vertebrate subject. The bifunctional tag includes a first structural element anti-EpCAM antibody configured to bind a circulating tumor cell and a second structural element, biotin, configured to interact with a binding agent, streptavidin, in the reaction region of the device. The first structural element of the bifunctional tag is an antibody directed against epithelial cell-cell adhesion molecule (EpCAM), an example of an epithelial cell-specific antigen commonly detected on metastatic tumor cells of epithelial origin. Antibodies to EpCAM are available from commercial sources (from, e.g., Sigma-Aldrich, St. Louis, Mo.; or R&D Systems, Inc., Minneapolis, Minn.) or are readily generated using standard methods. The second structural element of the bifunctional tag is biotin configured to bind a binding agent, streptavidin, of the device. All or part of the anti-EpCAM antibody and all or part of the biotin may be crossed linked together to form a single bifunctional tag. The antibody can be cross-linked with the biotin to form a bifunctional tag using a chemical cross-linking agent, e.g., N-succinimidyl 3-(2-pyridyldithio)propionate (SPDP). See, e.g., U.S. Pat. No. 5,470, 570, which is incorporated herein by reference.

The device further includes one or more binding agents for capturing the bifunctional tag/circulating tumor cell complex. In this example, the binding agent is streptavidin that binds the biotin structural element of the bifunctional tag. The binding agent, e.g., streptavidin, is incorporated into the second reservoir of the device. The second reservoir of the device may be all or part of a lumen through which at least a portion of the blood fluid or lymph fluid has been diverted in response to sensing elevated levels of circulating metastatic lung tumor cells. In this example, the streptavidin is coated on one or more surfaces of the second reservoir. For example, a silicon chip-like surface can be functionalized with carboxyl groups and subsequently used to immobilize proteins, e.g., streptavidin, in the presence of N-ethyl-N'-(3-dimethylaminopropyl)carbodiimide hydrochloride (EDC) and N-hydroxysuccinimide ester (NHS). See, e.g., Hu, et al., *Rapid Commun. Mass Spectrom.* 21: 1277-1281, 2007, which is incorporated herein by reference. Alternatively, the streptavidin can be used to coat particles, e.g., silica beads, magnetic beads, or polystyrene beads, and incorporated into the second reservoir. Activated beads for cross-linking to proteins, e.g., streptavidin, are available from a variety of commercial sources (from, e.g., Polysciences, Inc. Warrington, Pa.; Invitrogen, Carlsbad, Calif.; Bangs Laboratories, Inc., Fishers, Ind.). In this instance, the particles coated with the streptavidin are retained in the treatment region due to either size exclusion or magnetic properties.

The controller controls flow of the blood fluid or lymph fluid into the one or more second reservoirs of the device. The bifunctional tag/circulating tumor cell complexes present in the blood fluid or lymph fluid bind to the one or more binding agents in the second reservoir. Once sequestered in the second reservoir, the circulating tumor cells can be further subjected to one or more reactive components to induce cell-disruption, apoptosis, and/or death of the tumor cells. The one or more second reservoirs is configured to release localized high concentrations of one or more cytotoxic agent, e.g., the chemotherapeutic agent doxorubicin (Adriamycin®), either alone or in combination with paclitaxel (Taxol®) resulting in apoptosis or necrosis of the lung tumor cells. The controller in the device maintains blood flow through the treatment region of the device until reduced target levels of circulating lung tumor cells are reached in the blood fluid or lymph fluid of the subject.

Example 4

Device Including Bifunctional Tags for Sensing, Binding and Altering Inflammatory Mediators for Treatment of an Inflammatory Condition or Disease A device is described for treating an inflammatory condition or inflammatory disease associated with elevated levels of eosinophils in the blood fluid or lymph fluid of a vertebrate subject. The device includes one or more piezoelectric sensor to sense eosinophils in blood fluid or lymph fluid of a vertebrate subject and to signal a controller on the device. The controller is configured to control flow of the blood fluid or lymph fluid through a controllable flow barrier into multiple lumens of the device in response to the piezoelectric sensor having sensed elevated levels of eosinophils in the blood fluid or lymph fluid. The bifunctional tags include one or more structural elements capable of binding eosinophils that include one or more ligands configured to selectively bind receptors on the surface of eosinophils. The one or more structural elements include interleukin 5 (IL-5) directed against the eosinophil cell surface IL-5 receptor. The device is placed in or proximal to one or more vessels and includes multiple lumens configured to receive at least a portion of the blood fluid or lymph fluid through a controllable flow barrier into a flow route, the controller configured to control flow of blood fluid or lymph fluid through the flow route into the multiple lumens. The lumens include one or more second reservoirs configured with one or more binding agents, e.g. streptavidin, for capturing and sequestering the bifunctional tag/eosinophil complex. The second reservoir further includes one or more reactive components, e.g., an energy source emitting near-infrared radiation, to induce thermal ablation of the sequestered eosinophils. The device includes a receiver for receiving and processing data regarding the sensed levels of circulating eosinophils and a transmitter for transmitting data to an external controller, a computing device, a physician, or a caregiver. The device includes one or more sensors that sense the levels of the eosinophils in the blood of the vertebrate subject. The sensors are piezoelectric sensors in which aptamers that recognize surface components of the eosinophils are used as target-recognition elements. The interaction of eosinophils with the aptamer target-recognition elements triggers the piezoelectric sensor to send a signal to the controller. The controller is an integral component of the device. The one or more sensors is operably coupled to the controller, either wirelessly or by circuit, and can transmit data to the controller regarding the detection and/or levels (relative or absolute) of eosinophils in the blood fluid or lymph fluid of the subject. The controller is an integral component of the device. The controller controls other components of the device. The controller controls flow of the blood fluid or lymph fluid through a controllable flow barrier into multiple lumens of the device in response to the piezoelectric sensor having sensed elevated levels of eosinophils in the blood fluid or lymph fluid. The controller controls an energy source directed against the bound eosinophils. The controller includes access to stored data, or data that is stored off-site and coupled either wirelessly or by circuit to the sensor and the controller. The controller also has access to one or more remote databases that include the stored data. The stored data includes data regarding the normal level of eosinophils in normal or healthy subjects without an inflammatory disease or condition. The stored data includes data regarding the baseline level of eosinophils in a subject prior to onset of the inflammatory disease or condition. The stored data also includes data regarding the level of eosinophils in a subject at one or more previous time points. The controller calculates the levels of eosinophils in the blood based on the input from the sensors and compares these data with target values, e.g., desired concentrations of eosinophils. For example, the number of eosinophils in a normal human subject ranges from about 45 cells/microliter to about 450 cells/microliter. By contrast, a human subject experiencing hyper-eosinophilic syndrome (HES) has more than 1500 eosinophils/microliter. See, e.g., Roufosse. *Haematologica* 94:1188-1193, 2009, which is incorporated herein by reference. In some instances, the target value for eosinophils is that observed in a normal subject not experiencing an inflammatory disease or a disease resulting in an inflammatory response. In other instances, the target value for eosinophils may represent a reduction of at least 60% relative to the current level of eosinophils in the blood of the subject. The controller may optionally send a wireless signal to an external controller to alert the subject and/or one or more caregivers as to the levels of eosinophils in the blood of the subject.

The controller controls release of bifunctional tags from the first reservoir of the device in response to sensing elevated levels of eosinophils in the blood fluid or lymph fluid of the vertebrate subject. The bifunctional tag includes a first structural element configured to bind eosinophils and a second structural element configured to interact with a binding agent in a treatment region of the device. The first structural element of the bifunctional tag is IL-5, the ligand for the IL-5 receptor expressed on the surface of eosinophils. The second structural element of the bifunctional tag is biotin configured to bind a binding agent, streptavidin, of the device. A bifunctional tag including IL-5 and biotin is generated as a single fusion protein. Fusion proteins containing interleukins and other ligands can be generated using standard protein engineering techniques. See, e.g., Hu, et. al., *Canc. Res.* 56:4998-5004, 1996, which is incorporated herein by reference.

The device further includes the binding agent, streptavidin, for capturing the bifunctional tag/eosinophil complex. The streptavidin is configured to bind biotin, the second ligand structural element of the bifunctional tag. Streptavidin is incorporated into one or more second reservoirs of the device. The second reservoir of the device is part of a lumen through which at least a portion of the blood fluid or lymph fluid has been diverted in response to sensing elevated levels of eosinophils. The streptavidin is coated onto an array of carbon nanotubes incorporated into a second reservoir of the device. The streptavidin is attached to a carbon nanotube by first functionalizing raw single-walled carbon nanotubes with amino groups using azomethine ylide cycloaddition and then cross-linking a thiolated antibody to the functionalized nanotubes using a heterobifunctional cross-linker such as succiminidyl-4-(N-maleimidomethyl)cyclohexane-1-carboxy-(6-amidocaproate). See, e.g., McDevitt, et al., *J. Nucl. Med.* 48:1180-1189, 2007, which is incorporated herein by reference.

The controller controls flow of the blood fluid or lymph fluid through the controllable flow barrier into the one or more second reservoirs of the device. The bifunctional tag/biotin/eosinophil complexes in the blood fluid or lymph fluid bind to the streptavidin on the carbon nanotube array in the second reservoir. Once sequestered in the second reservoir, the bifunctional tag/biotin/eosinophil complex bound to the streptavidin /carbon nanotube is subjected to one or more reactive components, e.g., near infrared radiation, to induce cell-disruption, apoptosis, and/or death of the cells. The controller controls an energy source directed against the bound eosinophils. The reactive component, near infrared radiation, is used to induce carbon nanotube-mediated thermal ablation of the sequestered eosinophils. Carbon nanotubes are capable of converting near-infrared light into heat and can be used for hyperthermia ablation of targeted cells. See, e.g., Chakravarty, et al., *Proc. Natl. Acad. Sci. USA.* 105:8697-8702, 2008, which is incorporated herein by reference. As blood fluid or lymph fluid pass through the lumen of the device, the bifunctional tag/biotin/eosinophil complexes bind to the streptavidin/carbon nanotubes in the one or more second reservoirs and are ablated in response to irradiation from a near-infrared energy source.

Example 5

Device Including Bifunctional Tags for Binding and Sequestering an Illicit Drug for Treatment of Drug Addiction A device is described for treating an overdose of illicit drug associated with elevated levels of cocaine in the blood fluid or lymph fluid of a vertebrate subject. The device includes one or more sensors to sense fluorescence associated with binding of an aptamer-based molecular beacon to a target component, e.g., cocaine, in the blood fluid or lymph fluid of the vertebrate subject and a controller configured to control flow of the blood fluid or lymph fluid through a lumen in response to the sensor sensing elevated levels of cocaine in the blood fluid or lymph fluid. The bifunctional tag includes one or more structural elements capable of binding cocaine that include an aptamer-based fluorescent molecular beacon that responds to binding of cocaine to the bifunctional tag. The structural element capable of binding cocaine is an aptamer-based fluorescent molecular beacon directed against cocaine. The device includes a sensor for sensing fluorescence associated with binding of cocaine to the aptamer-based molecular beacon. The sensor is in communication with the controller that is further configured to control flow of the blood fluid or lymph fluid through a controllable flow barrier into multiple lumens of the device in response to the sensor having sensed the bifunctional tag/cocaine complex in the blood fluid or lymph fluid. The device further includes binding agents in the treatment region of the device to bind the bifunctional tag/cocaine complex and to remove the complex from the blood fluid or lymph fluid. The device optionally includes a receiver for receiving and processing data regarding the sensed levels of cocaine and a transmitter for transmitting data to an external controller, a computing device, a physician, a corrections officer, or a caregiver.

The controller releases one or more bifunctional tags from one or more first reservoirs of the device in response to sensing cocaine in the blood of a vertebrate subject. The bifunctional tag includes the first structural element, aptamer-based fluorescent molecular beacon directed against cocaine and a second structural element configured to interact with a binding agent of the device. The second structural element is a peptide antigen configured to bind to an antibody binding agent in the treatment region of the device. The cocaine-binding aptamer is further configured to serve as a molecular beacon, generating a fluorescent signal upon binding cocaine. A cocaine-binding aptamer is generated using SELEX in which cocaine is immobilized on a column matrix and screened through iterative rounds against a diverse library of DNA oligonucleotide sequences to find aptamers that selective bind cocaine. The aptamer is further modified by a fluorophore and a quencher to generate a molecular beacon. The cocaine-binding aptamer can be modified with fluorescein and a quencher such as, for example, 4-[4'-((dimethylamino) phenyl)azo-] benzoic acid (DABCYL). See, e.g., Strojanovic, et al. *J. Am. Chem. Soc.* 123:4928-4931, 2001, which is incorporated herein by reference. The first structural element, e.g., cocaine-binding aptamer, and the second structural element, e.g., peptide antigen, are covalently linked to form the bifunctional tag. The aptamer-based molecular beacon is linked to a peptide using a streptavidin-biotin bridge, a thiol-maleimide linkage or disulfide bonds as described by Nitin, et al., *Nucleic Acids Res.* 32:e58, 2004, which is incorporated herein by reference.

The device includes one or more aptamer-based molecular beacon sensors for sensing the interaction of the bifunctional tag with the target component, e.g., cocaine. The sensors are configured to sense fluorescence emitted from bifunctional tag when the target component, e.g., cocaine, has bound to the aptamer-based molecular beacon. The device provides an electromagnetic energy source for illuminating the blood or lymph vessel and a charged couple device (CCD) image capture component for sensing emitted fluorescence. The controller in communication with the sensors is configured to control flow of the blood fluid or lymph fluid through a lumen in response to the sensor having sensed the aptamer-based molecular beacon/cocaine complex in the blood fluid or lymph fluid. Once in the lumen of the device, the aptamer-based molecular beacon /cocaine complex binds to one or more binding agents via the second structural element/peptide antigen of the bifunctional tag bound to an antibody in the treatment region of the device. In this manner, the cocaine is sequestered in the device and removed from the circulation of the subject.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies disclosed herein can be effected (e.g., hardware, software, and/or firmware), and that the preferred vehicle will vary with the context in which the processes and/or systems and/or other technologies are deployed. For example, if a surgeon determines that speed and accuracy are paramount, the surgeon may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies disclosed herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects disclosed herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices disclosed herein, or a microprocessor configured by a computer program which at least partially carries out processes and/or devices disclosed herein), electrical circuitry forming a memory device (e.g., forms of random access memory), and/or electrical circuitry forming a communications device (e.g., a modem, communications switch, or optical-electrical equipment). The subject matter disclosed herein may be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An implantable device comprising:
a body defining at least one lumen configured for fluid flow;
at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject;
at least one treatment region disposed within the at least one lumen; and
at least one second reservoir disposed in the at least one treatment region and configured to include one or more reactive components, wherein the one or more reactive components are configured to sequester the one or more bifunctional tags when bound to the one or more target components;
wherein the one or more reactive components is configured to have an increased affinity for the one or more bifunctional tags bound to the one or more target components compared to an affinity for the one or more bifunctional tags unbound to the one or more reactive components.

2. The device of claim 1, wherein the one or more reactive components is configured to modulate a physiological effect of the one or more target components.

3. The device of claim 1, wherein the one or more bifunctional tags are configured to enter a circulatory system of the mammalian subject at a site different from a site of the one or more reactive components.

4. The device of claim 1, wherein the one or more bifunctional tags includes one or more of a recognition element, recognition molecule, antibody, integrin, selectin, lectin, mimetic polymer, affibody, a label, or virus-like particle.

5. The device of claim 4, wherein the label includes one or more of a QDOT, a nanoparticle, a fluorescent molecule, a magnetic particle, a contrast agent, or a radioisotope.

6. The device of claim 4, wherein the one or more bifunctional tags includes one or more bifunctional antibodies.

7. The device of claim 6, wherein the one or more bifunctional antibodies is configured to bind to one or more of the target component and the reactive component.

8. The device of claim 1, wherein the one or more target components include one or more of circulating target cells or circulating target emboli.

9. The device of claim 8, Wherein the one or more reactive components is configured to produce necrosis or apoptosis in one or more target cells.

10. The device of claim 1, wherein the one or more target components includes one or more of tumor cells, emboli, misfolded proteins, aggregated proteins, antibodies, autoimmune antibodies, infectious agents, or infected cells.

11. The device of claim 8, wherein the one or more target components include cancer cells, pre-cancer cells, autoimmune-related cells, B cells, T cells, phagocytes, platelets, lipoproteins, parasites, viruses, bacteria, fungi, or infected cells.

12. The device of claim 1, wherein the one or more reactive components is configured to alter, arrest, or destroy the one or more target components.

13. The device of claim 1, wherein the one or more reactive components is configured to be placed relative to a tumor or an organ in the mammalian subject.

14. The device of claim 1, wherein the one or more reactive components includes one or more of an adhesion molecule, antibody, binding mimetic, polymer, lectin, integrin, or selectin.

15. The device of claim 1, wherein the one or more reactive components include one or more of a denaturing agent, degradative agent, or binding agent.

16. The device of claim 15, wherein the one or more reactive components include a cytotoxic agent, a cytostatic agent, a programmed cell death-inducing agent, a chemotherapeutic agent, or an antibody-toxin agent.

17. The device of claim 15, wherein the one or more binding agents include one or more of antibodies, receptors, or cognates configured to bind to one or more target components.

18. The device of claim 15, wherein the one or more binding agents include one or more of lectin, binding protein, catalytic antibody, catalytic aptamer, protease conjugate, or photoactivatable conjugate.

19. The device of claim 15, wherein the one or more second reservoirs include a matrix configured to present one or more reactive components.

20. The device of claim 1, further including one or more energy sources configured to supply energy to the at least one treatment region.

21. The device of claim 20, wherein the energy source is coupled to one or more sensor configured to selectively direct energy to the target component.

22. The device of claim 1, further including one or more sensor configured to measure a physiological condition proximate to the device.

23. The device of claim 22, wherein the one or more sensor is configured to detect one or more of unbound bifunctional tags or bifunctional tags bound to target components in the one or more of blood fluid or lymph fluid of the vertebrate subject.

24. The device of claim 22, wherein the one or more sensor is configured to detect sequestration by the at least one reactive component.

25. The device of claim 22, further including a transmitter to report data from the one or more sensor.

26. The device of claim 22, wherein the one or more sensor is configured to report to an outside source or to a computing device.

27. The device of claim 22, wherein the one or more sensor is configured to function in, or proximal to, the one or more blood vessel or lymph vessel.

28. The device of claim 22, wherein the one or more sensor is external to the at least one lumen.

29. The device of claim 22, wherein the one or more sensor is internal to the at least one lumen.

30. The device of claim 22, further including at least one controller in communication with the one or more sensor.

31. The device of claim 30, further including at least one controllable flow barrier to fluid flow into the at least one lumen.

32. The device of claim 31, wherein the at least one controller in communication with the one or more sensor is configured to control the at least one controllable flow barrier to the at least one lumen.

33. The device of claim 32, wherein the one or more sensor is configured to detect the one or more bifunctional tags complexed with the one or more target components and is configured to communicate with the controller to divert flow of the one or more of blood fluid or lymph fluid to the at least one lumen of the device.

34. The device of claim 30, wherein the one or more sensor is configured to detect the one or more target components and configured to communicate with the at least one controller to release the one or more bifunctional tags in response to the one or more detected target components.

35. The device of claim 30, wherein the one or more sensor is configured to detect the one or more bifunctional tags complexed with the one or more target components and is configured to communicate with the controller to activate the one or more reactive components in response to the complex of the one or more bifunctional tags to the one or more target components.

36. The device of claim 1, wherein the one or more reactive components are configured to attach to the at least one lumen.

37. The device of claim 30, wherein the one or more sensor and the at least one controller are configured to achieve a target level of the one or more target components in the vertebrate subject.

38. The device of claim 37, wherein the one or more sensor and the at least one controller are configured to control the at least one controllable flow barrier, to activate the one or more reactive components, to release the one or more bifunctional tags, or to activate one or more energy sources.

39. The device of claim 37, wherein the one or more sensor and the at least one controller are configured to control levels of the detected one or more target components to limit a deviation from the target level.

40. The device of claim 39, wherein the deviation is determined by a weighted least squares fit.

41. The device of claim 37, wherein the target level includes a desired concentration of the one or more target components in the one or more of blood fluid or lymph fluid.

42. The device of claim 37, wherein the target level includes a desired range of concentrations of the one or more target components in the one or more of blood fluid or lymph fluid.

43. The device of claim 37, wherein the target level includes a desired ratio of concentrations of two or more target components in the one or more of blood fluid or lymph fluid.

44. The device of claim 37, wherein the target level includes a desired ratio of levels of two or more target components in the one or more of blood fluid or lymph fluid.

45. The device of claim 30, wherein the at least one first reservoir configured to provide one or more bifunctional tags is responsive to the controller.

46. The device of claim 30, wherein the at least one second reservoir configured to provide one or more reactive components is responsive to the controller.

47. The device of claim 22, wherein the one or more sensor includes a biosensor, chemical sensor, physical sensor, or optical sensor.

48. The device of claim 47, wherein the one or more sensor includes one or more target recognition elements.

49. The device of claim 22, wherein the one or more sensor is configured to target the device to a site having an elevated level of the one or more target components.

50. An implantable device, comprising:
a body defining at least one lumen configured for fluid flow;
at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject;
at least one treatment region disposed within the at least one lumen;
at least one second reservoir disposed in the at least one treatment region and configured to include one or more reactive components, wherein the one or more reactive components are configured to sequester the one or more bifunctional tags when bound to the one or more target components;
further including two or more parallel lumens configures to receive the one or more target components.

51. The device of claim 50, wherein a diameter of each of the two or more lumen is approximately less than two cell diameters.

52. The device of claim 50, wherein a diameter of each of the two or more lumen is approximately less than 10 μm.

53. An implantable device, comprising:
a body defining at least one lumen configured for fluid flow;
at least one first reservoir disposed within the at least one lumen and configured to include one or more bifunctional tags, wherein the one or more bifunctional tags are configured to selectively bind to one or more target components in one or more of blood fluid or lymph fluid of a vertebrate subject;
at least one treatment region disposed within the at least one lumen;
at least one second reservoir disposed in the at least one treatment region and configured to include one or more reactive components, wherein the one or more reactive components are configured to sequester the one or more bifunctional tags when bound to the one or more target components;
wherein the one or more second reservoirs include a source for producing the one or more reactive components, the source including at least one reservoir and one producer.

* * * * *